(12) United States Patent
Davidson et al.

(10) Patent No.: US 10,080,851 B2
(45) Date of Patent: Sep. 25, 2018

(54) METHOD AND DEVICE FOR VAPORIZATION AND INHALATION OF ISOLATED SUBSTANCES

(71) Applicant: Syqe Medical Ltd., Tel-Aviv (IL)

(72) Inventors: Perry Davidson, Tel-Aviv (IL); Aaron Schorr, Doar-Na Misgav (IL); Asaf Kroll, Kfar-Vitkin (IL); Binyamin Schwartz, Sde Eliezer (IL)

(73) Assignee: Syqe Medical Ltd., Tel-Aviv (IL)

( * ) Notice: Subject to any disclaimer, the term of this patent is extended or adjusted under 35 U.S.C. 154(b) by 0 days.

(21) Appl. No.: 15/382,819

(22) Filed: Dec. 19, 2016

(65) Prior Publication Data

US 2017/0136196 A1  May 18, 2017

Related U.S. Application Data

(63) Continuation of application No. PCT/IL2015/050673, filed on Jun. 30, 2015.
(Continued)

(51) Int. Cl.
*A61M 11/00* (2006.01)
*A61M 15/00* (2006.01)
(Continued)

(52) U.S. Cl.
CPC ....... *A61M 15/0028* (2013.01); *A24F 47/008* (2013.01); *A61M 11/042* (2014.02); *A61M 15/002* (2014.02)

(58) Field of Classification Search
CPC .... A61K 9/0012; A61K 9/007; A61K 9/0073; A61M 11/04; A61M 11/041;
(Continued)

(56) References Cited

U.S. PATENT DOCUMENTS 3,203,432 A  8/1965  Green et al.
3,894,544 A  7/1975  Egri
(Continued)

FOREIGN PATENT DOCUMENTS

AU  199641966  5/1996
EP  2292108  3/2011
(Continued)

OTHER PUBLICATIONS

Communication Relating to the Results od the Partial International Search dated May 18, 2012 From the International Searching Authority Re. Application No. PCT/IL2011/050071.
(Continued)

*Primary Examiner* — Michael Tsai

(57) ABSTRACT

A dose unit including at least one isolated bioactive agent applied on a carrier material in thermal contact with an electrically heating element configured to vaporize a predetermined amount of the agent for pulmonary delivery thereof is provided herein, as well as devices for effecting vaporization and pulmonary delivery of the isolated agent, and methods for preparing the dose unit, controllably releasing the agent therefrom, methods for pulmonary delivery thereof and methods of treatment of medical conditions treatable by pulmonary delivery of the isolated bioactive agent.

28 Claims, 21 Drawing Sheets
(1 of 21 Drawing Sheet(s) Filed in Color)

Related U.S. Application Data

(60) Provisional application No. 62/019,225, filed on Jun. 30, 2014, provisional application No. 62/035,588, filed on Aug. 11, 2014, provisional application No. 62/085,772, filed on Dec. 1, 2014, provisional application No. 62/086,208, filed on Dec. 2, 2014, provisional application No. 62/164,710, filed on May 21, 2015.

(51) Int. Cl.
  *A61M 11/04* (2006.01)
  *A24F 47/00* (2006.01)

(58) Field of Classification Search
  CPC .............. A61M 11/042; A61M 11/044; A61M 15/0028; A61M 15/0061; A61M 15/0063; A61M 15/0066; A61M 15/0091; A61M 15/02
  See application file for complete search history.

(56) References Cited

U.S. PATENT DOCUMENTS

| | | |
|---|---|---|
| 4,735,358 A | 4/1988 | Morita et al. |
| 4,966,171 A | 10/1990 | Serrano et al. |
| 4,969,477 A | 11/1990 | Yagisawa |
| 5,301,666 A | 4/1994 | Lerk et al. |
| 5,388,594 A | 2/1995 | Counts et al. |
| 5,404,871 A | 4/1995 | Goodman et al. |
| 5,479,948 A | 1/1996 | Counts et al. |
| 5,649,554 A | 7/1997 | Sprinkel et al. |
| 5,655,520 A | 8/1997 | Howe et al. |
| 5,792,057 A | 8/1998 | Rubsamen et al. |
| 6,703,418 B2 | 3/2004 | Plasse |
| 6,761,164 B2 | 7/2004 | Amirpour et al. |
| 7,088,914 B2 | 8/2006 | Whittle et al. |
| 7,169,378 B2 | 1/2007 | Rabinowitz et al. |
| 7,287,530 B1 | 10/2007 | Stuart |
| 7,537,005 B2 | 5/2009 | Dave |
| 7,987,846 B2 | 8/2011 | Hale et al. |
| 8,235,037 B2 | 8/2012 | Hale et al. |
| 8,408,200 B2 | 4/2013 | Clark et al. |
| 8,615,407 B2 | 12/2013 | Hyde et al. |
| 2001/0027789 A1 | 10/2001 | Goede et al. |
| 2002/0168322 A1 | 11/2002 | Clark et al. |
| 2003/0037785 A1 | 2/2003 | Sonntag |
| 2003/0041859 A1 | 3/2003 | Abrams et al. |
| 2003/0062042 A1 | 4/2003 | Wensley et al. |
| 2003/0168057 A1 | 9/2003 | Snyder et al. |
| 2003/0200964 A1 | 10/2003 | Blakley et al. |
| 2004/0045567 A1 | 3/2004 | Lewis et al. |
| 2004/0069798 A1 | 4/2004 | Grey et al. |
| 2004/0084044 A1 | 5/2004 | Childers et al. |
| 2004/0099266 A1 | 5/2004 | Cross et al. |
| 2004/0192760 A1 | 9/2004 | Whittle et al. |
| 2005/0063686 A1 | 3/2005 | Whittle et al. |
| 2005/0126562 A1 | 6/2005 | Rabinowitz et al. |
| 2005/0244521 A1 | 11/2005 | Strickland et al. |
| 2005/0268909 A1 | 12/2005 | Bonney et al. |
| 2005/0268911 A1* | 12/2005 | Cross ................ A61M 15/0045 128/204.17 |
| 2006/0102175 A1 | 5/2006 | Nelson |
| 2006/0120962 A1 | 6/2006 | Rabinowitz et al. |
| 2006/0157491 A1 | 7/2006 | Whittle et al. |
| 2006/0167084 A1 | 7/2006 | Dudley |
| 2006/0258738 A1 | 11/2006 | Dieterich |
| 2007/0072938 A1 | 3/2007 | Rose |
| 2007/0122353 A1 | 3/2007 | Hale et al. |
| 2007/0074721 A1 | 4/2007 | Harmer et al. |
| 2007/0102013 A1 | 5/2007 | Adams et al. |
| 2007/0209661 A1 | 9/2007 | Smyth et al. |
| 2007/0240712 A1 | 10/2007 | Fleming et al. |
| 2007/0286816 A1 | 12/2007 | Hale et al. |
| 2008/0072898 A1 | 3/2008 | Quoniam |
| 2008/0078382 A1 | 4/2008 | LeMahieu et al. |
| 2008/0140250 A1 | 6/2008 | Dave |
| 2008/0176885 A1 | 7/2008 | Holtman et al. |
| 2008/0181942 A1 | 7/2008 | Zajicek |
| 2008/0299048 A1 | 12/2008 | Hale et al. |
| 2008/0311176 A1 | 12/2008 | Hale et al. |
| 2009/0084865 A1 | 4/2009 | Maharajh |
| 2009/0151722 A1 | 6/2009 | Eason et al. |
| 2009/0197941 A1 | 8/2009 | Guy et al. |
| 2009/0241949 A1 | 10/2009 | Smutney et al. |
| 2009/0293888 A1 | 12/2009 | Williams et al. |
| 2009/0308390 A1 | 12/2009 | Smutney et al. |
| 2009/0320836 A1 | 12/2009 | Baker, Jr. |
| 2010/0012118 A1 | 1/2010 | Storz |
| 2010/0035978 A1 | 2/2010 | Guy et al. |
| 2010/0154795 A1 | 6/2010 | Pentafragas |
| 2010/0168228 A1 | 7/2010 | Bose |
| 2010/0181387 A1 | 7/2010 | Zaffaroni et al. |
| 2010/0204602 A1 | 8/2010 | Addington et al. |
| 2010/0250280 A1 | 9/2010 | Sutherland |
| 2010/0294278 A1 | 11/2010 | Mosier et al. |
| 2010/0326438 A1 | 12/2010 | Dunne |
| 2011/0030706 A1 | 2/2011 | Gibson et al. |
| 2011/0036346 A1 | 2/2011 | Cohen et al. |
| 2011/0038958 A1 | 2/2011 | Kikuchi et al. |
| 2011/0126831 A1 | 6/2011 | Fernandez Pernia |
| 2011/0244020 A1 | 10/2011 | Hale et al. |
| 2011/0265806 A1 | 11/2011 | Alarcon et al. |
| 2012/0252885 A1 | 10/2012 | Barbato |
| 2012/0255546 A1 | 10/2012 | Goetz et al. |
| 2012/0304990 A1 | 12/2012 | Todd |
| 2012/0325227 A1 | 12/2012 | Robinson et al. |
| 2013/0032139 A1 | 2/2013 | Hale et al. |
| 2013/0081623 A1 | 4/2013 | Buchberger |
| 2013/0087144 A1 | 4/2013 | Todd |
| 2013/0112197 A1 | 5/2013 | Kruener et al. |
| 2013/0213397 A1 | 8/2013 | Curtis et al. |
| 2013/0276799 A1 | 10/2013 | Davidson et al. |
| 2013/0333700 A1 | 12/2013 | Buchberger |
| 2014/0060525 A1 | 3/2014 | Hale et al. |
| 2014/0088045 A1 | 3/2014 | Rigas et al. |
| 2014/0100249 A1 | 4/2014 | Sears et al. |
| 2014/0144429 A1* | 5/2014 | Wensley ............... A61M 15/06 128/200.14 |
| 2014/0190496 A1 | 7/2014 | Wensley et al. |
| 2014/0238423 A1 | 8/2014 | Tucker et al. |
| 2015/0064672 A1 | 3/2015 | Bars |
| 2015/0075521 A1 | 3/2015 | Lee et al. |
| 2015/0090253 A1 | 4/2015 | Farrow |
| 2015/0122252 A1 | 5/2015 | Frija |
| 2015/0136124 A1 | 5/2015 | Aronie et al. |
| 2015/0237913 A1 | 8/2015 | Suzuki et al. |
| 2016/0007653 A1 | 1/2016 | Tu |
| 2016/0044960 A1 | 2/2016 | O'Connor |
| 2016/0100624 A1 | 4/2016 | Yilmaz et al. |
| 2016/0166786 A1 | 6/2016 | Kinzer |
| 2016/0171164 A1 | 6/2016 | Kinzer |
| 2016/0183589 A1 | 6/2016 | Born et al. |
| 2016/0271347 A1 | 9/2016 | Raichman |
| 2016/0286860 A1 | 10/2016 | Flayler |
| 2016/0295922 A1 | 10/2016 | John et al. |
| 2016/0331022 A1 | 11/2016 | Cameron |
| 2016/0331913 A1 | 11/2016 | Bourque |
| 2017/0095624 A1 | 4/2017 | Davidson et al. |
| 2017/0106153 A1 | 4/2017 | Davidson et al. |
| 2017/0119979 A1 | 5/2017 | Davidson et al. |
| 2017/0119981 A1 | 5/2017 | Davidson et al. |
| 2017/0127727 A1 | 5/2017 | Davidson et al. |
| 2017/0150755 A1 | 6/2017 | Batista |
| 2017/0157343 A1 | 6/2017 | Davidson et al. |
| 2017/0164657 A1 | 6/2017 | Batista |
| 2017/0203058 A1 | 7/2017 | Davidson et al. |
| 2017/0360089 A1 | 12/2017 | Davidson et al. |

FOREIGN PATENT DOCUMENTS

| | | |
|---|---|---|
| GB | 2108390 | 5/1983 |
| GB | 2340758 | 3/2000 |
| GB | 2495771 | 4/2013 |

(56) References Cited

FOREIGN PATENT DOCUMENTS

| WO | WO 98/04308 | 2/1998 |
|---|---|---|
| WO | WO 00/24362 | 5/2000 |
| WO | WO 03/037412 | 5/2003 |
| WO | WO 2005/061033 | 7/2005 |
| WO | WO 2008/024408 | 2/2008 |
| WO | WO 2008/024490 | 2/2008 |
| WO | WO 2008/116165 | 9/2008 |
| WO | WO 2009/124552 | 10/2009 |
| WO | WO 2010/015260 | 2/2010 |
| WO | WO 2011/073306 | 6/2011 |
| WO | WO 2012/006125 | 1/2012 |
| WO | WO 2012/006126 | 1/2012 |
| WO | WO 2012/026963 | 3/2012 |
| WO | WO 2012/085919 | 6/2012 |
| WO | WO 2013/057185 | 4/2013 |
| WO | WO 2013/083636 | 6/2013 |
| WO | WO 2014/061477 | 4/2014 |
| WO | WO 2015/123064 | 8/2015 |
| WO | WO 2015/123317 | 8/2015 |
| WO | WO 2015/175979 | 11/2015 |
| WO | WO 2016/001921 | 1/2016 |
| WO | WO 2016/001922 | 1/2016 |
| WO | WO 2016/001923 | 1/2016 |
| WO | WO 2016/001924 | 1/2016 |
| WO | WO 2016/001925 | 1/2016 |
| WO | WO 2016/001926 | 1/2016 |
| WO | WO 2016/090303 | 6/2016 |
| WO | WO 2016/147188 | 9/2016 |
| WO | WO 2016/172802 | 11/2016 |
| WO | WO 2016/187696 | 12/2016 |
| WO | WO 2017/118980 | 7/2017 |

OTHER PUBLICATIONS

International Preliminary Report on Patentability dated Jul. 2, 2013 From the International Preliminary Examining Authority Re. Application No. PCT/IL2011/050071.
International Preliminary Report on Patentability dated Jan. 12, 2017 From the International Bureau of WIPO Re. Application No. PCT/IL2015/050673. (15 Pages).
International Preliminary Report on Patentability dated Jan. 12, 2017 From the International Bureau of WIPO Re. Application No. PCT/IL2015/050674. (11 Pages).
International Preliminary Report on Patentability dated Jan. 12, 2017 From the International Bureau of WIPO Re. Application No. PCT/IL2015/050675. (8 Pages).
International Preliminary Report on Patentability dated Jan. 12, 2017 From the International Bureau of WIPO Re. Application No. PCT/IL2015/050677. (13 Pages).
International Preliminary Report on Patentability dated Jan. 12, 2017 From the International Bureau of WIPO Re. Application No. PCT/IL2015/050678. (12 Pages).
International Preliminary Report on Patentability dated Jan. 12, 2017 From the International Bureau of WIPO Re. Application No. PCT/IL2015/50676. (11 Pages).
International Search Report and the Written Opinion dated Oct. 19, 2012 From the International Searching Authority Re. Application No. PCT/IL2011/050071.
Office Action dated Jan. 19, 2017 From the Israel Patent Office Re. Application No. 227102 and Its Translation Into English. (5 Pages).
Office Action dated Jun. 22, 2016 From the Israel Patent Office Re. Application No. 227102 and Its Translation Into English.
Official Action dated Jan. 30, 2017 From the US Patent and Trademark Office Re. U.S. Appl. No. 13/997,302. (23 pages).
Official Action dated Sep. 30, 2016 From the US Patent and Trademark Office Re. U.S. Appl. No. 13/997,302.
Restriction Official Action dated Jul. 8, 2016 From the US Patent and Trademark Office Re. U.S. Appl. No. 13/997,302.
Written Opinion dated Apr. 22, 2013 From the International Preliminary Examining Authority Re. Application No. PCT/IL2011/050071.

Ibrahim et al. "Inhalation Drug Delivery Devices: Technology Update", Medical Devices: Evidence and Research, 8: 131-139, Feb. 12, 2015.
Lanz et al. "Medicinal Cannabis: In Vitro Validation of Vaporizers for the Smoke-Free Inhalation of Cannabis", Plos One, 11(1): e0147286-1-e0147286-18, Jan. 19, 2016.
Pomahacova et al. "Cannabis Smoke Condensate III: The Cannabinoid Content of Vaporised Cannabis Sativa", Inhalation Toxicology, 21(13): 1108-1112, Nov. 1, 2009.
Communication Relating to the Results of the Partial International Search dated Oct. 22, 2015 From the International Searching Authority Re. Application No. PCT/IL2015/050673.
Communication Relating to the Results of the Partial International Search dated Sep. 24, 2015 From the International Searching Authority Re. Application No. PCT/IL2015/050677.
International Search Report and the Written Opinion dated Feb. 2, 2016 From the International Searching Authority Re. Application No. PCT/IL2015/050673.
International Search Report and the Written Opinion dated Dec. 3, 2015 From the International Searching Authority Re. Application No. PCT/IL2015/050677.
International Search Report and the Written Opinion dated Jan. 7, 2016 From the International Searching Authority Re. Application No. PCT/IL2015/050675.
International Search Report and the Written Opinion dated Dec. 10, 2015 From the International Searching Authority Re. Application No. PCT/IL2015/050674.
International Search Report and the Written Opinion dated Jan. 20, 2016 From the International Searching Authority Re. Application No. PCT/IL2015/50676.
International Search Report and the Written Opinion dated Oct. 22, 2015 From the International Searching Authority Re. Application No. PCT/IL2015/050678.
AAAAI "Inhaled Asthma Medications: Tips to Remember", American Academy of Allergy Asthma & Immunology, AAAAI, 4 P., 2013.
Abrams et al. "Vaporization as a Smokeless Cannabis Delivery System: A Pilot Study", Clinical Pharmacology & Therapeutics, 82(5): 572-578, Advance Online Publication Apr. 11, 2007.
Bhattacharyya et al. "Opposite Effects of Delta-9-Tetrahydrocannabinol and Psychopathology", Neuropsychopharmacology, 35: 764-774, 2010.
Boden et al. "The Effects of Cannabis Use Expectancies on Self-Initiated Cannabis Cessation", Addiction, 108: 1649-1657, 2013.
Das et al. "Effects of 9-Ene-Tetrahydrocannabinol on Expression of Beta-Type Transforming Growth Factors, Insulin-Like Growth Factor-I and C-Myc Genes in the Mouse Uterus", The Journal of Steroid Biochemistry and Molecular Biology, 45(6): 459-465, 1993.
Eisenberg et al. "The Pharmacokinetics, Efficacy, Safety, and Ease of Use of A Novel Portable Metered-Dose Cannabis Inhaler in Patients With Chronic Neuropathic Pain: A Phase 1a Study", Journal of Pain & Palliative Care Pharmacotherapy, 28(3): 216-225, Published Online Aug. 13, 2014.
Farrimond et al. "Cannabinol and Cannabidiol Exert Opposing Effects on Rat Feeding Patterns", Psychopharmacology, 223: 117-129, 2012.
FDA "Guidance for Industry. Population Pharmacokinetics", U.S. Department of Health and Human Services, Food and Drug Administration (FDA), Center for Drug Evaluation and Research (CDER), Center for Biological Evaluation and Research (CBER), CP 1: 1-31, Feb. 1999.
Hazekamp et al. "Bedrocan®—Stimulating the Development of Herbal Cannabis-Based Products", Bedromedical Presentation, 2013.
Hazekamp et al. "Evaluation of A Vaporizing (Volcano®) for the Pulmonary Administration of Tetrahydrocannabinol", Journal of Pharmaceutical Sciences, 95(6): 1308-1317, Jun. 2006.
Hazekamp et al. "The Medicinal Use of Cannabis and Cannabinoids—An International Cross-Sectional Survey on Administration Forms", Journal of Psychoactive Drugs, 45(3): 199-210, 2013.
Herbalizer "Herbalizer, the New Vaporization Experience", 6 P., Jun. 7, 2013.
Jamontt et al. "The Effects of Delta[9]-Tetrahydrocannabinol and Cannabidiol Alone and in Combination on Damage, Inflammation

(56) References Cited

OTHER PUBLICATIONS and In Vitro Motility Disturbances in Rat Colitis", British Journal of Pharmacology, 160: 712-723, 2010.
McPartland et al. "Are Cannabidiol and Delta9-Tetrahydrocannabivarin Negative Modulators of the Endocannabinoid System? A Systematic Review", British Journal of Pharmacology, 172(3): 737-753, Published Online Jan. 8, 2015.
Mechoulam et al. "Cannabidiol—Recent Advances", Chemistry & Biodiversity, 4: 1678-1692, 2007.
Pertwee "The Diverse CB1 and CB2 Receptor Pharmacology of Three Plant Cannabinoids: Delta[9]-Tetrahydrocannabinol, Cannabidiol and Delta[9]-Tetrahydrocannabivarin", British Journal of Pharmacology, 153: 199-215, 2008.
Rabinowitz et al. "Fast Onset Medications Through Thermally Generated Aerosols", The Journal of Pharmacological and Experimental Therapeutics, 309(2): 769-775, 2004.
Rau "The Inhalation of Drugs: Advantages and Problems", Respiratory Care, 50(3): 367-382, Mar. 2005.
Cohen et al. "Modelling of the Concentration—Effect Relationship of THC on Central Nervous System Parameters and Heart Rate—Insight Into Its Mechanisms of Action and a Tool for Clinical Research and Development of Cannabinoids", Journal of Pharmacology, 22(7): 717-726, Sep. 2008.
Syqe Medical "The World's First Metered Dose Pharmaceutical Grade Medical Cannabis Inhaler", Syqe Medical™, Press Kit, p. 1-8, 2015.
Van Gerven "Biomarkers to Assess Adverse Drug Effects on the CNS", Centre for Human Drug Research, CHDR, Poster-Session, Slide-Show, 25 P., 2013.
Van Hell et al. "Evidence for Involvement of the Insula in the Psychotropic Effects of THC in Humans: A Double-Blind, Randomized Pharamcological MRI Study", International Journal of Neuropharmacology, 14: 1377-1388, 2011.
Vann et al. "Divergent Effects of Cannabidiol on the Discriminative Stimulus and Place Conditioning Effects of Delta 9-Tetrahydrocannabiol", Drug and Alcohol Dependence, 94(1-3): 191-198, Apr. 1, 2008.
Vemuri et al. "Pharmacotherapeutic Targeting of the Endocannabinoid Signaling.System: Drugs for Obesity and the Metabolic Syndrome", Physiology & Behavior, 93: 671-686, 2008.
Wallace et al. "Efficacy of Inhaled Cannabis on Painful Diabetic Neuropathy", The Journal of Pain, 169(7): 616-627, Published Online Apr. 3, 2015.
Ware et al. "Smoked Cannabis for Chronic Neuropathic Pain: A Randomized Controlled Trial", Canadian Medical Association Journal, CMAJ, 182(14): E694-E701, Published Online Aug. 30, 2010.
Wilsey et al. "Low-Dose Vaporized Cannabis Significantly Improves Neuropathic Pain", The Journal of Pain, 14(2): 136-148, Published Online Dec. 13, 2012.
Zuurman et al. "Biomarkers for the Effects of Cannabis and THC in Healthy Volunteers", British Journal of Clinical Pharmacology, 67(1): 5-21, 2008.
Zuurman et al. "Effect of Intrapulmonary Tetrahydrocannabinol Administration in Humans", Journal of Psychopharmacology, 22(7): 707-716, 2008.
Official Action dated Mar. 9, 2017 From the US Patent and Trademark Office Re. U.S. Appl. No. 15/386,182. (24 pages).
Official Action dated Mar. 13, 2017 From the US Patent and Trademark Office Re. U.S. Appl. No. 15/391,896. (22 pages).
International Search Report and the Written Opinion dated Mar. 27, 2017 From the International Searching Authority Re. Application No. PCT/IL2017/050014. (16 pages).
Official Action dated Apr. 6, 2017 From the US Patent and Trademark Office Re. U.S. Appl. No. 15/362,841. (35 pages).
Official Action dated Apr. 10, 2017 From the US Patent and Trademark Office Re. U.S. Appl. No. 15/362,883. (33 pages).
Notice of Allowance dated Jun. 1, 2017 From the US Patent and Trademark Office Re. U.S. Appl. No. 13/997,302. (24 pages).
Official Action dated Jun. 1, 2017 From the US Patent and Trademark Office Re. U.S. Appl. No. 15/375,098. (42 pages).

Jang et al. "Thennophysical Properties of Porous SiC Ceramics Fabricated by Pressureless Sintering", Science and Technology of Advanced Materials, 8(7): 655-659, Nov. 30, 2007.
Norwood et al. "Best Practices for Extractables and Leachables in Orally Inhaled and Nasal Drug Products: An Overview of the PQRI Recommendations", Pharmaceutical Research, 25(4): 727-739, Published Online Jan. 9, 2008.
Communication Pursuant to Article 94(3) EPC dated Jun. 23, 2017 From the European Patent Office Re. Application No. 11815728.8. (5 Pages).
Restriction Official Action dated Aug. 7, 2017 From the US Patent and Trademark Office Re. U.S. Appl. No. 15/312,647. (8 pages).
Official Action dated Aug. 18, 2017 From the US Patent and Trademark Office Re. U.S. Appl. No. 15/308,370. (56 pages).
Official Action dated Sep. 22, 2017 From the US Patent and Trademark Office Re. U.S. Appl. No. 15/362,883. (43 pages).
Official Action dated Sep. 28, 2017 From the US Patent and Trademark Office Re. U.S. Appl. No. 15/312,647. (57 pages).
Applicant-Initiated Interview Summary dated May 22, 2017 From the US Patent and Trademark Office Re. U.S. Appl. No. 15/386,182. (3 pages).
Applicant-Initiated Interview Summary dated May 23, 2017 From the US Patent and Trademark Office Re. U.S. Appl. No. 15/362,841. (3 pages).
Applicant-Initiated Interview Summary dated May 23, 2017 From the US Patent and Trademark Office Re. U.S. Appl. No. 15/362,883. (3pages).
Applicant-Initiated Interview Summary dated May 23, 2017 From the US Patent and Trademark Office Re. U.S. Appl. No. 15/375,098. (3 pages).
Communication Pursuant to Article 94(3) EPC dated Jan. 19, 2018 From the European Patent Office Re. Application No. 15744363.1. (4 Pages).
Communication Pursuant to Article 94(3) EPC dated Jan. 22, 2018 From the European Patent Office Re. Application No. 15756490.7. (4 Pages).
Assaf et al. "Pre- and Post-Conditioning Treatment With An Ultra-Low Dose of [Delta]sup9-Tetrahydrocannabinol (THC) Protects Against Pentylenetetrazole (PTZ)-Induced Cognitive Damage", Behavioral Brain Research, 220(1): 194-201, Jun. 2011.
Fishbein et al. "Long-Term Behavioral and Biochemical Effects of an Ultra-Low Dose of [Delta]sup9-Tetrahydrocannabinol (THC): Neuroprotection and ERK Signaling", Experimental Brain Research, 221(4): 437-448, Published Online Jul. 22, 2012.
Official Action dated Dec. 12, 2017 From the US Patent and Trademark Office Re. U.S. Appl. No. 15/308,370. (27 pages).
Communication Pursuant to Article 94(3) EPC dated Feb. 26, 2018 From the European Patent Office Re. Application No. 15753782.0. (6 Pages).
Official Action dated Mar. 14, 2018 From the US Patent and Trademark Office Re. U.S. Appl. No. 15/362,883. (21 pages).
Applicant-Initiated Interview Summary dated Jan. 5, 2018 From the US Patent and Trademark Office Re. U.S. Appl. No. 15/382,819. (3 pages).
Applicant-Initiated Interview Summary dated Dec. 22, 2017 From the US Patent and Trademark Office Re. U.S. Appl. No. 15/312,647. (3 pages).
Applicant-Initiated Interview Summary dated Dec. 22, 2017 From the US Patent and Trademark Office Re. U.S. Appl. No. 15/362,883. (3 pages).
Office Action dated Dec. 21, 2017 From the Israel Patent Office Re. Application No. 227102 and Its Translation Into English. (4 Pages).
Official Action dated Jan. 25, 2018 From the US Patent and Trademark Office Re. U.S. Appl. No. 15/375,098. (37 pages).
Official Action dated Dec. 26, 2017 From the US Patent and Trademark Office Re. U.S. Appl. No. 15/391,896. (53 pages).
Requisition by the Examiner dated Nov. 16, 2017 From the Innovation, Science and Economic Development Canada, Canadian Intellectual Property Office Re. Application No. 2,822,738. (4 Pages).

(56) References Cited

OTHER PUBLICATIONS

Carter et al. "Medicinal Cannabis: Rational Guidelines for Dosing", IDrugs, 7(5): 464-470, May 2004.

* cited by examiner

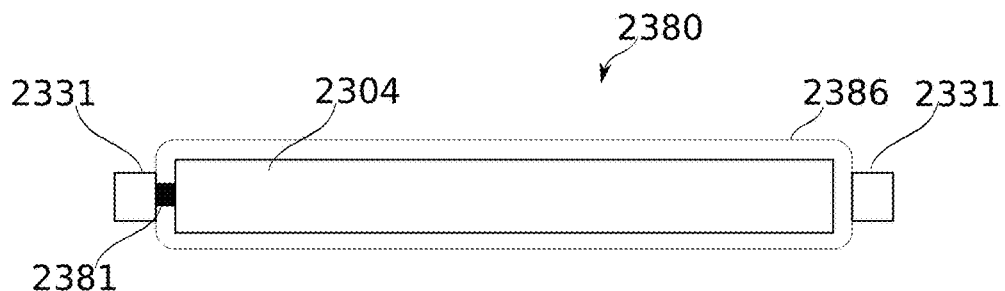
FIG. 1I
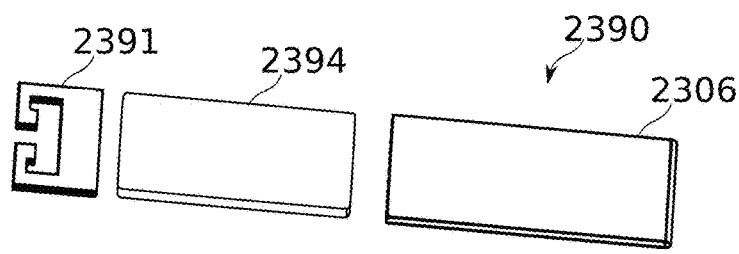
FIG. 1J
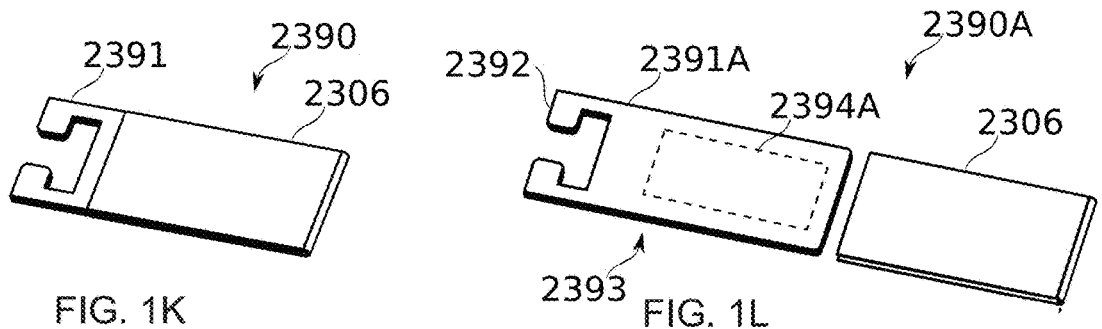
FIG. 1K
FIG. 1L
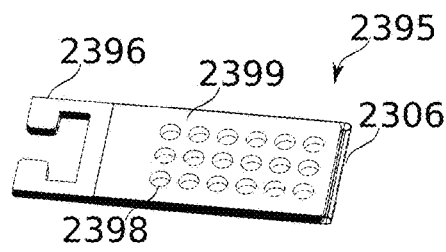
FIG. 1M

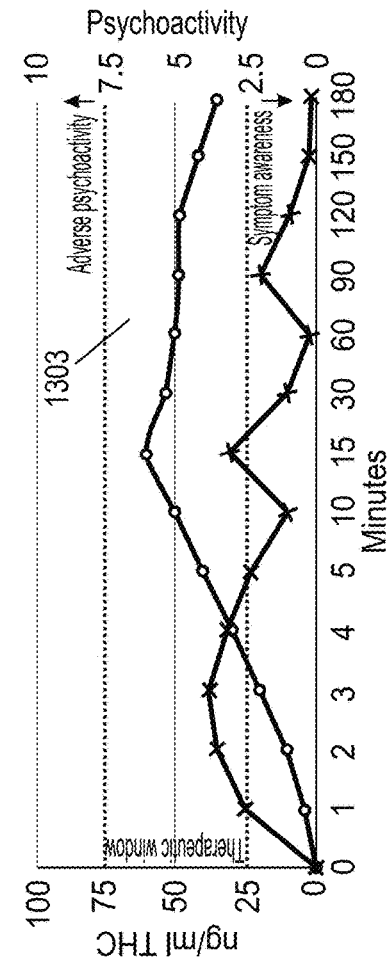
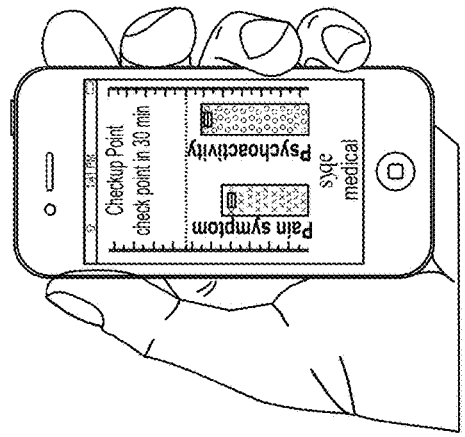
FIG. 10A
FIG. 10B
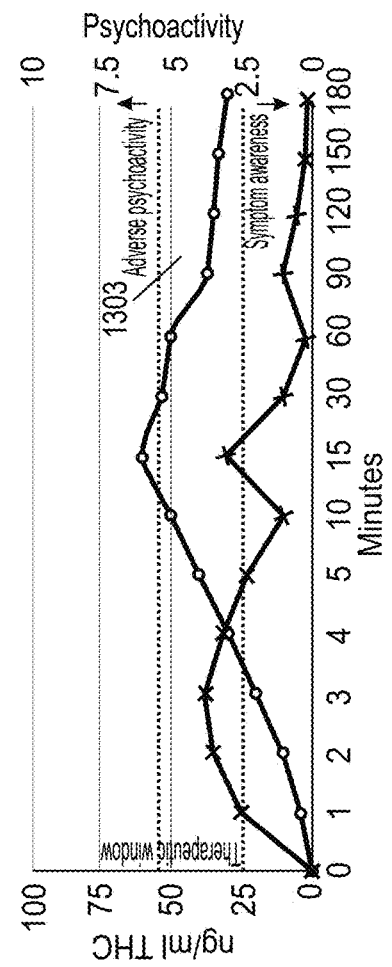
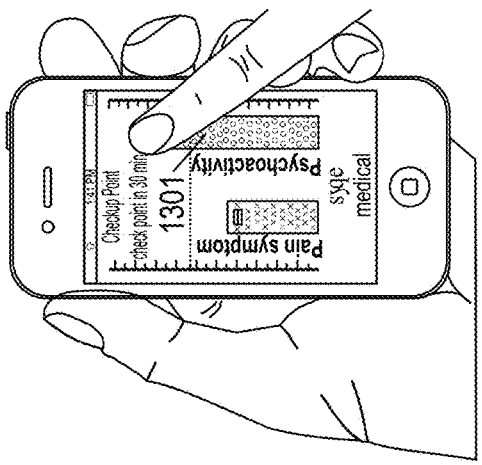
FIG. 10C
FIG. 10D

METHOD AND DEVICE FOR VAPORIZATION AND INHALATION OF ISOLATED SUBSTANCES

RELATED APPLICATIONS

This application is a Continuation of PCT Patent Application No. PCT/IL2015/050673 filed on Jun. 30, 2015, which claims the benefit of priority under 35 USC § 119(e) of U.S. Provisional Patent Application Nos. 62/019,225 filed on Jun. 30, 2014, 62/035,588 filed on Aug. 11, 2014, 62/085,772 filed on Dec. 1, 2014, 62/086,208 filed on Dec. 2, 2014 and 62/164,710 filed on May 21, 2015.

PCT Patent Application No. PCT/IL2015/050673 was co-filed on Jun. 30, 2015 with PCT Patent Application Nos. PCT/IL2015/050677, PCT/IL2015/050678, PCT/IL2015/050676, PCT/IL2015/050674 and PCT/IL2015/050675. The contents of the above applications are all incorporated by reference as if fully set forth herein in their entirety.

FIELD AND BACKGROUND OF THE INVENTION

The present disclosure, in some embodiments thereof, relates to pharmacology and, more particularly, but not exclusively, to methods and devices for controlled delivery by inhalation of vaporizable substances.

Over the years, many methods and devices have been developed to achieve the efficient delivery of a bioactive (pharmaceutically active) agent to a subject requiring pharmaceutical treatment. Oral ingestion, intravenous delivery and subcutaneous injection represent the two most common examples of current delivery techniques. While these techniques are generally effective, they suffer from several pharmacokinetic limitations and further often result in substantial non-compliance by patients. For example, the therapeutic benefit from conventional methods often wear off within several hours after initial dosing while the discomfort associated with injections often lead to difficulties in administration and maintenance. Even oral administration can be ineffective in cases where the bioactive agent exhibits poor bioavailability and in cases of subjects incapable of ingesting the bioactive agent due to nausea and/or vomiting.

One of the examples of a highly effective bioactive agent in dronabinol—a pure isomer of THC, or (-)-trans-$\Delta$9-tetrahydrocannabinol, which is one of the main bioactive substances found in cannabis. Dronabinol is manufactured synthetically and marketed under the trade name Marinol®, however, the drug's use is rather limited due to its intrinsic properties, such as viscosity and hydrophobicity, which are expressed pharmaceutically in low bioavailability and incontrollable efficacy when delivered by ingestion. For example, it takes over one hour for Marinol® to reach full systemic effect compared to seconds or minutes for smoked or vaporized cannabis. Some patients accustomed to inhaling just enough cannabis smoke to manage symptoms have complained of too-intense and untimely belated intoxication from Marinol's predetermined dosages. Many patients have said that Marinol produces a more acute psychedelic effect than cannabis, and it has been speculated that this disparity can be explained by the difficulty is controlling the amount of the bioactive agent in the subject at any given time point since this viscous hydrophobic agent, once absorbed through the GI tract, may be temporarily stored in fatty tissue before reaching the target receptors in the CNS.

While smoking is generally not recommended due to the ill effects of smoke inhalation and the low efficiency in delivery the un-combusted bioactive agent, vaporization and inhalation of the vapors of drugs suffering from low bioavailability may present a viable solution to the problems associated with injection and ingestion thereof. A partial solution is provided by some vaporization techniques aimed at delivering inhaled vaporizable bioactive agents while avoiding the respiratory hazards of smoking. While the temperature at the center of a burning cigarette is 750-800° C., vaporization can be performed at any predetermined temperature, thereby allowing vapors of the bioactive agent to form below the combustion temperature, at which pyrolytic toxic compounds are generated. It has been shown that vaporization techniques reduce formation of carbon monoxide and highly carcinogenic compounds such as polynuclear aromatic hydrocarbons (PAHs), benzene and tar.

However none of the currently known smokeless vaporization devices can be utilized for administering vaporizable bioactive agents under common pharmaceutical standards and practices, due to the inability to accurately and reproducibly control the amount that the patient inhales. The pulmonary delivery of vaporizable bioactive agents in the vapor phase varies within and between practically delivered doses due to the subjective visual estimation of the dose amount loaded by the user, repeated asynchronous inhalations from the same loaded dose, inconsistent inhalation dynamics and a time-dependent condensation of vapors onto the inner surfaces of the device. Subsequently, vaporizers in use today make proper pharmaceutical dosing and medical regimen monitoring unrealistic or impractical.

International Patent Application Publication No. WO 2008/116165 discloses systems and methods for pulmonary delivery of a drug to the respiratory system of a patient, wherein the drug is supplied in purified air at a positive pressure relative to atmospheric pressure, whereas medication available in a variety of forms is introduced in a controlled fashion into the purified air stream in aerosol, nebulized, or vaporized form.

U.S. Patent Application Publication No. 20140238423 discloses an electronic smoking article which includes a supply of a liquid material and a heater-wick element operable to wick liquid material and heat the liquid material to a temperature sufficient to vaporize the liquid material and form an aerosol. The heater-wick element comprises two or more layers of electrically resistive mesh material. This device affords no controllability and/or reproducibility in the mount being delivered to the subject.

Rabinowitz, J. D. et al. [*J. Pharmacol. Exp. Ther.*, 2004, 309(2), p. 769-75] teach systemic delivery of pure pharmaceutical compounds without degradation products through a related process that also involves inhalation of thermally generated aerosol. According to Rabinowitz, J. D. et al., a drug is coated as a thin film on a metallic heating element and vaporized by heating the element; the thin nature of the drug coating minimizes the length of time during which the drug is exposed to elevated temperatures, thereby preventing its thermal decomposition, and the vaporized, gas-phase drug rapidly condenses and coagulates into micrometer-sized aerosol particles.

International Patent Application No. WO 2012/085919, by the present assignees, which is incorporated herein by reference, discloses inter alia metered dose inhalation devices for controlled vaporization and pulmonary delivery of bioactive agents from plant material by application of heat, wherein the device is configured to vaporize a precise amount of an agent from the plant material in a highly reproducible manner while exerting air-flow control to guarantee complete pulmonary delivery of the pre-determined dose.

Additional background art include International Patent Application Nos. WO 2008/024490 and WO 2008/024408, U.S. Pat. Nos. 6,703,418, 7,169,378, 7,987,846 and 8,235,037 and U.S. Patent Application Publication Nos. 20140100249, 20120252885, 20100168228, 20080181942, 20080176885, 20080078382, 20070072938, 20060258738 and 20060167084.

SUMMARY OF THE INVENTION

A dose unit comprising at least one isolated bioactive agent applied on a carrier material in thermal contact with a heating element configured to vaporize a pre-determined amount of the agent for pulmonary delivery thereof is provided herein, as well as devices for effecting vaporization and pulmonary delivery of the isolated agent, and methods for preparing the dose unit, controllably releasing the agent therefrom, methods for pulmonary delivery thereof and methods of treatment of medical conditions treatable by pulmonary delivery of the isolated bioactive agent.

According to an aspect of some embodiments of the present disclosure, there is provided a dose unit for pulmonary delivering at least one bioactive agent to a user, which includes:

a pallet; and an electrically resistive heating element in thermal contact with and extending across at least a portion of a surface of the pallet, wherein the at least one bioactive agent is included in an isolated bioactive agent, and the pallet includes a solid carrier material and the bioactive agent is in and/or on the carrier material.

According to some embodiments, the electrically resistive heating element extends across at least two opposite surfaces of the pallet.

According to some embodiments, the carrier material is substantially unreactive with the bioactive agent when in contact with the bioactive agent at a temperature range that falls within the range spanning from a storage temperature to a combustion/decomposition temperature of the bioactive agent.

According to some embodiments, the carrier material is substantially unreactive with the bioactive agent when in contact with the bioactive agent at a temperature range spanning from a storage temperature to a temperature being 50° C. higher than an evaporation temperature of the bioactive agent.

According to some embodiments, the carrier material has a combustion and/or decomposition and/or melting temperature higher than an evaporation temperature of the bioactive agent.

According to some embodiments, the carrier material has a combustion and/or decomposition and/or melting temperature higher than an evaporation temperature of the bioactive agent by at least 50° C.

According to some embodiments, the carrier material has an electric resistivity of at least 10 μΩ·m.

According to some embodiments, the carrier material has a thermal conductivity of at least 0.1 W/mK.

According to some embodiments, the carrier material includes a substance selected from the group consisting of glass, quartz, ceramic composite, silicon carbide, mullite, alumina, silicone and polytetrafluoroethylene.

According to some embodiments, the pallet has an air-permeable structure that allows a flow of at least 0.5 liter of gas per minute under a pulling vacuum of at least 1-5 kPa.

According to some embodiments, the pallet is a unified air-permeable matrix.

According to some embodiments, the pallet is an air-permeable plurality of packed particles.

According to some embodiments, the particles have a diameter larger than 10 microns.

According to some embodiments, the isolated bioactive agent is a liquid having a viscosity of at least 10 centipoise (cP).

According to some embodiments, the boiling point of the isolated bioactive agent is higher than 80° C.

According to some embodiments, the octanol-water partition coefficient (log P) of the isolated bioactive agent is greater than 5.

According to some embodiments, the octanol-water partition coefficient (log P) of the isolated bioactive agent is greater than 1.

According to some embodiments, the isolated bioactive agent includes a synthetic bioactive agent.

According to some embodiments, the isolated bioactive agent includes a pure extract of a plant substance.

According to some embodiments, the bioactive agent is selected from the group consisting of Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV), cannabitriol (CBT), a terpene, a flavinoid and any combination thereof.

According to some embodiments, the bioactive agent is selected from the group consisting of opium, salvinorin, cathinone, pukateine, thujone, damianin, bulbocapnine, kavalactone, lagochilin, lactucarium, glaucine, ergine, ibogaine, aporphine, leonurine, atropine, buprenorphine, butorphanol, fentanyl, hydromorphone, methadone, midazolam, nalbuphine, naloxone, naltrexone, oxycodone, phenytoin, remifentanil, rizatriptan, sildenafil, sufentanil and zolpidem.

According to some embodiments, the bioactive agent is (-)-trans-Δ9-tetrahydrocannabinol (dronabinol).

According to some embodiments, the bioactive agent is provided in and/or on the carrier material at a pre-determined amount.

According to some embodiments, the resistive heating element is a metal heating element.

According to some embodiments, the resistive heating element includes a U-shape with two ends and having a hollow in which the pallet is positioned, such that an electrical current flows across both of the at least two opposite surfaces when a voltage is applied between the two ends.

According to some embodiments, the resistive heating element is anchored to the pallet, retaining the pallet to the dose unit.

According to some embodiments, the resistive heating element has a portion encased and extending within the pallet.

According to some embodiments, the portion of the resistive heating element extending across the pallet is an air-permeable resistive heating element.

According to some embodiments, the air-permeable resistive heating element allows a flow of at least 0.5 liter of gas per minute under a pulling vacuum of at least 1-5 kPa.

According to some embodiments, the resistive heating element includes a resistive mesh.

According to some embodiments, the resistive heating element includes at least one ribbon of etched metal foil.

According to some embodiments, the ribbon of etched metal foil is backed by a polymer backing includes a plurality of perforations making it air-permeable.

According to some embodiments, the ribbon of etched metal foil includes a narrowed region having elevated resistance, which melts to break an electrical continuity along the ribbon during dissipation of electrical power applied after release the bioactive agent.

According to some embodiments, the ribbon of etched metal foil is attached to a fuse element configured to break electrical continuity along the ribbon during dissipation of electrical power applied after release the bioactive agent.

According to some embodiments, the dose unit includes an air-permeable retaining mesh separating the pallet and the heating element, the retaining mesh being sufficiently closed to retain the pallet in the dose unit.

According to some embodiments, the air-permeable retaining mesh allows a flow of at least 0.5 liter of gas per minute under a pulling vacuum of at least 1-5 kPa.

According to some embodiments, the resistive heating element includes an electrode contact-receiving region on either side of a region extending across the pallet.

According to some embodiments, the resistive heating element includes a transport arm interlock region, shaped for attachment to the transport arm of a dose puller.

According to some embodiments, the dose unit includes a plurality of heating element regions, each region being separately configured to receive electric current.

According to some embodiments, the heating elements are associated with a corresponding plurality of pallets.

According to some embodiments, the dose unit further includes a frame, into an aperture of which the pallet is fittingly pressed.

According to some embodiments, the frame is resistant to heat of at least a temperature at which the bioactive agent vaporizes.

According to some embodiments, the resistive heating element is in thermal contact with the pallet and extending at least across the aperture.

According to some embodiments, the resistive heating element is partially embedded in the frame around the edges of the aperture.

According to some embodiments, the frame includes a region away from the aperture at which the resistive heating element is attached.

According to some embodiments, the resistive heating element is attached to the region by at least partial melting of the frame at the region, such that material of the frame flows into one or more apertures in the resistive heating element.

According to some embodiments, the frame includes a transport arm interlock region, shaped for attachment to the transport arm of a dose puller.

According to an aspect of some embodiments of the present disclosure, there is provided an activating unit for the dose unit according to any of the embodiments presented herein, which includes:

a dose puller configured to move the dose unit from a storage position into a use position;

a holder configured for holding the dose unit such that the bioactive agent is in sealed alignment with an air conduit of the activating unit; and electrodes positioned to be in electrical contact with at least two electrical contact receiving regions of the resistive heating element of the dose unit when in the activating unit.

According to some embodiments, the dose puller includes a dose pulling arm, shaped to interlock with a receiving region of the dose unit such that movement of the dose pulling arm moves the dose unit into or out of the use position.

According to some embodiments, the sealed alignment defines a pathway through the pallet within a lumen along which air passing through the pallet continues until reaching an exit aperture.

According to some embodiments, the holder includes the mechanism configured to move the dose unit.

According to an aspect of some embodiments of the present disclosure, there is provided an inhaler device which includes the activating unit according to any of the embodiments presented herein.

According to some embodiments, the inhaler device includes a dose unit dispensing apparatus that includes a plurality of dose units within a closed container.

According to some embodiments, the closed container includes an interlock which, after dispensing of a first dose unit from the container, prevents dispensing of a second dose unit from the container until the first dose unit is returned to the dispensing apparatus.

According to some embodiments, the dose unit is dispensed to a vaporizing apparatus, and an operation of the interlock includes inserting the vaporizing apparatus into the dose unit dispensing apparatus.

According to some embodiments, the device includes a clamping chamber apparatus that includes:

a compartment sized to fittingly receive a dose unit from a dose unit container while the clamping chamber apparatus is fitted to the dose unit container, and a power unit operable, while the clamping chamber apparatus is removed from the dose unit container, to deliver current to the resistive heating element of the fittingly received dose unit, for vaporization of the bioactive agent contained in the dose unit.

According to some embodiments, the dose unit container contains a plurality of the dose units.

According to some embodiments, the device is configured to release at least one pre-determined vaporized amount of the bioactive agent upon controllably heating the pallet includes the bioactive agent.

According to some embodiments, the device includes a temperature sensor for sensing the temperature in one or more of in the dose unit and on the dose unit.

According to an aspect of some embodiments of the present disclosure, there is provided a process of manufacturing the dose unit according to any of the embodiments presented herein, which includes:

contacting the carrier material with the isolated bioactive agent;

forming a pallet that includes the carrier material having the bioactive agent applied therein and/or thereon; and covering the pallet on at least a portion of one side by the electrically resistive heating element.

According to some embodiments, forming the pallet includes:

placing a plurality of particles of the carrier material having the bioactive agent applied therein and/or thereon within a dose chamber on a planar surface;

vibrating the planar surface until the plurality of particles is leveled; and pressing the leveled plurality of particles to form the pallet.

According to some embodiments, forming the pallet includes cutting a section from the carrier material to form a unified air-permeable matrix.

According to some embodiments, cutting a section from the carrier material is performed prior to the contacting the carrier material with the isolated bioactive agent.

According to an aspect of some embodiments of the present disclosure, there is provided a method of pulmonary delivering at least one bioactive agent to a patient, which includes:

loading a dose unit into an activating unit of an inhaler device according to any of the embodiments presented herein;

applying a current to the resistive heating element of the dose unit to thereby vaporize a pre-determined vaporized amount of the bioactive agent thereby controllably releasing the pre-determined vaporized amount.

According to some embodiments, the method includes, subsequent to applying the current, inhaling ambient air through the pallet, thereby pulmonary delivering the pre-determined vaporized amount to a pulmonary organ of a patient.

According to some embodiments, the pre-determined vaporized amount is selected so as to exhibit at least one pre-selected pharmacokinetic profile and/or at least one pre-selected pharmacodynamic profile of the bioactive agent in the patient.

According to some embodiments, the method further includes:

determining at least one pharmacokinetic parameter and/or at least one pharmacokinetic variable and/or at least one pharmacodynamic parameter induced by the pulmonary delivering the isolated bioactive agent in the patient from the device; based on the pharmacokinetic parameter and/or the pharmacokinetic variable and/or the pharmacodynamic parameter, determining the pre-determined vaporized amount which exhibits the pre-selected pharmacokinetic profile and/or the pre-selected pharmacodynamic profile of the bioactive agent in the patient; and adjusting the device to deliver the at least one pre-determined vaporized amount of the bioactive agent.

According to some embodiments, each of the pharmacokinetic parameter and/or the pharmacokinetic variable and/or the pharmacodynamic parameter is determined for an individual patient, such that the pre-determined vaporized amount is determined personally for the patient.

According to some embodiments, the pre-selected pharmacodynamic profile ranges between a minimal level of a desired effect and a level of an undesired effect.

According to some embodiments, the pharmacodynamic profile ranges between a minimal level of a desired effect to a minimal level of an undesired effect.

According to some embodiments, the pharmacodynamic profile ranges between a minimal level of a desired effect to a level higher than a minimal level of an undesired effect.

According to some embodiments, defining at least one of the desired effect and/or the undesired effect includes receiving instructions from the patient and/or a physician.

According to some embodiments, the pre-selected pharmacodynamic profile is selected from the group consisting of:

a pharmacodynamic profile within a level lower than a minimal level of a therapeutic effect;

a pharmacodynamic profile ranging within a minimal level of the therapeutic effect to a maximal level of the therapeutic effect in which an adverse effect is not exhibited or perceived, and a pharmacodynamic profile within a level higher than a minimal level of an adverse effect.

According to some embodiments, the pharmacodynamic profile ranges within a minimal level of the therapeutic effect to a maximal level of the therapeutic effect in which an adverse effect is not exhibited or perceived.

According to an aspect of some embodiments of the present disclosure, there is provided a method of treating a medical condition treatable by inhalation of at least one pre-determined vaporized amount of at least one bioactive agent, effected by the method according to any of the embodiments presented herein.

According to some embodiments, the medical condition is selected from the group consisting of alcohol abuse, amyotrophic lateral sclerosis, anorexia nervosa, anxiety disorders, appetite variations, asthma, atherosclerosis, bipolar disorder, bladder dysfunction, chronic obstructive pulmonary disease (COPD), collagen-induced arthritis, colorectal cancer, Crohn's disease, delirium, digestive diseases, Dravet's Syndrome, drug addiction and craving, dystonia, epilepsy, fibromyalgia, generalized epilepsy with febrile seizures plus (GEFS+), glaucoma, gliomas, hepatitis C, HIV-associated sensory neuropathy depression, Huntington's disease, hypertension, increased intra ocular pressure, inflammatory bowel disease (IBD), insomnia, irritable bowel syndrome (IBS), lack of appetite, leukemia, migraines, movement disorders, multiple sclerosis (MS), nausea, neurogenic pain, neuropathic pain, nociceptive pain, Parkinson's disease, phantom pain, posttraumatic stress disorder (PTSD), premenstrual syndrome, pruritus, psychiatric disorders, psychogenic pain (psychalgia or somatoform pain), seizures, septic and cardiogenic shock, sexual dysfunction, skin tumors, sleep apnea, spasticity, spinal cord injury, tics, Tourette symptoms, tremors, unintentional weight loss and vomiting.

According to an aspect of some embodiments of the present disclosure, there is provided a dose unit for pulmonary delivering at least one bioactive agent to a user which includes:

a frame having an aperture; and a pallet consisting of a solid carrier material and being fittingly pressed into the aperture;

wherein the pallet is sufficiently air permeable to allow a flow of at least 0.5 liter of gas per minute under a pulling vacuum of at least 1-5 kPa through the pallet.

According to some embodiments, the dose unit includes a resistive heating element in thermal contact with and extending across at least two opposite surfaces of the pallet, wherein the pallet together with the resistive heating element are sufficiently air permeable to allow a flow of at least 0.5 liter of gas per minute under a pulling vacuum of at least 1-5 kPa through the pallet between the at least two opposite surfaces.

According to some embodiments, the pallet is sufficiently air permeable to allow a flow of at least 0.5 liter of gas per minute under a pulling vacuum of at least 1-5 kPa through the pallet between the at least two opposite surfaces.

According to some embodiments, the carrier material has an electric resistivity of at least 10 μΩ·m.

According to some embodiments, the carrier material has a thermal conductivity of at least 0.1 W/mK.

According to some embodiments, the carrier material is selected from the group consisting of glass, quartz, ceramic composite, silicon carbide, mullite, alumina, silicone and polytetrafluoroethylene.

According to some embodiments, the pallet is a unified air-permeable matrix.

According to some embodiments, the pallet is an air-permeable plurality of packed particles.

According to some embodiments, the particles have a diameter larger than 10 microns.

Unless otherwise defined, all technical and/or scientific terms used herein have the same meaning as commonly understood by one of ordinary skill in the art to which an invention pertains. Although methods and materials similar or equivalent to those described herein can be used in the practice or testing of embodiments of an invention, some methods and/or materials are described below. In case of conflict, the patent specification, including definitions, will control. In addition, the materials, methods, and examples are illustrative only and are not intended to be necessarily limiting.

As will be appreciated by one skilled in the art, aspects of an invention may be embodied as a system, method or computer program product. Accordingly, aspects of an invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some aspects may take the form of a computer program product embodied in one or more computer readable medium(s) having computer readable program code embodied thereon. Implementation of the method and/or system of embodiments can involve performing or completing selected tasks manually, automatically, or a combination thereof. Moreover, according to actual instrumentation and equipment of embodiments of the method and/or system of this disclosure, several selected tasks could be implemented by hardware, by software or by firmware or by a combination thereof using an operating system.

For example, hardware for performing selected tasks according to some embodiments could be implemented as a chip or a circuit. As software, selected tasks according to some embodiments could be implemented as a plurality of software instructions being executed by a computer using any suitable operating system. In some embodiments, one or more tasks according to some embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments are described herein, by way of example only, with reference to the accompanying drawings. With specific reference now to the drawings in detail, it is stressed that the particulars shown are by way of example and for purposes of illustrative discussion of the embodiments. In this regard, the description taken with the drawings makes apparent to those skilled in the art how some embodiments may be practiced.

In the drawings:

Figure 3A:
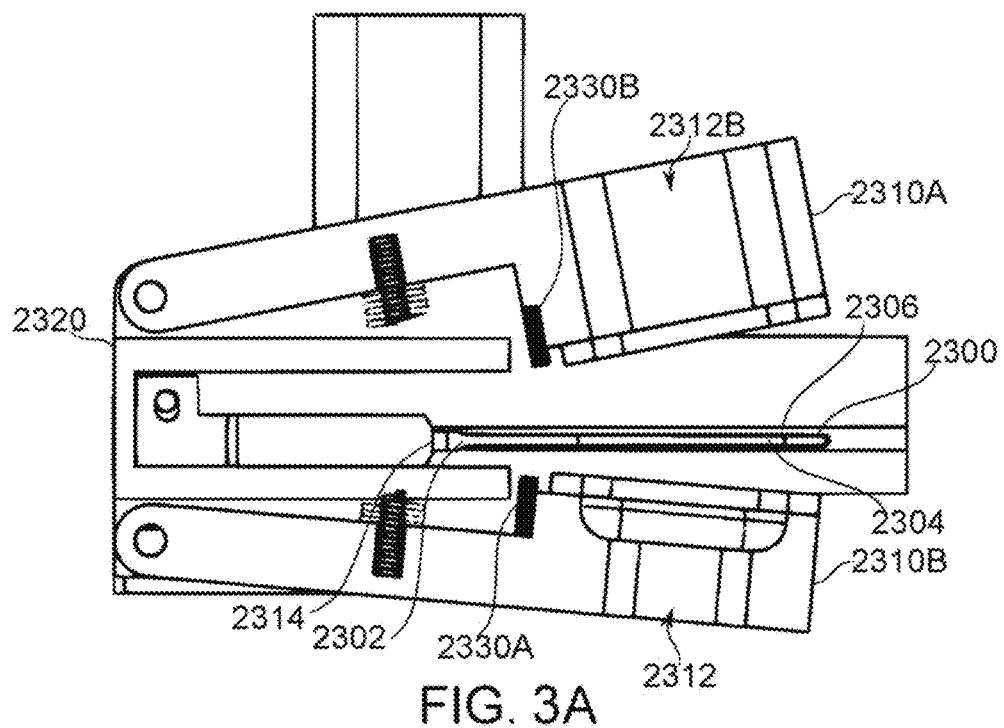
Figure 3B:
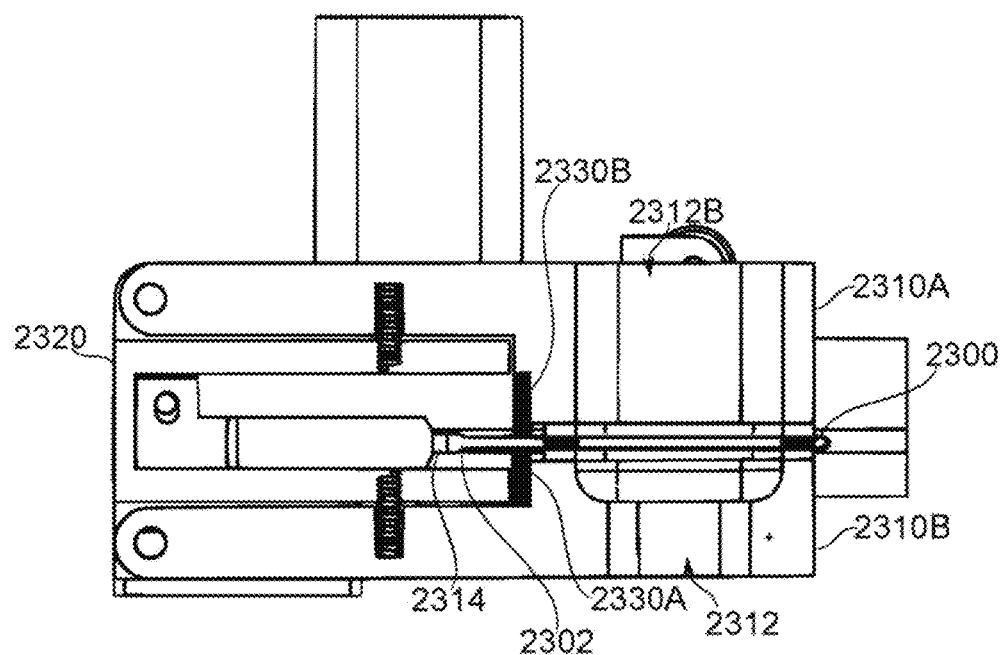
Figure 4A:
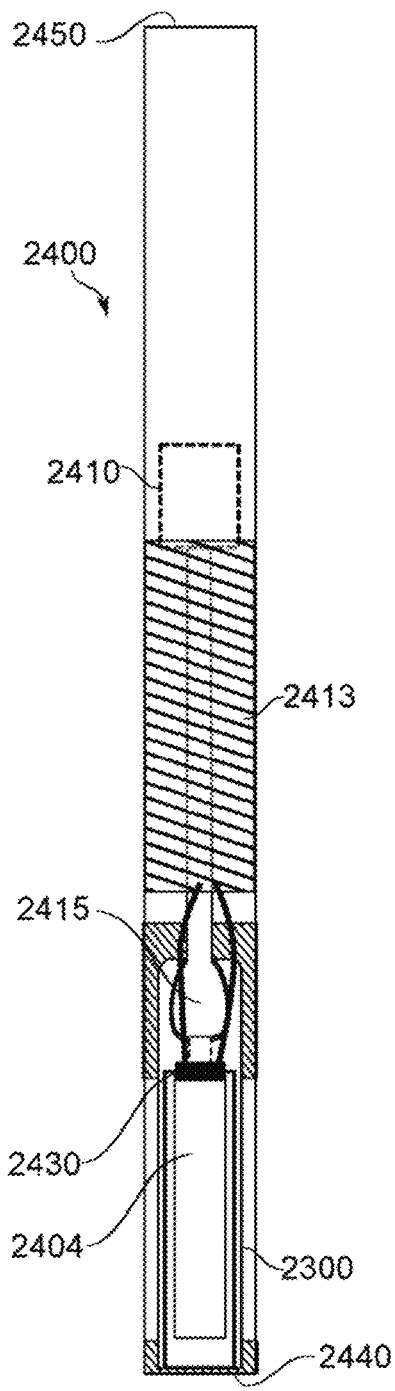
Figure 4B:
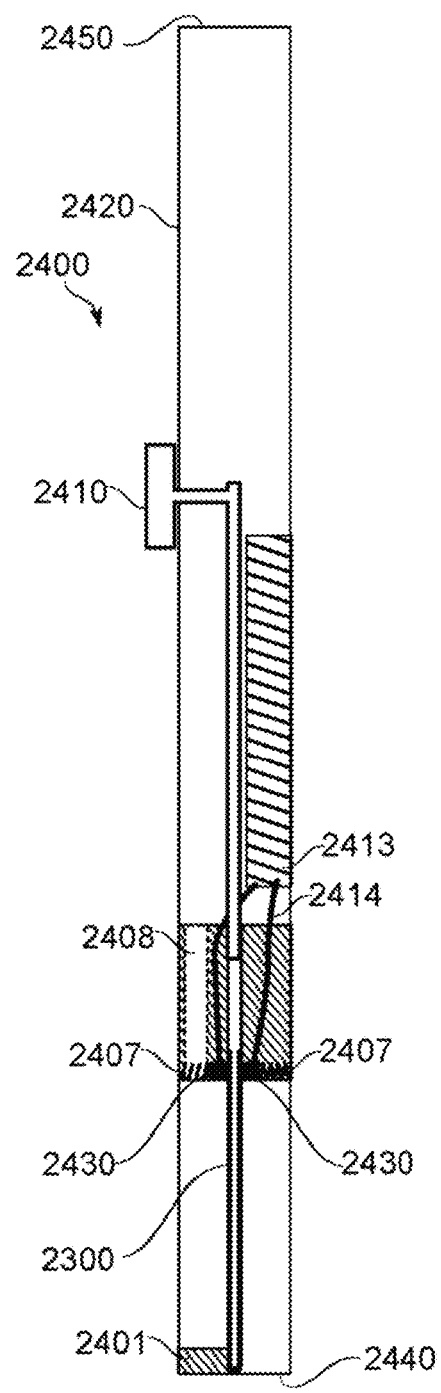
Figure 5:
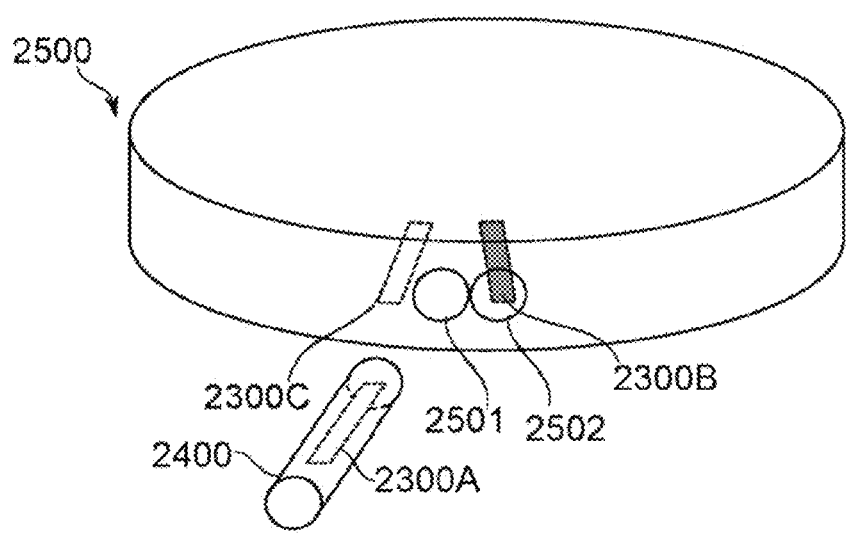
Figure 6:
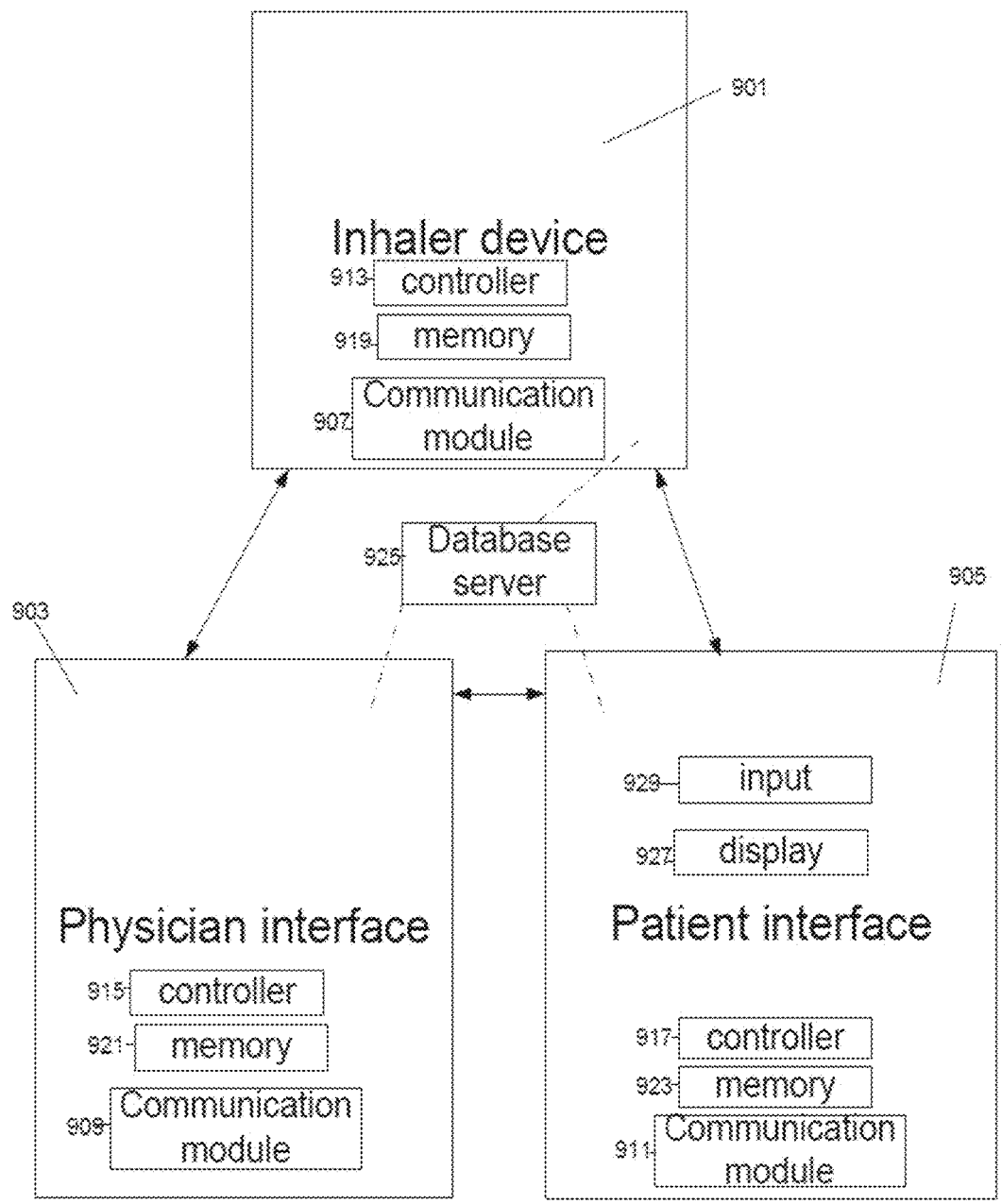
Figure 7:
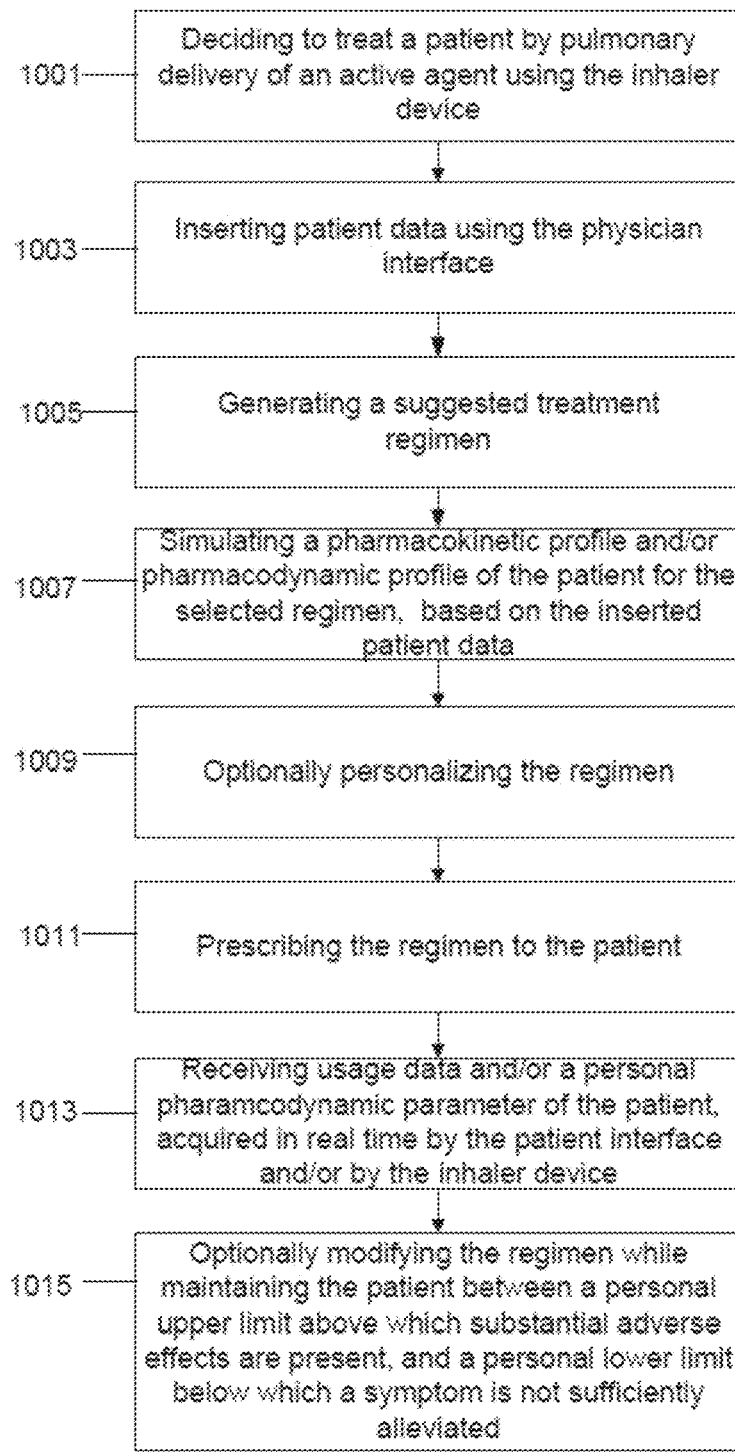
Figure 9:
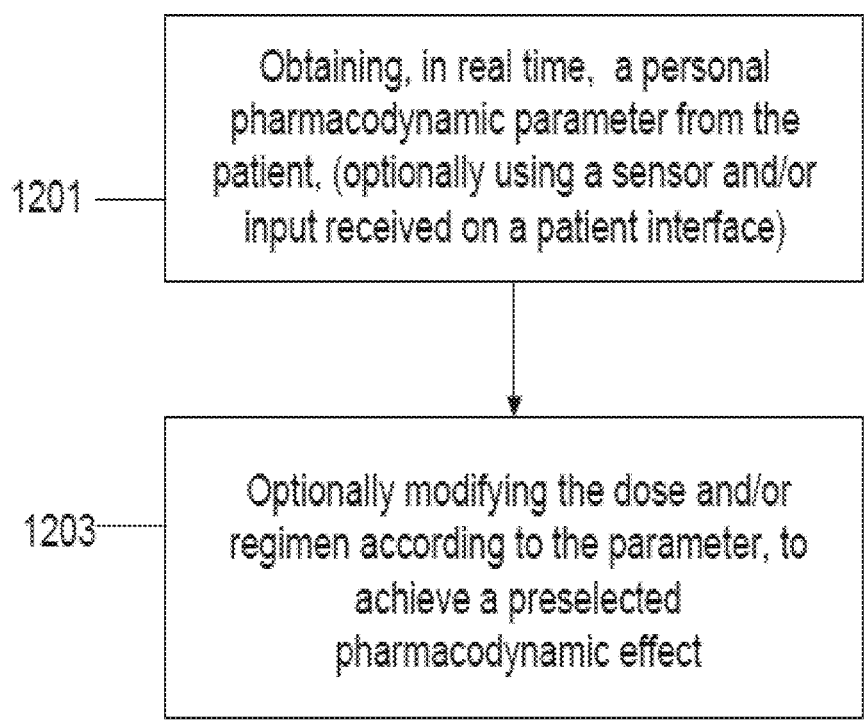
Figure 11:
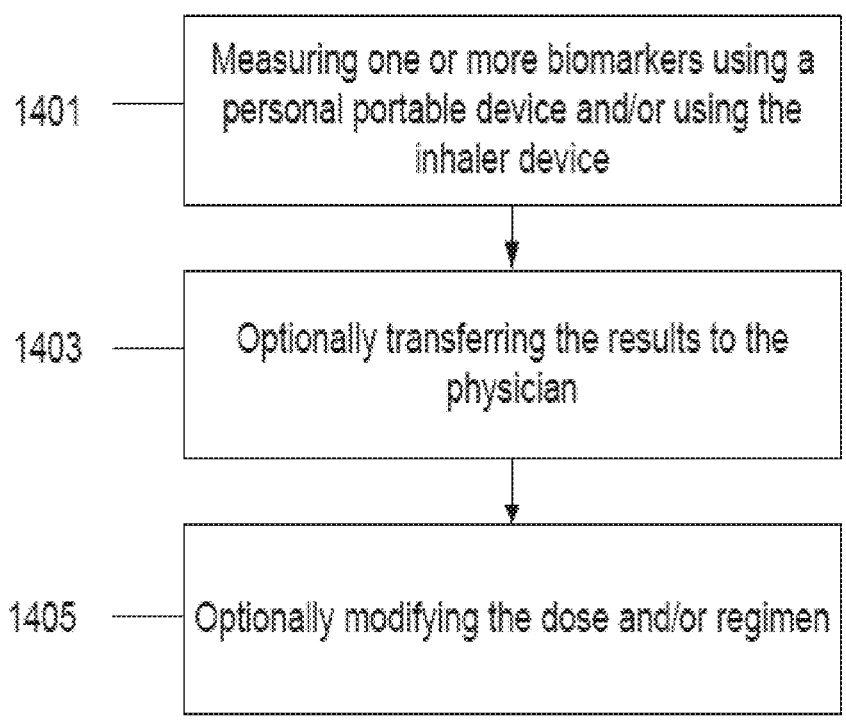
Figure 12:
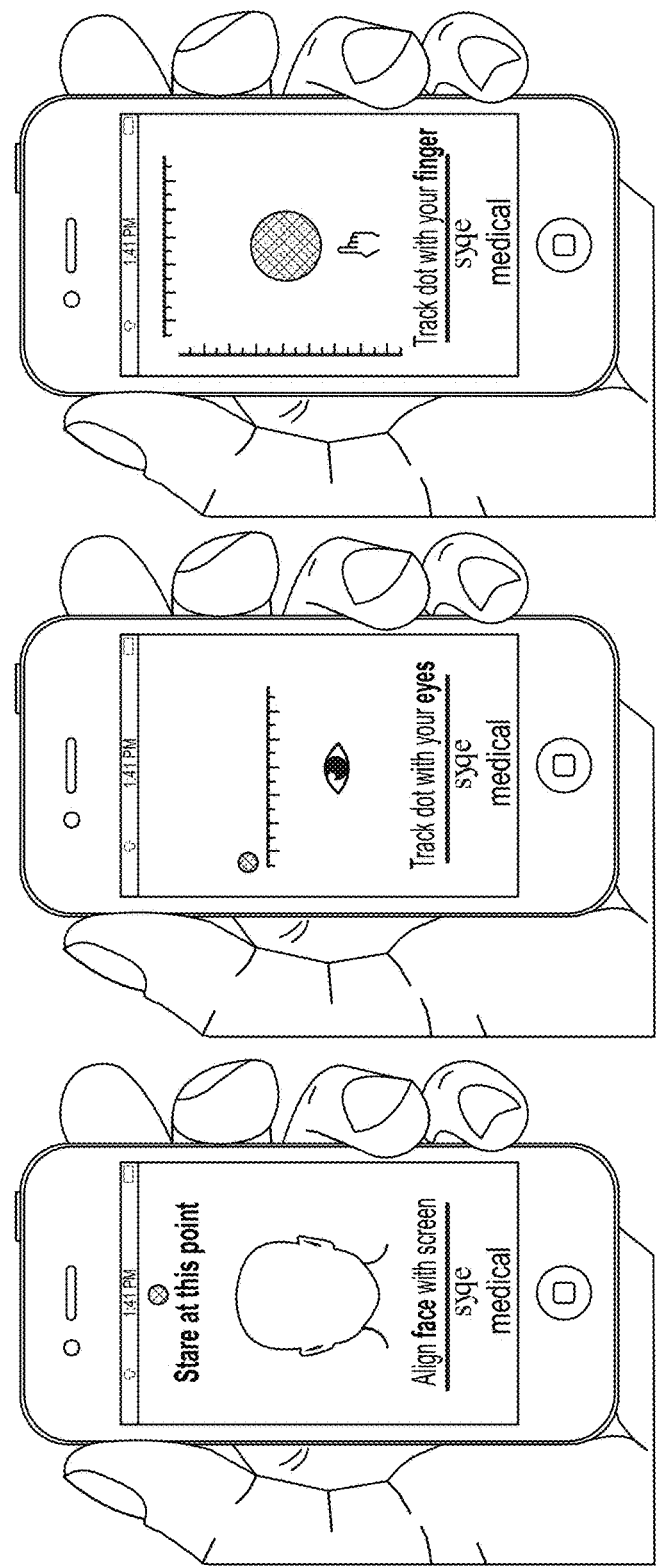
Figure 13:
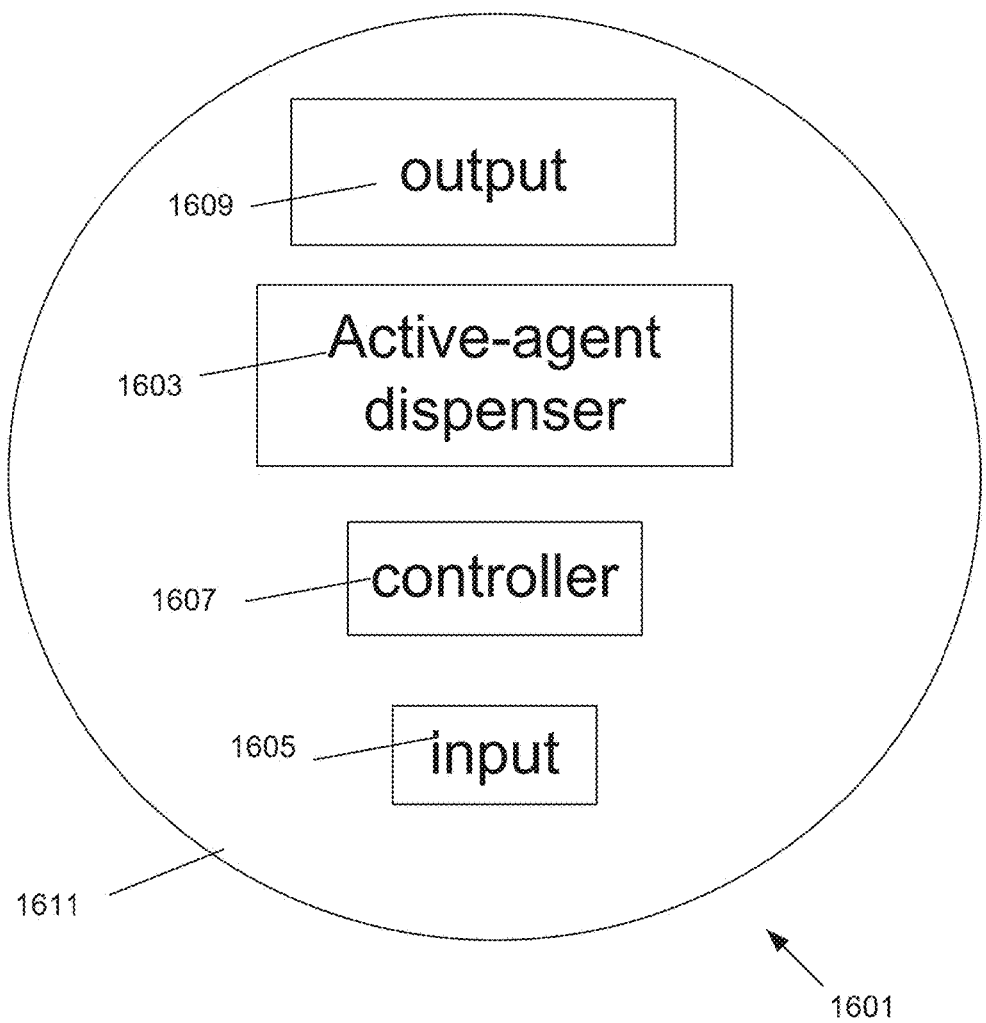
Figure 14A:
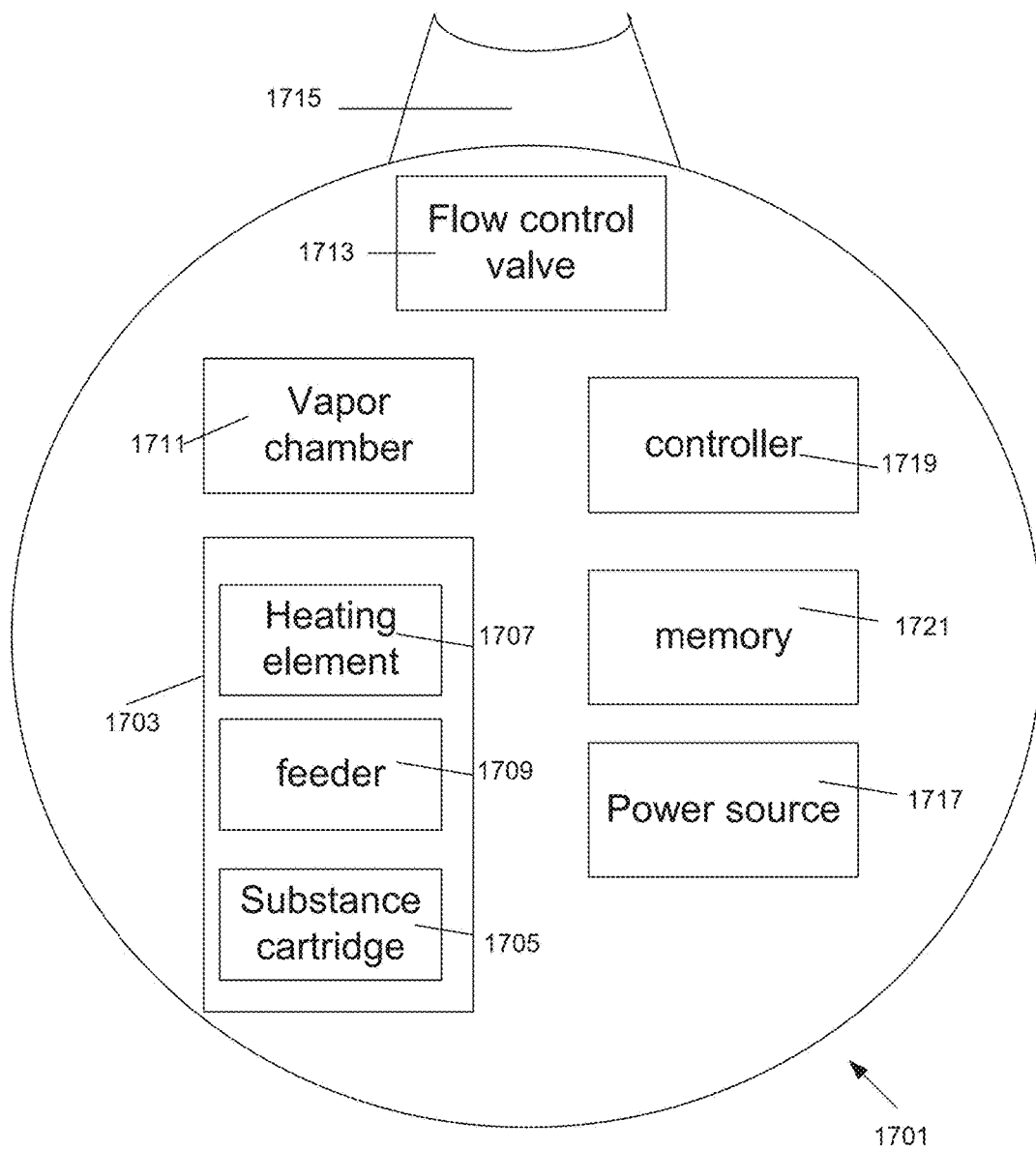
Figure 14B:
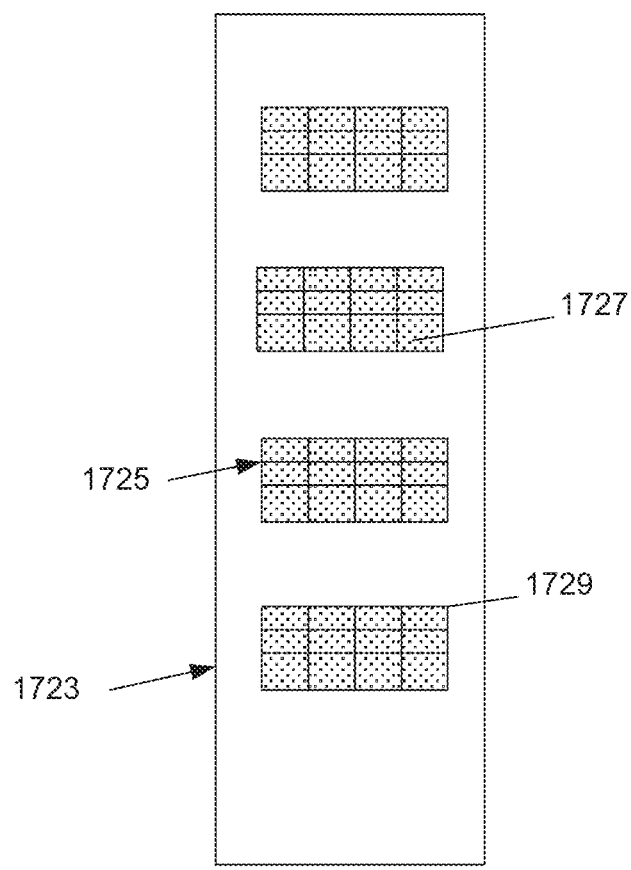
Figure 15:
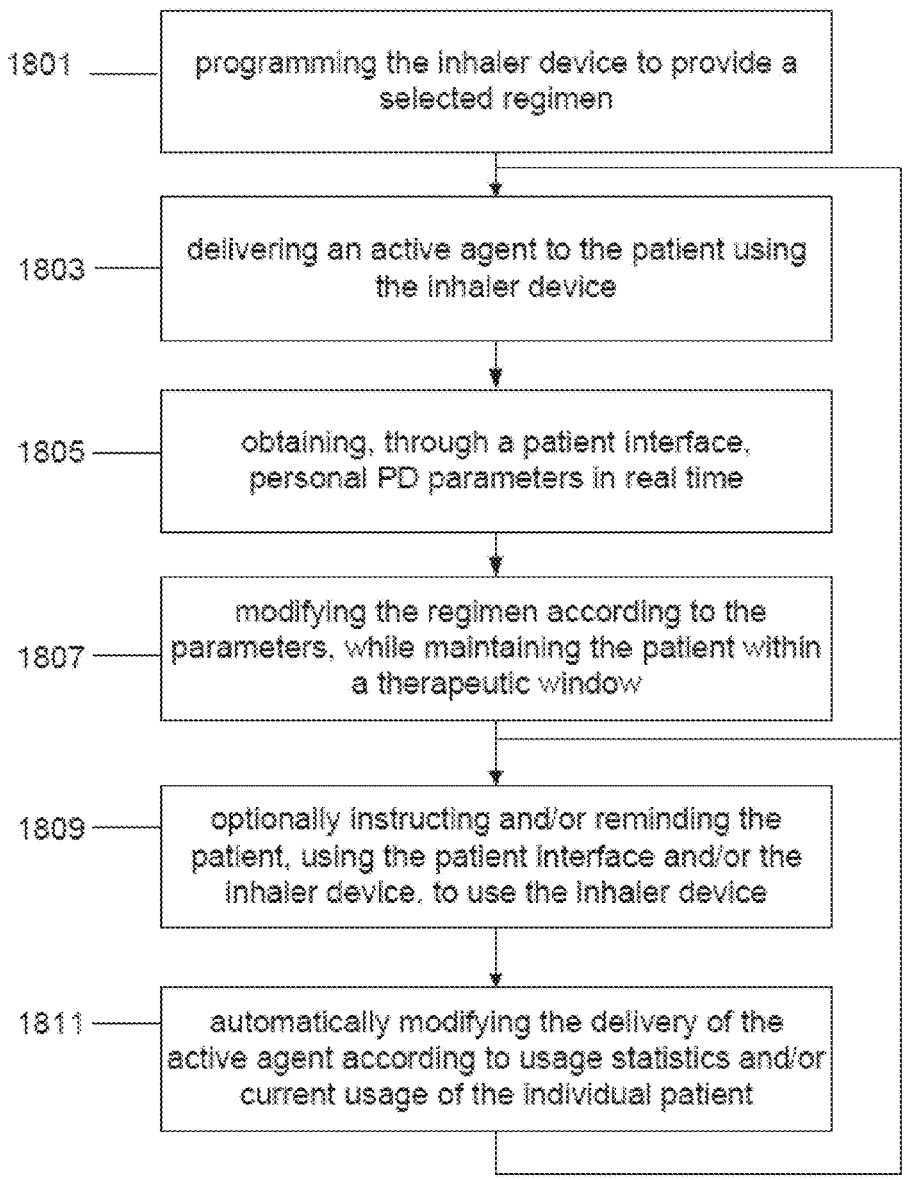

FIGS. 1A-M are schematic views of a dose unit (cartridge), disassembled and assembled, and some alternative constructions thereof, according to some embodiments;

FIGS. 2A-E schematically illustrate a carousel-type dose delivery system for use in or as an inhaler device, according to some embodiments;

FIGS. 3A-B schematically illustrate a clamping chamber apparatus for vaporizing and delivery of a bioactive agent from a dose unit, according to some embodiments;

FIGS. 4A-B schematically illustrate a device for loading from a carousel and separable from the carousel for vaporizing and delivery of an isolate bioactive agent from a dose unit, according to some embodiments;

FIG. 5 schematically illustrates an interlock-protected dose dispensing apparatus, together with a removable dose administration assembly, according to some embodiments;

FIG. 6 is a schematic diagram of a system comprising an inhaler device, a physician interface and/or a patient interface, according to some embodiments;

FIG. 7 is a flowchart of a method for prescribing a personalized regimen to a patient, according to some embodiments;

FIGS. 8A-D are a schematic diagram (FIG. 8A) and print screens (FIGS. 8B-D) of a physician interface for selecting and prescribing a regimen to a patient, according to some embodiments;

FIG. 9 is a flowchart of a method for obtaining a personal pharmacodynamic (PD) parameter from a patient and modifying a regimen accordingly, according to some embodiments;

FIGS. 10A-E are print screens of a patient interface (FIGS. 10A, 10C, 10E), and graphic representations of an expected pharmacodynamic and pharmacokinetic profiles of the patient before and after a personal PD parameter is obtained (FIGS. 10B and 10D respectively), according to some embodiments;

FIG. 11 is a flowchart of a method for obtaining one or more biomarkers using a personal portable device and/or using the inhaler device, and optionally modifying the dose and/or regimen accordingly, according to some embodiments;

FIGS. 12A-C are print screens of a patient interface comprising various applications for obtaining biomarkers and/or for assisting a patient in determining a perceived therapeutic and/or adverse effect, according to some embodiments;

FIG. 13 is a schematic diagram of an inhaler device configured to provide automated controlled pulmonary delivery of one or more active agents, according to some embodiments;

FIGS. 14A-B are a schematic diagram of a configuration of an inhaler device (FIG. 14A), and a dose unit of an inhaler device comprising discrete pallets (FIG. 14B), according to some embodiments; and FIG. 15 is a flowchart of a method of treating an individual patient using a system according to FIG. 9, while maintaining the patient within a personalized therapeutic window, according to some embodiments.

DESCRIPTION OF SPECIFIC EMBODIMENTS OF THE INVENTION

The present disclosure, in some embodiments thereof, relates to pharmacology and, more particularly, but not exclusively, to methods and devices for controlled delivery by inhalation of vaporizable substances.

Before explaining at least one embodiment in detail, it is to be understood that the disclosure is not necessarily limited in its application to the details of construction and the arrangement of the components and/or methods set forth in the following description and/or illustrated in the drawings and/or exemplified by the Examples.

Difficulties associated with controlled delivery by injection and/or ingestion of bioactive (pharmaceutically active) agents which are characterized by low aqueous solubility and/or high viscosity and/or high boiling point, have lead the present inventors to contemplate delivery of such bioactive agents by vaporization and inhalation. As discussed hereinabove, methods and devices for pulmonary (inhalation) delivery of vaporizable bioactive agents from plant substances containing the same have been shown to be highly effective and conducive to widely acceptable pharmaceutical standards and practices. However, these methods and devices have not been designed to deliver isolated bioactive agents, namely agents which no longer form a part of a plant substance.

While searching for a comprehensive solution to the problem of controllably and reproducibly delivering a pre-determined amount of an isolated vaporizable bioactive agent by inhalation, the present inventors have contemplated a dose unit which includes a pallet comprising at least one isolated bioactive agent in and/or on a carrier material, and a heating element in thermal contact with and extending across the pallet, such that the bioactive agent is vaporized from the pallet upon applying a current to the heating element. The dose unit includes an amount of the bioactive agent that corresponds to one or more use cycle (dose), and can be used in an inhaler device which controls heating intensity and duration and/or air flow through the dose unit during inhalation, thereby delivering controllably and reproducibly a pre-determined vaporized amount of the bioactive agent to the subject.

A Method of Vaporization and Inhalation of an Isolate Bioactive Agent:

According to an aspect of some embodiments, there is provided a method of pulmonary delivering by inhalation at least one bioactive agent to a patient, using an inhaler device which is configured for controllably releasing by vaporization of one or more bioactive agents from a dose unit comprising the isolated bioactive agent(s).

This method constitutes a mode of administration by inhalation of a vaporized bioactive agent, which is otherwise difficult to administer by ingestion and/or injection for practical reasons, patient's compliance, and intrinsic properties of some isolated bioactive agents, rendering the same unsuitable or otherwise non-preferable for administration by ingestion and/or injection. Optionally, the method of pulmonary delivering by inhalation at least one bioactive agent to a patient, uses a metered dose inhaler device (MDI device) which is an inhaler device configured for controllably releasing by vaporization at least one pre-determined vaporized amount of the one or more bioactive agents.

According to some embodiments, the term "inhalation" refers to an action effected by a user/patient as a voluntary and intentional breathing-in of ambient air through a device so as to carry a vaporized agent into the lungs. It is noted that according to some embodiments of, spontaneous breathing may also carry the vaporized agent into the lungs, as well as involuntary breathing effected by a mechanical ventilation/respiration device, as such devices are known in the art.

According to some embodiments, the dose unit is meant to comprise a predetermined and pre-measured amount of a bioactive agent or an isolated bioactive agent. In some embodiments, the amount corresponds to a single dose taken occasionally or taken as part of a treatment regimen. In some embodiments, a dose unit is designed to include an amount of an isolated bioactive agent which corresponds to more than a single dose taken occasionally or taken as part of a treatment regimen. The dose unit can therefore include multiple single doses contained separately in the dose unit, or contained combined and vaporized in pre-determined aliquots. The amount of isolated bioactive agent in a single dose may be calculated taking into account an efficiency of vaporization of the bioactive agent.

The term "vaporization" as used herein in all its inflections, refers to a combustionless (non-combustion) process wherein a substance is rendered transportable as a gas (vapors), a mist, droplets thereof suspended in the inhaled atmosphere, or an aerosol. In some embodiments, "vaporization" means that the substance is rendered transportable as a gas (vapors) by heating. In some embodiment, during the delivery by inhalation, the vapors may cool down and condenses to form a mist, namely droplets of the substance suspended in the inhaled atmosphere, or an aerosol thereof. In the context of some embodiments, the term "vaporization" encompasses a phase transition from liquid to gas (evaporation and boiling) as well as a phase transition from solid to gas (sublimation). In some embodiments, the term "vaporization" also includes the intermediate state of partly condensed vapors which form small droplets that are suspended in the inhaled atmosphere to form a mist or an aerosol. According to some embodiments, the term "vaporization" refers to a process wherein an isolated substance is rendered transportable as a gas or droplets thereof suspended in the inhaled atmosphere, namely that the intended substance is essentially the only substance that is being vaporized, devoid of a carrier or any other notable component other than the inhaled atmosphere. According to some embodiments, the term "vaporization" excludes nebulization (conversion of liquids into fine spray of small droplets comprising a plurality of a substance in liquid state, or the conversion of liquids into an aerosol or a mist, also referred to as atomization) as well as other forms of substance transport in the form of fine solid particles comprising a plurality of a substance (powder).

According to some embodiments, the term "vaporization" excludes processes in which a substance is dissolved, suspended, emulsified or otherwise mixed with a liquid carrier, and then rendered transportable in the form of a mist which includes the liquid carrier or an aerosol which includes the liquid carrier.

According to some embodiments, vaporization is effected by heating the substance to a temperature which is sufficient to raise the partial pressure of the vaporized substance while not causing the substance to burn (below its combustion temperature). Typically, vaporization is effected by heating the substance to a temperature just below, equal to or above its normal boiling point at atmospheric pressure. According to some embodiments, vaporization is effected by increasing the temperature of the substance and lowering the ambient pressure (applying negative pressure, or vacuum). Lowering the ambient pressure is typically effected by the inhalation action, which exerts negative pressure in the atmosphere surrounding the substance, normally in the range of 5-50 mbar below relative to atmospheric pressure (negative pressure values, or −5 to −50 mbar).

The term "vaporized amount", as used herein, refers to the amount of an agent that is in vapor form, whereas the vapor form amount is obtained by means of a heating elements in the device, optionally taking into account the removal of vapors by air flow. It is noted herein that in some embodiments the amount of vaporized agent in the context of the present disclosure is not an estimated amount but rather represents the actual amount vaporized upon said heating, as measured directly by standard laboratory methodologies.

The term "pre-determined vaporized amount" refers to an amount that is purposely released by an MDI device from the dose unit, the magnitude of which is determined by design of a dose unit, device settings and/or a regimen protocol, as described herein.

The terms "bioactive agent", "pharmaceutically active agent", "biologically active agent", and "agent" are used herein interchangeably and refer to a compound, a polymer, a drug, a conjugate or a complex, or any combination thereof, which exerts a somatic and/or psychoactive effect when administered to a subject. Typically, the bioactive agent exerts a desired and/or beneficial and/or therapeutic effect upon pulmonary delivering thereof and then via a systemic pathway (e.g., blood, lymph) to a target organ(s) and/or system(s). The agent may be of natural origin or synthetic. Non-limiting examples of active agents include CNS active agents, chemotherapeutic agents, sedative agents, analgesic agents and psychotropic agents.

The term "isolated bioactive agent", as used herein, refers to a bioactive agent which is prepared synthetically, or to a bioactive agent which is extracted from a natural product.

In some embodiments, the term "isolated bioactive agent" refers to a substantially purified substance, as opposed to, for example, a natural product such as a plant substance, which also includes solid insolubles such as cellulosic materials.

The term "isolated bioactive agent" is meant to encompass a whole extraction or a selective extraction of one or more substances extracted from a natural product as a soluble fraction.

In some embodiments, the term "isolated bioactive agent" refers to a soluble fraction of an extracted preparation which is essentially miscible in one or more solvents and/or mixtures of solvents and/or can essentially dissolve therein. By "essentially dissolve" it is meant that at least 90% by mass of the total mass of the isolated bioactive agent is dissolved in one or more solvent(s) without the bioactive agent decomposing, while less than 10%, less than 8%, less than 5%, less that 3% or less than 1% insoluble solid mass is left undissolved in the fraction. By being "essentially miscible" it is meant that at least 90% by mass of the total mass of the isolated bioactive agent is in any form (for example, liquid, resin or soluble powder) that may combine with one or more solvent(s) without the bioactive agent decomposing to form a clear liquid, while less than 10%, less than 8%, less than 5%, less that 3% or less than 1% insoluble solid mass is left undissolved in the fraction. In the context of some embodiments, an isolated bioactive agent is substantially devoid of, or has less than 10%, less than 8%, less than 5%, less that 3% or less than 1% by mass of an insoluble substance, of an insoluble fraction or of an insoluble component. The term "insoluble" refers to a substance that is not soluble in a solvent or a mixture of solvents in which the isolated bioactive agent is soluble.

In some embodiments, the amount of the isolated bioactive agent which is capable of being dissolved in one or more solvent(s) is at least 90%, 91%, 92%, 93%, 94%, 95%, 96%, 97%, 98% or 99% by mass of the total mass of the isolated bioactive agent.

In some embodiments, the "isolated bioactive agent" refers to or includes a bioactive agent which can be vaporized essentially without leaving a substantial residue. By "vaporized essentially without leaving a substantial residue" it is meant that at least 50% by mass of the total mass of the bioactive agent is vaporized without decomposing, while less than 50% by mass is left unvaporized. In some embodiments, the amount of the bioactive agent which is capable of being vaporized essentially without decomposing and without leaving a substantial residue, is at least 50%, 60%, 70%, 80%, 90%, 95% or 99% by mass of the total mass of the bioactive agent.

In the context of some embodiments, an isolated bioactive agent is substantially devoid of a non-vaporizable substance, a non-vaporizable fraction or non-vaporizable component. The term "non-vaporizable" refers to a substance or a mixture of compounds that does not significantly vaporize at the conditions (e.g. temperature) used to vaporize at least 50% of the isolated bioactive agent and/or that de-composes or combusts before boiling or otherwise forming vapors thereof and/or having a boiling temperature higher than the temperature used to vaporize at least 50% of the isolated bioactive agent.

According to some embodiments, the isolated bioactive agent is a product of an extraction process which has been isolated from other substances without further purification. In some embodiments, the content of the isolated bioactive agent in an unpurified extract by mass is at least 20%, at least 30%, at least 40%, at least 50%, at least 60%, at least 70%, at least 80%, at least 90%, at least 95%, or at least 98%, relative to the mass of the unpurified extract comprising the isolated bioactive agent.

According to some embodiments, the isolated bioactive agent is a product of an extraction process or a product of a synthetic process, which has been isolated from other substances and purified. In some embodiments, the purity of an isolated bioactive agent is at least 90%, at least 95%, or at least 98% pure in terms of mass, relative to the mass of the sample comprising the isolated bioactive agent.

According to some embodiments, the term "isolated bioactive agent" refers to a combination of bioactive agents, each of which may exert different or similar effects and/or have a synergistic effect when combined (cumulative effects of each alone is lower than the effect of the combination).

According to some embodiments, "whole extraction" refers to a process wherein a natural product is processed so as to allow the soluble fraction of its constituents to dissolve in a particular solvent, whereas water may extract an aqueous fraction, and an organic solvent or inert gas may afford an organic fraction.

A "selective extraction" is a process wherein a whole fraction or whole extraction is further processed in a variety of steps and solvents to afford a paste, a resin or a powder comprising essentially one or more substances which are selected by virtue of their solubility in selected solvents, thereby affording a selective extraction that consists essentially of a few selected major components (two, three, four, five, six, seven, eight, nine or ten substances or compounds), referred to herein as a "co-extract".

A whole extract and/or a co-extract and/or a single extracted and purified substance may each be turned into an isolated bioactive agent by substantially removing (e.g., by evaporation) the solvent(s), thereby affording an isolated bioactive agent possibly as a liquid resin or a dried powder comprising the respective solvent-soluble substances.

For example, while a sample of a naturally occurring, cultivated or bred plant may comprise one or more bioactive agents as well as a plurality of various other plant-born substances and insoluble substances, a sample of an isolated bioactive agent may consist mostly of one substance or compound, and a co-extracted sample of isolated bioactive agents may consist mostly of a few (two, three, four, five, six, seven, eight, nine or ten) substances or compounds which are the major components of the sample, whereas minor components and impurities constitute less than 40%, less than 30%, less than 20%, less than 10%, less than 9%, less than 8%, less than 7%, less than 6%, less than 5%, less than 4%, less than 3%, less than 2% or less than 1% of the sample in terms of mass.

In embodiments where the bioactive agent in prepared synthetically, the reaction product may comprise the bioactive agents mixed with a plurality of various reactants, side-reaction products, solvent(s) and other substances, and thus a sample of an isolated bioactive agent is further processes and purified to consists essentially of one desired substance or compound, whereas impurities constitute less than 10%, less than 9%, less than 8%, less than 7%, less than 6%, less than 5%, less than 4%, less than 3%, less than 2% or less than 1% of the sample in terms of mass.

In the context of some embodiments, an isolated bioactive agent is substantially devoid of a solvent, an insoluble matter or a carrier, namely it is not in a solution, an emulsion or a suspension, and not mixed with other substances, unless is it combined with other isolated bioactive agents, all of which are meant to be co-delivered, regardless if some are dissolved or suspended or found in an emulsion with any other isolated bioactive agent(s).

In embodiments where more than one isolated bioactive agents are combined, the combination is encompassed by the term "isolated bioactive agent" is defined herein, wherein each of the bioactive agents is intended for pulmonary co-delivery thereof to a patient. As used herein, the term "co-delivery" means that two or more bioactive agents are delivered to a patient in a single inhalation step and/or are present in and/or on a single dose unit.

The term "pure", as used herein, refers to the amount of a single identified and defined substance, relative to the total amount of a mixture of the substance with other substances, which is more than 90%, 91%, 92%, 93%, 94%, 95%, 96%, 97%, 98%, more than 99%, more than 99.5%, more than 99.9% or 100% of the total mass of the mixture.

Isolated bioactive agents, according to some of the embodiments presented herein, include, without limitation:

a synthetically prepared and purified (95% pure) bioactive agent;

a combination of two or more individually synthesized and purified (95% pure each) bioactive agents;

a naturally occurring bioactive agent or combination of more than one bioactive agents that is extracted from a microorganism, a plant or an animal, and further purified to about 90% purity (a purified extract);

a whole/full extract of a microorganism, a plant or an animal, which is fractioned in an aqueous solution or an organic solvent (whichever the bioactive agent or combination of bioactive agents is more soluble in), dried and used without further purification;

a selective extract of a microorganism, a plant or an animal, which is fractioned successively in various aqueous and organic solutions in order to achieve further isolate one or more bioactive agents from some components of the extract, dried and used without further purification;

a combination of more than one purified, whole or selective extracts, each comprising one or more bioactive agents;

a combination of one or more synthetically prepared and purified bioactive agents with one or more purified, whole or selective extracts, each comprising one or more bioactive agents.

The method disclosed herewith addresses the problem of controllably and reproducibly administering some types of bioactive agents using some of the most prevailing and accepted modes of administration, such as ingestion and intravenous/subcutaneous injection. For example, hydrophobic bioactive agents which are substantially immiscible in aqueous media and/or physiological fluids, may exhibit low absorption, low distribution and low bioavailability when administered by ingestion or injection. As known in the art, the likelihood of a compound to be found suitable as a drug increases if the compound exhibits some degree of solubility in aqueous media; the "Lipinski's rule of five" refers to the octanol-water partition coefficient (log P) and state that the compound should exhibit a log P of less than 5, wherein compounds exhibiting log P greater than 5 are considered too hydrophobic for most modes of drug administration, resulting in poor absorption and distribution thereof in the body. It is noted herein that embodiments of the present disclosure are not limited to hydrophobic bioactive agents, and therefore isolated bioactive agents having a log P of less than 5 are also contemplated. For example, in some embodiments the isolated bioactive agent(s) have a log P greater than 1.

The devices and methods presented herein are useful for administering any isolated bioactive agent which can be vaporized, regardless of its hydrophobicity, including agents exhibiting high log P values. According to some embodiments, the isolated bioactive agent has a log P value at the temperature range of 20-37° C. greater than 3, greater than 4, greater than 5, greater than 6, greater than 7 or greater than 8.

The devices and methods presented herein are useful for administering hydrophobic isolated bioactive agents, as the agent is vaporized and delivered by inhalation as a gas (vapors of the agent).

Another factor that limits the use of some isolated bioactive agents is their physical form, namely being a thin or a viscous liquid or a solid in their isolated form.

It is contemplated that the devices and methods presented herein are useful for administering any isolated bioactive agent which can be vaporized, regardless of its physical form, including agents which are viscous liquids. According to some embodiments, the isolated bioactive agent has a viscosity of at least 10 centipoise (cP), at least 20 cP, at least 30 cP, at least 40 cP, at least 50 cP, at least 60 cP, at least 70 cP, at least 80 cP, at least 90 cP, at least 100 cP, at least 200 cP, at least 300 cP, at least 400 cP, at least 500 cP, at least 1000 cP, at least 2000 cP, at least 5000 cP or more than 10,000 cP.

The methods and devices presented herein are suitable for vaporizing a wide range of isolated bioactive agents, including those having a relatively high boiling point. According to some embodiments, the isolated bioactive agent has a boiling point higher than 80° C., higher than 100° C., higher than 150° C., higher than 200° C., higher than 250° C., higher than 300° C., higher than 350° C., higher than 400° C., higher than 450° C., higher than 500° C., higher than 550° C., higher than 600° C., higher than 650° C., higher than 700° C. or higher than 750° C.

The methods and devices presented herein are suitable for vaporizing a wide range of vaporizable isolated bioactive agents, regardless of its physical form, hydrophobicity, viscosity and/or boiling point, as long as it is vaporizable. The term "vaporizable", as used in the context of some embodiments, refers to a property of a substance that defines its suitability to be pulmonary delivered by vaporization and inhalation. This property corresponds with the boiling or sublimation temperature of the substance, which can range from 80° C. or even 100° C. to 750° C.

According to some embodiments, the isolated bioactive agent which is delivered effectively to the patient at a pre-determined and reproducible therapeutic amount, is a sticky, thick, viscous and oily (hydrophobic, log P more than 5) liquid having a relatively high boiling point, in vapor phase without co-administering, intentionally or inadvertently, any excipient, carrier or any other non-active or undesirable substance therewith.

As known in the art, members of the family of plants referred to as cannabis contain a variety of vaporizable bioactive agents which have been found to exert beneficial therapeutic activity in humans. According to some embodiments, the bioactive agent is, or includes a cannabinoid extracted and purified from cannabis or a synthetically prepared and purified cannabinoid. According to some embodiments, the isolated bioactive agent is an isolated cannabinoid such as, for example, Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV), cannabitriol (CBT) and any isomer and/or combination thereof.

It is note that other vaporizable isolated bioactive agents are contemplated within the scope of the present disclosure, including without limitation, naturally occurring bioactive agents from extracts or synthetic origin such as salvinorin, cathinone, pukateine, thujone, damianin, bulbocapnine, kavalactones, lagochilin, lactucarium, glaucine, ergine, ibogaine, aporphine and leonurine, and synthetic vaporizable isolated bioactive agents such as atropine, buprenorphine, butorphanol, fentanyl, hydromorphone, methadone, midazolam, nalbuphine, naloxone, naltrexone, oxycodone, phenytoin, remifentanil, rizatriptan, sildenafil, sufentanil and zolpidem.

According to some embodiments, the isolated bioactive agent includes co-extracts or synthetic combinations of bioactive agents comprising terpenes, flavonoids, nitrogenous compounds and other naturally occurring and synthetic compounds. For example, some combinations of cannabinoids, terpenes and flavonoids have been shown to modulate the effect of a cannabinoid or even exert a synergistic effect compared to the effect of the cannabinoid by itself.

Terpenes and terpenoids include, without limitation, Δ3-Carene, β-Selinene, β-Pinene, β-Phellandrene, β-Famesene, β-Caryophyllene, β-Pinene, β-Eudesmol, α-Terpinolene, α-Pinene, α-Phellanderene, α-Humulene, α-Bergamotene, α-terpineol, α-Terpinene, α-Pinene, α-Humulene, α-Guaiene (t), α-Cedrene, α-Bisabolol, Valencene (t), trans-Ocimene, trans-Ocimene, trans-Caryophyllcnc, Terpinolene, t-2-Pinanol (t), Selina-3,7-(11)-diene, Selina-3,7(11)-diene (t), Sabinene Hydrate, Nerol, Myrcene, Myrcene, Menthol, Linalool, Limonene, Limonene, Isoborneol, Guaiol, Guaia-1(10), 11-diene (t), Germacrene B (t), Geraniol, Farnesene (t), Eudesm-7(11)-en-4-ol (t), Elemene (t), cis-Ocimene, cis-Ocimene, CaryophyllEne oxide, Caryophyllene oxide, Camphor, Camphene, Borneol and (+)Fenchol.

Flavinoids include, without limitation, cannflavine A, cannflavine B, cannflavine C, vitexin, isovitexin, apigenin, kaempferol, quercetin, luteolin and orientin.

According to some embodiments, the bioactive agent is an isolated isomer of any one of the abovementioned cannabinoids, such as, for example, (−)-trans-Δ$^9$-tetrahydrocannabinol, also known as dronabinol, which is an isomer of THC. Isolated dronabinol, like other isomers of THC, exhibits water solubility of 0.0028 mg/mL at 23° C., a log P value of 5.648, a boiling point of 157° C. and a viscosity of 85-140 cP.

A Dose Unit:

Due to the chemical and physical properties of some vaporizable isolated bioactive agents, the method of administration by inhalation of such bioactive agents is effected by use of a customized dose unit, also referred to herein interchangeably as a cartridge, which is designed and configured to allow vaporization and inhalation of at least one bioactive agent to a user (e.g., a patient). As discussed hereinabove, the bioactive agent may be, in some embodiments, an isolated bioactive agent characterized by one or more properties which render its administration less effective or even inoperable by ingestion and/or injection to a user.

According to an aspect of some embodiments of, a unit dose is provided for pulmonary delivery of at least one bioactive agent to a user, which includes a pallet and an electrically resistive heating element, also referred to herein interchangeably as resistive heating element (e.g., a metal resistive heating element), in thermal contact with and extending across at least a portion of a surface of the pallet, wherein the pallet comprises a solid carrier material and a pre-determined amount of the bioactive agent is in and/or on the carrier material.

In some embodiments, the resistive heating element extends across at least two opposite surfaces of the pallet.

Figure 1A:
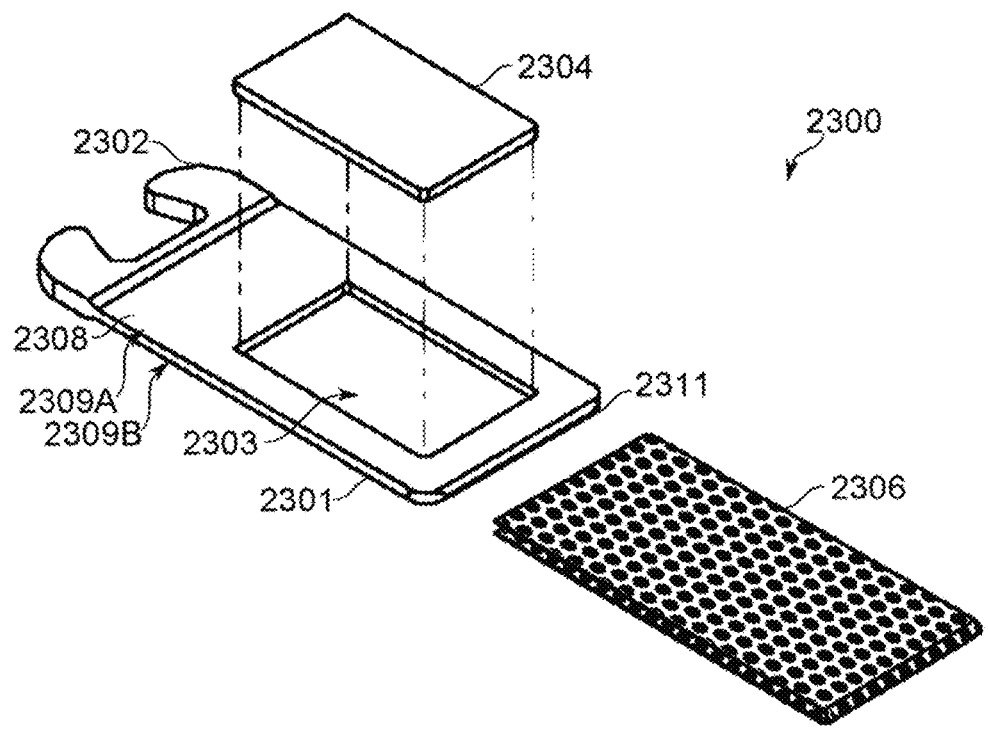
Figure 1B:
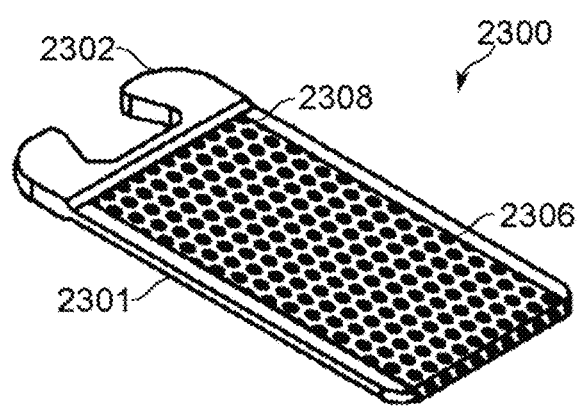
Figure 1C:
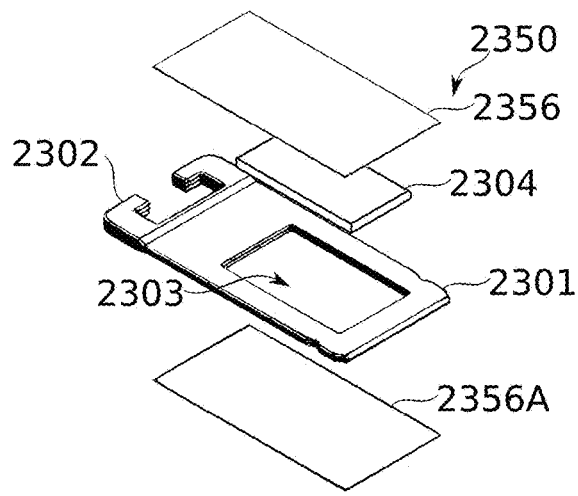
Figure 1D:
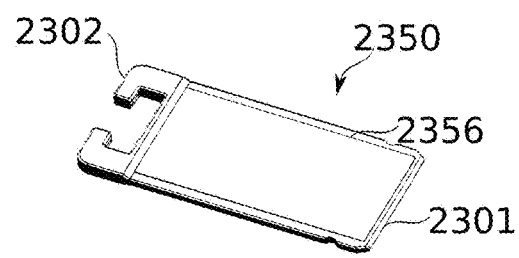
Figure 1E:
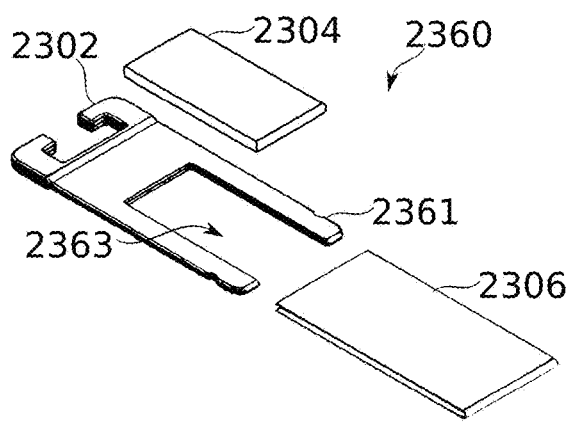
Figure 1F:
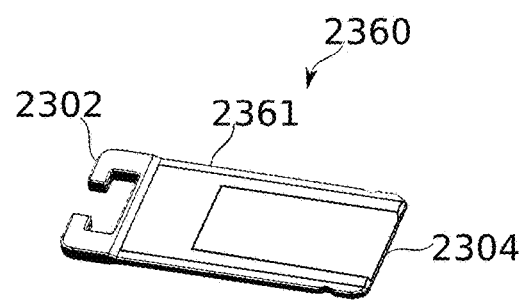

FIGS. 1A-B present schematic illustrations of a dose unit (dosing substance vaporization cartridge, or cartridge), according to some embodiments, showing dose unit 2300 having pallet 2304 fitting into aperture 2303 in frame 2308 which forms a part of housing 2301 (FIG. 1A), and resistive heating element 2306 in thermal contact with and extending across at least two opposite surfaces of pallet 2304 (FIG. 1B). FIGS. 1C-M provide schematic illustrations of alternative constructions of dose units, according to some embodiments.

The term "pallet", as used herein, refers to a composition-of-matter constituting a matrix or a platform for handling, holding, storing, dispensing and delivering a substance which otherwise is too dispersible to be handled, contained, dispensed and/or delivered by itself (e.g. a liquid, a paste, fine powder, particulate, or a sticky resin). A pallet, for example, allows the dispensing of a thick liquid, and further allows vaporization and subsequent delivery thereof from the pallet.

Optionally, the liquid, paste or sticky resin dry out and/or otherwise become solid after inclusion in the pallet. According to some embodiments, a pallet includes any substance that is left behind and not delivered to the patient upon applying heat thereto.

According to embodiments, the pallet comprises a solid carrier material which is selected and designed to allow vaporization and inhalation of an isolated bioactive agent therefrom. Since the carrier material is used to carry and dispense the vaporizable bioactive agent, it is defined by several chemical and physical criteria, which include one or more of:

being substantially unreactive (chemically inert) with respect to the bioactive agent when in contact therewith, at least within a temperature range as low as the lowest expected storage temperature and up-to the operational temperature, possibly with some greater range of confidence (e.g. between 50° C. below a storage temperature and up-to about 50° C. above an operational temperature). According to some embodiments, the storage temperature may be as low as about −80° C., or about −40° C. or about −20° C., however, higher and lower temperatures are contemplated within the scope of the present disclosure, including, for example room temperature (e.g. 18-26° C.). The carrier material is chemically inert in temperatures of up-to (at least) the maximal temperature of vaporization of the bioactive agent (or slightly higher, for example, by 50° C.), or up-to the combustion and/or decomposition temperature of the bioactive agent, however, higher temperatures are contemplated within the scope of the present disclosure;

having a combustion and/or decomposition and/or melting temperature higher than the combustion/decomposition of the bioactive agent, however, carrier materials with higher combustion and/or decomposition and/or melting temperature are contemplated within the scope of the present disclosure;

having a thermal conductivity of at least 0.1 W/mK (allowing the carrier to readily disperse heat throughout the pallet); and having an electric resistivity of at least 10 μΩ·m (reducing the capacity of the carrier to short-cut the current passing through the restive heating element).

As a composition-of-matter comprising the carrier material and the bioactive agent (the loaded pallet), the loaded pallet is substantially air-permeable. In other words, the loaded pallet is characterized by a structure that allows a flow of the inhaled gas (typically ambient atmosphere, whether carrying vapors of the agent or not) to pass therethrough. According to some embodiments, the structure of the pallet is characterized by passage of the inhaled gas therethrough, whereas passage is defined by at least 2 liter of gas per minute (l/min), at least 1.5 l/min, at least 1 l/min, at least 0.8 l/min or at least 0.5 liter of gas per minute, under a pulling vacuum of at least 1-5 kPa, which corresponds to the pulling force exerted by pulmonary intake of air into the lungs of the user, whereas the average pulmonary peak in a healthy adult human is about 25 mbar. According to some embodiments, the structure of the pallet is characterized such that is allows a minimal flow of 0.5 liter per minute and a maximal negative (pulling) pressure of 25-40 mbar or negative pressure of 1-5 kPa (−1 to −5 kPa) near the pallet.

In order for the pallet to be air-permeable, it can for example be formed as a unified porous matrix or comprises a plurality of tightly or loosely packed individual porous and/or non-porous particles. In some embodiments where the pallet is made of a plurality of individual (unfused) particles, it is typically enclosed by walls having apertures in two opposite surfaces to allow gas flow therethrough, hence the articles are larger than the apertures.

According to some embodiments, the structure of the pallet is characterized by a surface/mass ratio of at least 1000 square meters per gram ($m^2$/g).

According to some embodiments, the structure of the pallet is characterized by a surface/volume ratio of at least 500 square meters per milliliter ($m^2$/ml).

More specifically, the term "carrier material", as used in the context of some embodiments, is a solid pallet material which provides a physical support for a vaporizable bioactive agent, or a heat-vaporizing substance, which is incorporated in the pallet.

According to some embodiments, the bioactive agent is not applied on the electrically resistive heating element, but rather applied in and/or on the carrier material. In some embodiments the bioactive agent and the resistive heating element are not in direct physical contact, but are in thermal contact via at least the pallet.

In some embodiments, the carrier material, or a pallet comprising the same, is characterized by at least one of the following properties:
chemical compatibility and acceptability;
relatively high combustion/decomposition/melting temperature;
physical unity, homogeneity and wholeness;
porosity;
high thermal conductivity; and
low electric conductance.

In the context of some embodiments, chemical compatibility and acceptability may be regarded as a requirement for substantial chemical stability and inertness, cleanness and lack of extractable and leachable substances, and mechanical integrity.

The carrier material is required to be chemically stable and inert (unreactive) with respect to the bioactive agent and the components comprising the inhaler dose unit (cartridge) provided herein as well as other components of the inhaler device, at least in the full range between storage conditions and operating conditions of the device and the cartridge. In some embodiments, chemical inertness is also required during a process of manufacturing the pallet and/or the dose unit, such as being stable and chemically inert during contact with polar and/or non-polar solvents which may be used in the process and/or in temperature ranges or other conditions applied during manufacture. Chemical stability and inertness may be defined by percentage of carrier material or constituents thereof which undergoes chemical or physical change during process, storage and use of the cartridge provided herein, and/or the amount of carrier material-derived substances (referred to herein as "extractables and leachables") which is allowed to be inhaled during the use of the dose unit provided herein, according to Pharmacopoeia and other commonly used standards and practices known and available to any skilled artisan. A skilled artisan would be able to comply with the foregoing, following commonly practiced guidelines, as provided, for example, in the publications provided publically by the Product Quality Research Institute (PQRI); in textbooks such as "*Leachables and Extractables Handbook: Safety Evaluation, Qualification, and Best Practices Applied to Inhalation Drug Products*", 2008, Editors: Douglas J. Ball, Daniel L. Norwood, Cheryl L. M. Stults, and Lee M. Nagao, Publisher: John Wiley & Sons, Inc.; and in scientific peer-reviewed articles such as "*Best practices for extractables and leachables in orally inhaled and nasal drug products: an overview of the PQRI recommendations*" by Norwood, D. L. et al., *Pharm Res.*, 2008, 25(4), p. 727-39.

The carrier material is further selected to be resistant to heat at the temperature at which the bioactive agent vaporizes or a slightly higher temperature. In other words, the carrier material is selected to exhibit a combustion, decomposition and/or melting temperature higher than the temperature used in the preparation of the dose unit and higher than the temperature at which the dose unit is used to vaporize the bioactive agent during inhalation. For example, in embodiments using a bioactive agent having a boiling point of about 250° C., the carrier material is selected such that it is chemically and mechanically stable when heated to the temperature used to vaporize the bioactive agent, thus the carrier material is selected having a combustion temperature and/or decomposition temperature and/or melting temperature higher than 250° C., higher than 270° C., higher than 290° C., higher than 300° C., higher than 320° C., higher than 350° C., higher than 400° C., higher than 450° C., higher than 500° C., higher than 600° C., higher than 700° C. or higher than 750° C. For example, quartz, glass, ceramic materials and some organic and inorganic polymers have a combustion temperature and/or decomposition temperature and/or melting temperature higher than the bioactive agent boiling point of about 250° C.

According to some embodiments, the carrier material is made of one or more of the substances that include, without limitation, glass, quartz, ceramic composite, silicon carbide, mullite, alumina, carbon species (such as carbon-black, activated carbon, graphene, graphite, fullerenes and the likes), silicone and polytetrafluoroethylene.

The physical unity, homogeneity and wholeness requirement corresponds to the chemical acceptability in the sense that the carrier material is selected such that it maintains physical and mechanical integrity (none-brittle and non-crumble) to the extent that it can be handled and used to prepare the pallet in the dose unit provided herewith. In other words, the carrier material is selected such that is does not break or crumble to particles which are non-homogeneous in size and shape and in particular smaller than the intended carrier material particle size (see the porosity requirement below) when being processed into a pallet during preparation or during use of the inhaler dose unit. Carrier materials can thus be selected according to brittleness, ductility and ductile-brittle transition temperature properties, as these are known and available to any skilled artisan in the field of material science, while considering the stress which is applied to the carrier material during the process of preparing the dose unit presented herein, and the temperatures which the carrier material in the dose unit is exposed to during use thereof, as discussed herein.

The air permeability, the porosity of the carrier material, or a characteristic of a pallet comprising the same, is defined, according to some embodiments, in terms of the flow of air that can be passed though the pallet under an inhalation pressure when having a bioactive agent applied on and/or in the carrier material. Thus, the carrier material is selected suitable for forming a pallet that allows an air flow of at least 0.5 liter of gas in a minute (0.5/min) or even 1 l/min under a pulling vacuum of at least 1-5 kPa when having a predetermined amount of a bioactive agent applied thereon or therein. In some embodiments the carrier material is in a form of a plurality of particles having a shape that allows gas to flows therebetween when packed into a pallet, as described herein. In some embodiments, the particles of the carrier material are in the shape of beads or spheroids. It is noted that spheroid-shaped particles are more easily manipulate during the process of preparing the dose unit provided herein.

Particles of the carrier material in the shape of fibers, foil or any other shape that can be packed into an air-permeable pallet are also contemplated. In some embodiments, the particles of the carrier material are larger than the hole size in an air-permeable retaining mesh or a woven mesh comprising the electrically resistive heating element (e.g., a metal resistive heating element) forming a part of the dose unit, e.g., larger than 10 microns, 15 microns, 20 microns, 25 microns, 30 microns, 35 microns, 40 microns, 45 microns, or larger than 50 microns.

In some embodiments, the carrier material is in the form of a single monolithic air-permeable matrix constituting the pallet. The air-permeable matrix can be formed by fusing carrier material particles in a process typically referred to as sintering, and/or by any other methodology for forming solid foams and other air-permeable matrices within the knowledge of a skilled artisan.

The carrier material making the pallet is selected so as to have a thermal conductivity which is conducive to allowing efficient and homogeneous heating and vaporization of the bioactive agent applied thereon or therein. The thermal conductivity of the carrier material is therefore higher that the thermal conductivity of paper and other plant-derived dried material, such as cannabis floss, which is about 0.01 W/mK. For example, the thermal conductivity of the carrier material is at least 0.1 W/mK, at least 0.2 W/mK, at least 0.3 W/mK, at least 0.4 W/mK, at least 0.5 W/mK, at least 0.6 W/mK, at least 0.7 W/mK, at least 0.8 W/mK, at least 0.9 W/mK, at least 1 W/mK, at least 5 W/mK, at least 10 W/mK, at least 20 W/mK, at least 50 W/mK, or at least 100 W/mK. For example, carrier material comprising silicone cast resin exhibits thermal conductivity of about 0.15-0.32 W/mK, carrier material comprising polytetrafluoroethylene (PTFE) exhibits thermal conductivity of about 0.25 W/mK, carrier material comprising glass exhibits thermal conductivity of about 1 W/mK, carrier material comprising quartz exhibits thermal conductivity of about 3 W/mK, and carrier material comprising Cr/Ni steel (18% Cr, 8% Ni) exhibits thermal conductivity of about 16.3 W/mK.

According to some embodiments, the carrier material is other than (not a) natural plant material, other than natural and chemically unprocessed plant material and other than natural and mechanically unprocessed plant material. According to some embodiments, the carrier material is devoid of natural chemically unprocessed and/or natural mechanically unprocessed plant material. For example, paper may be defined as a chemically and mechanically processed plant material, while pieces of a plant material pressed into a pallet are regarded in the context of the present disclosure as chemically unprocessed plant material.

The carrier material making the pallet is selected so as to have low electric conductance or high resistivity so as to avoid current passing therethrough instead of through the integrated resistive heating element or the resistive mesh. For example, the carrier material is selected to exhibit resistivity higher than 1 $\mu\Omega \cdot m$ at 20° C., which is about the resistivity of nichrome alloy used in the electrically resistive heating element. Hence, the resistivity of the carrier material is at least 10 $\mu\Omega \cdot m$, at least 50 $\mu\Omega \cdot m$, at least 100 $\mu\Omega \cdot m$, at least 200 $\mu\Omega \cdot m$, at least 400 $\mu\Omega \cdot m$, at least 600 $\mu\Omega \cdot m$, at least 800 $\mu\Omega \cdot m$, or at least 1000 $\mu\Omega \cdot m$ (1 $m\Omega \cdot m$). For example, carrier material comprising polytetrafluoroethylene (PTFE) exhibits resistivity of about $10^{23}$-$10^{25}$ $\Omega \cdot m$, carrier material comprising glass exhibits resistivity of about $10^{11}$-$10^{15}$ $\Omega \cdot m$, and carrier material comprising fused quartz exhibits resistivity of about $7.5 \times 10^{17}$ $\Omega \cdot m$.

According to some embodiments, the carrier material can be formed from substances such as, but not limited to, glass (in the form of a plurality of individual beads or sintered/fritted air-permeable glass matrix or derived from a sol-gel precursor), quartz (in the form of a plurality of individual beads or fused air-permeable quartz matrix), a ceramic composite comprising, e.g., silicon carbide (SiC), alumina ($Al_2O_3$) and/or mullite ($Al_2O_3$—$SiO_2$) (in the form of a plurality of individual beads or a fused air-permeable ceramic matrix or an air-permeable ceramic composite matrix), high-melting polymer, e.g., PTFE or silicone resins (in the form of a plurality of individual polymer beads or an air-permeable fused polymeric matrix or an emulsion-templated/derived polymeric foam matrix). According to some embodiments, the carrier material can be formed from a liquid crystal polymer (LCP), polyether ether ketone (PEEK), Ultem, Teflon, Torlon, Amodel, Ryton, Forton, Xydear, Radel, Udel, Polypropylene, Propylux, Polysulfone, or another polymer material.

It is noted that the material forming the housing which provides mechanical support for the pallet according to some embodiments (for example, support for pallet 2304 by enclosure within aperture 2303 in frame 2308 of housing 2301 in FIG. 1A; for details see below), is selected with some criteria which follow the selection of the carrier material, such as the criterion for chemical acceptability, the criterion for relatively high combustion/decomposition/melting temperature and the criterion for low electric conductance. Other criteria which apply for the selection of a carrier material, such as physical unity, homogeneity and wholeness, porosity and high thermal conductivity, are less relevant or not required for the selection of the housing material.

The amount of the bioactive agent which is applied in and/or on the carrier material in the pallet corresponds to the pre-determined vaporized amount of the isolated bioactive agent(s) which is to be pulmonary delivered to the patient/user, according to some embodiments, namely since the reservoir of the vaporized agent is the pallet, it contains the agent in an amount sufficient to allow vaporization and delivery of the desired vaporized and inhaled amount thereof. The amount of the agent in the pallet may range from 20 to 500 mg, from 10 to 200 mg, from 9 to 150 mg, from 8 to 100 mg, from 7 to 50 mg, from 5 to 20 mg, from 1 to 10 mg, from 10 to 70 mg, from 10 to 60 mg, from 12 to 50 mg, from 12 to 40 mg, from 15 to 40 mg, from 12 to 30 mg or from 12 to 25 mg.

A Cartridge Assembly:

In some embodiments, the isolated bioactive agent vaporizes at a temperature requiring a substantial exogenous heat input to reach a temperature above ambient temperature. In some embodiments, the time to reach a volatilizing temperature is, for example, about in a range between about 1000 msec-5 sec, for example, 250 msec, 500 msec, 1000 msec, or another greater, smaller, or intermediate value.

In some embodiments, the heating element comprising the dose unit or cartridge is a resistive heating element comprising a metal, for example nichrome, FeCrAl, cupronickel and/or stainless steel. Optionally, the heating element is packaged in thermal contact with the pallet. Thermal contact comprises, for example, being in direct contact, or in contact across a heat-transmitting layer allowing a high rate of thermal transfer (for example, comprised of a high heat conductance material such as copper, aluminum, brass or steel; and/or having a thin-walled construction of less than about 10 μm, 20 μm, 25 μm, 50 μm, or another greater, lesser or intermediate thickness). In some embodiments, thermal contact comprises sufficiently close apposition of pallet and heating element that the pallet subtends substantially the whole thermal radiating angle of the portion of the heating element overlying it; for example, more than 90%, 95%, 99%, or another greater, lesser or intermediate value. In some embodiments, the peak current applied to the electrode is in the range of about 1-10 Amperes; for example, about 1 Amperes, 2 Amperes, 4 Amperes, 6 Amperes, or another higher, lower, or intermediate current.

In some embodiments, the thermal contact comprises the heating element extending across and in contact with one or more surfaces of the pallet, for example, one side, or two opposite, largest surface-area sides of the pallet. In some embodiments, the thermal contact comprises the heating element being at least partially embedded within the pallet.

In some embodiments, the heating element is air-permeable (allows the passage of air therethrough). In some embodiments, the pallet is air-permeable. Air-permeability is under conditions, for example, of the passage of air at ambient temperature through a heated assembly of pallet and heating element under a suction pressure (pulling force) such as a suction pressure generated by inhaling, and/or a positive pressure generated from a side away from the inhaling side of the cartridge.

In some embodiments, the applied pressure is in the range of 4-20 mmHg (about 5-30 mbar), 10-25 mmHg, 5-30 mmHg, 25-40 mmHg, 30-50 mmHg, or another range having the same, higher, lower, and/or intermediate bounds.

In some embodiments, the heating element comprises a bend of about 180 degrees, such that the element is formed into a clip- and/or U-shape that encloses the pallet on at least two sides. Optionally, each of the two sides of the pallet is in thermally conductive contact with a surface of the heating element. Optionally, the heating element on the cartridge is positioned so that there is no self-contact between the two sides of the U-shape. Optionally, application of current to the heating element by a dose heating assembly is to or near the two ends (comprising contact-receiving regions) of the U-shape, such that heating may occur on two sides of the pallet at once. In some embodiments, application of current to the heating element is by connection to a contact-receiving region on either side of the pallet on one or both sides of the cartridge. The heating element is optionally divided into two or more parts, each receiving current independently. Alternatively, the heating element is provided as a single piece (optionally, a piece which entirely encloses the pallet); electrodes being applicable to contact-receiving regions of the element such that a voltage potential is generated over the extent of the heating element in thermal contact with the pallet.

An aspect of some embodiments relates to the provision of a frame along with the pallet and heating element. In some embodiments, the frame comprises an aperture for receiving the pallet (a dose chamber). In some embodiments, the surface area over the width and length of the dose chamber is in the range of about 20-100 $mm^2$; for example, about 25 $mm^2$, 50 $mm^2$, 66 $mm^2$, 80 $mm^2$, 100 $mm^2$, or another greater, smaller, or intermediate surface area. In some embodiments, the aperture region is open on one side. Optionally, the open side of the aperture region is closed by the application of a U-shaped heating element.

In some embodiments, the frame aperture dimensions are, for example, about 6×10 mm, the frame defining a volume about 1 mm thick. Optionally, the aperture area is in the range of about 20-100 $mm^2$; for example 20 $mm^2$, 40 $mm^2$, 50 $mm^2$, 60 $mm^2$, 80 $mm^2$, or another greater, lesser, or intermediate face area. The aperture is optionally shaped substantially as a square (for example, about 8×8 mm); optionally the aperture is oblong (for example, rectangular) with a side ratio of, for example, 1:2, 1:3, 1:4, 1:10, or another larger, smaller, intermediate or inverted ratio of side lengths. Optionally, the aperture is, for example, about 30×2 mm in dimension. In some embodiments, the aperture is round, oval or having any shape and dimensions within the frame.

In some embodiments, the frame having the aperture performs one or more of the following functions:

- positions the pallet at a reproducible position relative to the overall dimensions of the cartridge;
- provides mechanical stability to the pallet (for example, support at the edges, rigidity to resist bending, and/or anchoring);

provides latching/anchoring elements and/or surfaces enabling the transport of the cartridge by mechanical elements shaped to interact with the cartridge;

provides insulation between two parallel sides of the heating element to prevent self-contact; and/or provides surface region and/or bulk volume region for adherence/anchoring/embedding of the heating element with the cartridge.

In some embodiments, general functions of the aperture include shaping of the dose structure during manufacture, and/or assistance in manipulation of the dose for administration.

In some embodiments, the frame comprises a polymer or ceramic which is substantially heat resistant (for example, non-burning, non-melting, dimensionally stable) at the temperature of volatilization. In some embodiments, the polymer comprises, for example, a liquid crystal polymer (LCP), polyether ether ketone (PEEK), Ultem, Teflon, Torlon, Amodel, Ryton, Forton, Xydear, Radel, Udel, Polypropylene, Propylux, Polysulfone, or another polymer material.

In some embodiments, a latching/anchoring element comprises a transport arm interlock region, shaped for attachment to the transport arm of a dose puller or other dose transport mechanism.

In some embodiments, the pallet is closed within in the assembled cartridge by the heating element extending across the aperture. In some embodiments, the heating element extends across the aperture without itself closing the aperture (for example, a ribbon heating element is provided having gaps between windings of the ribbon). In some embodiments another element is provided which acts as a containment barrier (or wall). Optionally, the containment barrier is positioned over the heating element and pallet together, and/or between the heating element and the pallet.

An aspect of some embodiments relates to a process of manufacturing a dose unit, as described hereinabove, in the form of a pallet and a heating element positioned within a frame.

In some embodiments, the process includes contacting the carrier material with the bioactive agent;

forming a pallet comprising the carrier material having the bioactive agent applied therein and/or thereon; and covering the pallet on at least one side by the electrically resistive heating element.

As discussed hereinabove, the pallet can be in the form of a plurality of individual particles or in the form of a unified air-permeable matrix, and in each of these alternatives, the carrier material is contacted with the bioactive agent(s) by way of dipping in, spraying with and/or coating the carrier material with the bioactive agent(s) or otherwise applying the bioactive agent(s) on the carrier material.

Application of the bioactive agent(s) may be carried out before, during and/or after a pallet is produced. When a plurality of isolated bioactive agents is applied, they may be applied simultaneously and/or in sequence.

The application of the bioactive agent(s) can be carried out for example using a liquid form of the bioactive agent, either as an isolated (pure) liquid or a solution of the bioactive agent which can be a dissolved liquid or a dissolved solid. When using a solution of the bioactive agent(s), the process may further include drying-off the solvent of the solution so as to leave a coating of the isolated bioactive agent in and/or on the carrier material or part thereof.

In some embodiments, the process of forming the pallet made of a plurality of particles includes placing the plurality of particles of the carrier material having the isolated bioactive agent(s) applied therein and/or thereon within a dose chamber on a planar surface;

vibrating the planar surface until the plurality of particles is leveled; and pressing the leveled plurality of particles so as to form the pallet.

In some embodiments, the process of forming the pallet made of a unified air-permeable matrix includes cutting a section from the carrier material to form the unified air-permeable matrix. In embodiments where the carrier material is cut from a larger piece of material, the bioactive agent(s) can be applied thereon prior to or subsequent to cutting the material.

In some embodiments, the process of forming the pallet made of a unified air-permeable matrix includes pressing a plurality of particles of the carrier material in a mold having the inverse shape of the final pallet so as to unify the particles into an air-permeable matrix, whereas such process may be referred to as fusing or sintering. In such cases the application of the bioactive agent(s) is performed after the pressing step.

In some embodiments, a measured amount of particles of the carrier material having a measured amount of the isolated bioactive agent applied thereon, referred to as loaded carrier material, is placed in a dose chamber. In some embodiments, the measured amount of loaded carrier material is in the range, for example, of about 1-100 mg. In some embodiments, the dose chamber is sized such that the extent of the pallet, upon formation, is limited by bounds of the dose chamber, for example, bounds of pallet width and length.

In some embodiments, the measured amount of loaded carrier material is leveled by vibration of the dose chamber. Optionally, the vibrating is with an amplitude in the range of about 0.1-1.2 mm; for example 0.5 mm. The frequency of vibration is, for example, in the range of about 20-300 Hz (such as 30 Hz, 45 Hz, 60 Hz, 75 Hz, or another higher, lower, or intermediate frequency). Duration of shaking is, for example, chosen from within the range of 100-1100 msec (such as about 300 msec, 400 msec, 500 msec, 800 msec, or another longer, shorter, or intermediate time). Optionally, the chamber is secured before vibration, to prevent the loaded carrier material from escaping the chamber from underneath.

In some embodiments, the pallet is formed from the leveled loaded carrier material by compression by a pressing element. In some embodiments, the loaded carrier material is compressed to a pallet of thickness within a range of between about 200-1500 µm, or thickness within another range having the same, larger, smaller and/or intermediate bounds.

An "Empty" Dose Unit:

An aspect of some embodiments relates to the provision of a frame along with the pallet and optionally also a heating element without a bioactive agent incorporated therein. In some embodiments, the dose unit is prepared essentially as described herein apart for the application of a bioactive agent in/on the pallet of the dose unit. Once a bioactive agent in incorporated in/on the pallet of such an "empty" dose unit, the "filled" dose unit can be used for pulmonary delivery of the bioactive agent essentially as described herein.

In some embodiments the empty dose unit can be filled for example by directing a spray or drip to the pallet within the dose unit. Optionally this is performed when the heating element is removed or before its attachment. In some embodiments the bioactive agent is applied throughout the dose unit, including the heating element and/or the frame. Optionally in such cases, the frame (and possibly also the heating element) are made of or comprise materials that are likely to repel or otherwise have a low tendency to maintain contact with the bioactive agent in wet and/or dried form.

In some embodiments, the empty dose unit can be filled by removing the pallet from the frame of the dose unit, applying an isolated bioactive agent on and/or in the pallet as described herein, and reattaching the pallet to the frame. Optionally, the pallet is detached from the heating element so as not to apply the bioactive agent on the heating element while incorporating there bioactive agent in/on the pallet.

Dose Unit Dispenser and Activation:

An aspect of some embodiments relates to positioning and activation of a dose unit carrying the pallet with integrated heating element within a chamber which activates the heating element while confining the vaporizable isolated bioactive agent to a substance delivery channel, and thus relate to an activation unit for positioning and activation of a dose unit.

In some embodiments, the positioning is by movement of the cartridge along a track (for example, by a cartridge transport mechanism). In some embodiments, the chamber comprises a structure which encloses the cartridge on either side to seal it within a defined lumen, and makes electrical contact with a heating element of the cartridge. Optionally, electrical contact is on either side of the cartridge. Optionally, electrical contact is made on sides of the cartridge at points defined by the positioning of the cartridge relative to electrodes of a vaporizing apparatus. Optionally, contact pads extend from the heating element for the making of electrical contact therewith.

An aspect of some embodiments relates to a cartridge container for use with a substance vaporizer which is alternately:

attached to the cartridge container for receipt of a dose unit (a cartridge) into the substance vaporizer; and detached from the cartridge container for dose administration.

In some embodiments, the detachable substance vaporizer is used as part of an interlock mechanism for control of the dispensing of dose units. For example, in some embodiments, the substance vaporizer is used as part of the activation of an interlock which prevents extraction of a new dose unit until a previously spent cartridge is returned to a dispensing container.

Illustration of Some Examples

Different embodiment examples of the listed elements are described herein, as well as examples of embodiments of assembled substance dose units which lack at least one of these elements. It is to be understood that the different element embodiments are optionally combined in embodiments of assembled dose units in other combinations as well (for example, any heating element design provided with any frame design).

Reference is now made to FIGS. 1A-B, which are schematic views of a dose unit 2300 (dosing substance vaporization cartridge), disassembled and assembled, according to some embodiments. Reference is also made to FIGS. 1C-M, which illustrate schematically alternative constructions of dose units 2350, 2360, 2370, 2380, 2390, and 2395, according to some embodiments. FIGS. 1C, 1E, 1G, 1J, and 1L show disassembled dose units, while FIGS. 1D, 1F, 1H, 1K, and 1M show assembled dose units.

In some embodiments, dosages of an isolated bioactive agent are assembled upon and/or within a dose unit 2300. Optionally, dose unit 2300 comprises:

pallet 2304, optionally formed, for example, by flattening, for rapid vaporization;

mechanical support for pallet 2304 (for example, support by enclosure within aperture 2303 in frame 2308 of housing 2301, which is optionally frame shaped);

means for facilitating transport of dose unit 2300 (for example, latch mandibles 2302); and/or means for vaporizing pallet 2304 (for example, resistive heating element 2306).

Optionally, the dose unit is disposable. Potential advantages of a disposable dose unit include: containment of bioactive agent residue for disposable; close integration of dosage support and transport for reliable dosage transport within a dosing apparatus; and/or reduced need to maintain and/or monitor portions of the dosing system (such as a vaporizing heating element) which are subject to conditions that could degrade performance over time.

Optionally, the dose unit is for use in a single inhalation. Potential advantages of a single-use dose unit include improving the precision and/or reliability in controlling the vaporized amount of the bioactive agent under inhaler settings.

For example, the concentration and/or dispersal of an isolate bioactive in the loaded carrier material may be controlled during manufacture at some degree of precision. In general, the degree of variation in the output of the device (e.g., the amount of vaporized and inhaled bioactive agent) may be maintained within a tolerance of less than +/−15% of the intended output. Other factors that may have an effect on variations in the device's output include ambient conditions, user's use habits and user's current condition.

In some embodiments, dose unit 2300 comprises a housing 2301 having aperture or receiving chamber 2303. Optionally, housing 2301 comprises a flattened and elongated strip, while receiving chamber 2303 comprises an aperture framed by the strip (frame 2308). During preparation of dose unit 2300, pallet 2304 is inserted into receiving chamber 2303. Optionally, the pallet is formed before or during insertion such that it conforms to the flattened shape of receiving chamber 2303. It is a potential advantage for the pallet to be held in a flattened format, since a greater surface area and/or a more uniform thickness potentially allow faster and/or more evenly distributed heating and/or air flow during vaporization and delivery.

In some embodiments, the pallet dimensions are, for example, about 6×10 mm across the exposed surface area, and about 1 mm thick. Optionally, the thickness of the pallet is in the range of about 0.1-1.0 mm, or a greater, lesser, or intermediate thickness. Optionally, the face area of the pallet is in the range of about 20-100 mm$^2$; for example 20 mm$^2$, 40 mm$^2$, 50 mm$^2$, 60 mm$^2$, 80 mm$^2$, or another greater, lesser, or intermediate face area. The pallet is optionally formed into a square or substantially square pallet (for example, about 8×8×1 mm); optionally the pallet is oblong with a side ratio of, for example, 1:2, 1:3, 1:4, 1:10, or another larger, smaller, or intermediate ration of side lengths. Optionally, the pallet is, for example, about 30×2× 0.5 mm in dimension. Corresponding pallet by weight is about 15 mg in some embodiments. In some embodiments, the pallet weight is selected from within a range of about 1-100 mg, or another range having the same, larger, smaller, and/or intermediate bounds.

It is a potential advantage to surround pallet 2304 with a framing housing 2301 for greater mechanical stability. For example, a pallet potentially comprise individual particles of loaded carrier material, such that pallet 2304 is liable to shed particles, particularly if moved or bent. Enclosure within cartridge frame 2308 allows pallet 2304 to be moved within the system without applying stresses directly to pallet 2304 itself. In some embodiments, the overall length and width of the cartridge is about 20×10 mm, or another larger, smaller, or intermediate size. During manufacture, a framing housing is a potential advantage for formation of a pallet of the correct size for fitted occlusion of a conduit through which air flows to pick up volatiles released during heating of the pallet.

Figure 1G:
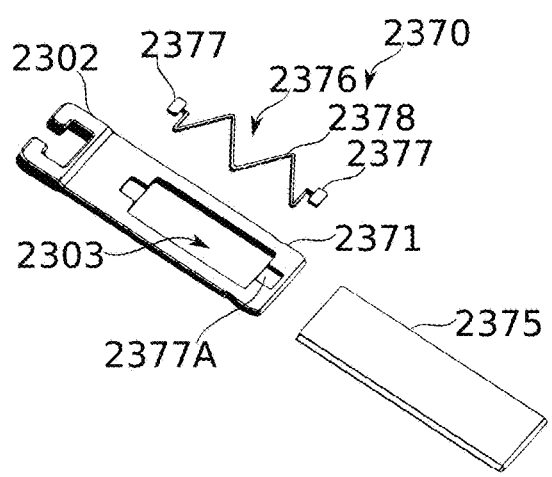

It is to be understood that completely surrounding the pallet is not required, in some embodiments, to achieve sufficient mechanical stability. For example, in some embodiments (see, e.g., FIGS. 1E-F), pallet 2304 is placed in an open-sided chamber 2363 defined by a "U" shaped frame portion 2361. Potentially, this allows packing pallet 2304 into the dose unit 2360 from the open side of frame portion 2361. Potentially, the "U" shaped frame simplifies and/or speeds molding and/or release of the frame itself during manufacture. In some embodiments, the open side is closed off, for example, by a structure such as resistive heating element 2306, a permeable overlay 2375 (optionally a retaining mesh; FIG. 1G), or another structure.

In some embodiments, other support of a pallet is provided. A completely frameless example is shown, for example, in dose unit 2390A of FIG. 1L, where the whole extent of frame 2391A (optionally including even latch mandible 2392) is provided by the pallet material. In some embodiments, pallet material is sufficiently stable when prepared that no or relatively little additional mechanical support is required for use (for example, the pallet is compressed so that it remains intact during transport between a magazine and a clamping chamber). Optionally, at least a portion of the pallet material is mixed with a binder to add stability. Optionally, the pallet is a one piece pallet having sufficient stability, and which serves to hold a gel, fluid or powder comprising the active agent(s).

In some embodiments, a one-piece pallet/frame is formed, optionally with a plurality of pallet materials, for example, a frame material for the region of frame 2391A (which may or may not comprise active substance), and a carrier material containing active agent for release in pallet region 2394A. Optionally, the one piece pallet/frame is formed is formed from a single material but the active agent(s) is added thereto only in pallet region 2394A. Additionally or alternatively, the conditions of formation (for example, degree of compression packing) are different between the framing portion of the pallet, and the bioactive substance releasing portion of the pallet. In some embodiments, the carrier material covers, for example, about 60 mm$^2$ near the center of the pallet 2393. A carrier material is an active containing material that is positioned at a location in a dose unit in association with the heating element such that it may be heated. In some embodiments, a heating element 2306 also provides mechanical support. Optionally, the pallet/frame assembly 2393 in turn provides electrical insulation between parts of the heating element 2306. Attachment between heating element 2306 and pallet 2393 is, for example, by using any method known in the art that would remain stable during use, including, for example, one or more of welding, glue, cold press, hot press and/or pins.

In some embodiments (for example, dose unit 2395 in FIG. 1M), a pallet 2399 is provided with perforations 2398 which increase its permeability to flow. This is of particular potential benefit for frameless or nearly frameless dose unit embodiments. Pallet 2399 of dose unit 2395, for example, is bounded only by latch mandible 2396 (which may be formed as an integral part of the pallet) and (transparently drawn) "U" shaped heating element 2306. Potentially, carrier material with sufficient density to achieve mechanical self-stability reduces the airflow permeability of the resulting pallet, thus interfering with drug volatilization. Perforations 2398 are provided, for example, by introducing gaps with the tooling (a mold, for example) used in packing the carrier material, by perforating the pallet after formation, or by another method.

In some embodiments, (dose unit 2390 in FIGS. 1J-K), the mandibles 2391 are provided as a separate part (for example, manufactured of polymer or metal), attached to a pallet 2394 of carrier material comprising the active agent to be released. In some embodiments, a heating element 2306 or another wrapping structure provides additional mechanical support. Optionally, attachment of pallet 2394 to mandibles 2391 comprises use of an adhesive. Optionally, attachment comprises mechanical interconnection; for example, one of the mandibles 2391 and pallet 2394 is formed with a tab, and the other with a slot, and/or the mandibles 2391 are provided with protrusions (for example, a comb of spikes) around which the pallet 2394 is formed.

In some embodiments (e.g. the cross section of dose unit 2380 shown in FIG. 1I), a heating element 2386 which wraps pallet 2304 is welded at a join 2381 where two sides of the heating element come together. Potentially, this provides an advantage for providing additional mechanical stability to pallet 2304 (and particularly, for one of the frameless or partially frameless embodiments). Since the weld 2381 changes the electrically conductive topology of the heating element 2386, electrodes 2331 for providing heating energy to the heating element 2386 are optionally placed at opposite sides of the heating element (optionally, but not necessarily, in contact with the weld region 2381 itself).

In some embodiments, vaporization of an isolated bioactive agent comprises heating by resistive heating element 2306 or other form of resistive heating element. The resistive mesh optionally comprises a material which displays substantial resistive heating; for example, nichrome (typical resistivity of about 1-1.5 μΩ·m), FeCrAl (typical resistivity of about 1.45 μΩ·m), stainless steel (typical resistivity of about 10-100 μΩ·m), and/or cupronickel (typical resistivity of about 19-50 μΩ·m). According to the choice of material (e.g., metal), parameters such as heating element length and width, thickness, aperture size and/or aperture pattern are adjusted to comprise a total resistance across the resistive heating element which is, for example, in the range from about 0.05-1Ω, 0.5-2Ω, 0.1-3Ω, 2-4Ω, or within another range having the same, higher, lower, and/or intermediate bounds.

Optionally, during assembly, the resistive heating element 2306 is attached to the housing 2301, in a position overlying pallet 2304 on one or more sides. For example, the resistive heating element 2306 extends from a dorsal surface 2309A to fold around housing end 2311, and extend back along ventral surface 2309B. Optionally, resistive heating element 2306 extends around chamber 2303 such that pallet 2304 contained within chamber 2303 is enclosed by the heating element 2306. In some embodiments, resistive heating element 2306 comprises a plurality of separate panels, for example, panels 2356 and 2356A in FIGS. 1C-D, one on each side of the dose unit 2350. Optionally, the panels are electrically connected, one to the other. Alternatively, each receives separate electrical connections. A potential advantage of having multiple and separate panels for the resistive heating element is to allow controllable vaporization to occur in pre-selected regions of the pallet. A potential advantage of two-sided enclosure of pallet 2304 (used in some embodiments) is increased speed and/or uniformity of vaporization upon application of a current to the heating element 2306. In some embodiments, only one panel 2356 of the enclosure is an electrically resistive element, and the other panel 2356A is optionally a mesh or other air-permeable structure (for example, a porous structure) which provides mechanical support.

In some embodiments, electrically resistive heating elements 2356, 2356A are operated simultaneously. In some embodiments, the resistive heating elements are operated separately. This is a potential advantage, for example, to allow separate control and/or release of two different agents, and/or of a one agent in two sequential deliveries. For example, a first heating element (panel, for example) is operated with sufficient energy to vaporize an agent directly underneath it, but for a sufficiently short time or in such heating pattern that the heat does not reach all the way through the pallet. At some offset in time (optionally overlapping or entirely separate from the first heating), a second heating element is operated. Potentially, this is an advantage when two substances having different volatilization properties as a function of time or temperature are to be released (for example, from two different pallet materials). Optionally, the two heating profiles are adjusted to result in simultaneous vaporization. Additionally or alternatively, vaporization of two agents is deliberately offset in time. For example, a pallet comprising a flavoring or masking agent is placed in the pallet near a heating element where it is vaporized first, and a second agent vaporized shortly thereafter (or the reverse). This is a potential advantage, for example, to mask potentially unpleasant tastes, to signal a user as to a status of vaporization in process, and/or to otherwise modify the sensory experience of inhalation. Optionally, each electrode heats across a whole side of the pallet. Alternatively, each heating element is formed so that vaporization heating occurs only across a portion of the pallet, optionally in a different portion for each electrode. In some embodiments, one heating element is used to "pre-warm" a pallet to a threshold below active agent release, and a second heating element is activated to achieve release itself. Potentially, pre-warming followed by release heating shortens a period of agent vaporization and/or increases a concentration upon release. Potentially, this helps to increase the amount of agent reaching the lungs, and/or to target release to a narrower selected respiratory depth.

In some embodiments, resistive mesh 2306 comprises a ratio of open (aperture) to closed (mesh material) surface area of between about 1:1 (50%) and 1:3 (33%). In some embodiments, the ratio is in the range of about 10-20%, about 20-40%, about 30-50%, about 40-70%, about 60-80%, about 70-90%, or another range of ratios having the same, larger, smaller, and/or intermediate bounds. In some embodiments, the apertures of the mesh are in the range of about 10 μm, about 25 μm, 32 μm, 50 μm, 75 μm, 100 μm, 200 μm, 300-750 μm, 700-1200 μm, or another larger, smaller, or intermediate range. Optionally, at least two apertures have different size and/or shape. In some embodiments, the mesh is a 400/0.03 316 stainless steel mesh, with 0.033 mm holes, 400 holes per square inch, wherein each hole is about 0.033 mm (33 μm), a 0.03 mm thick wire.

In some embodiments, at least one heating element 2306 is embedded wholly or partially within pallet 2304. Optionally, a heating element 2306 is embedded partially or wholly within the frame of a housing 2301. For example, the housing 2301 is originally molded with the heating element in place, and/or the heating element 2306 is pressed into place under high temperature at another stage of manufacturing. Optionally a plurality of heating elements 2306 are embedded wholly or partially within pallet 2304, such that they may be operated simultaneously or separately.

Figure 1H:
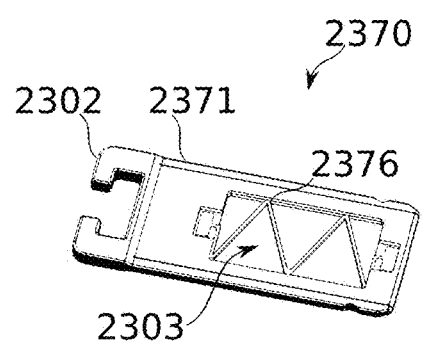
Figure 2A:
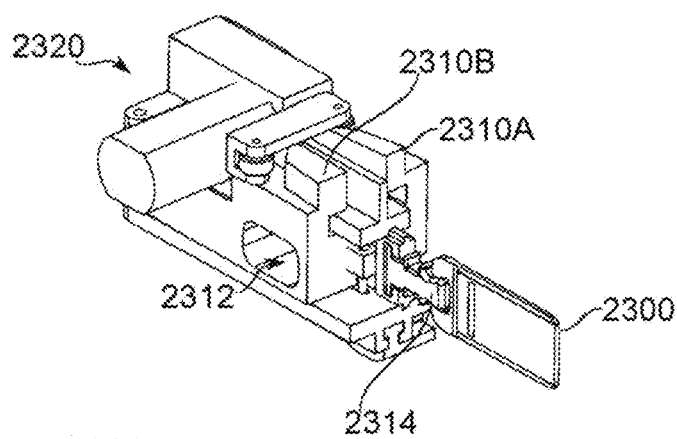
Figure 2B:
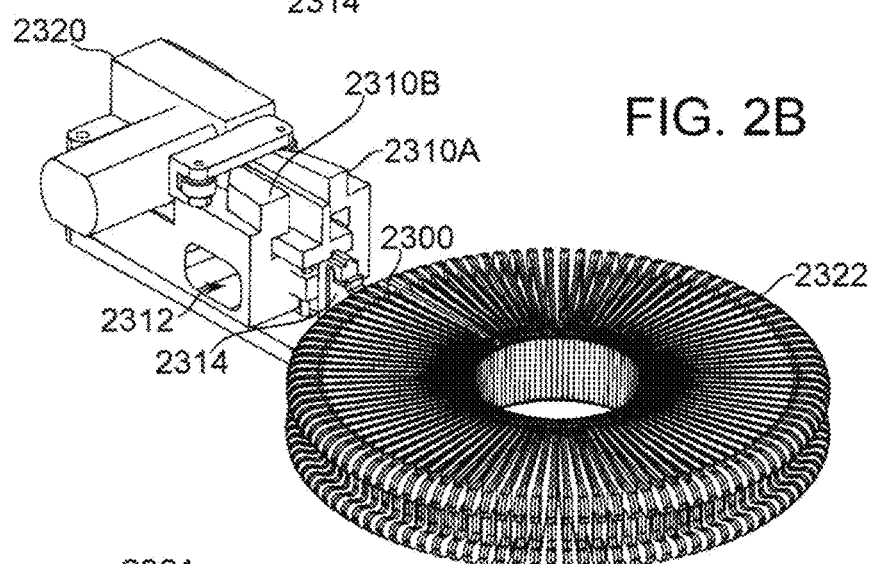
Figure 2C:
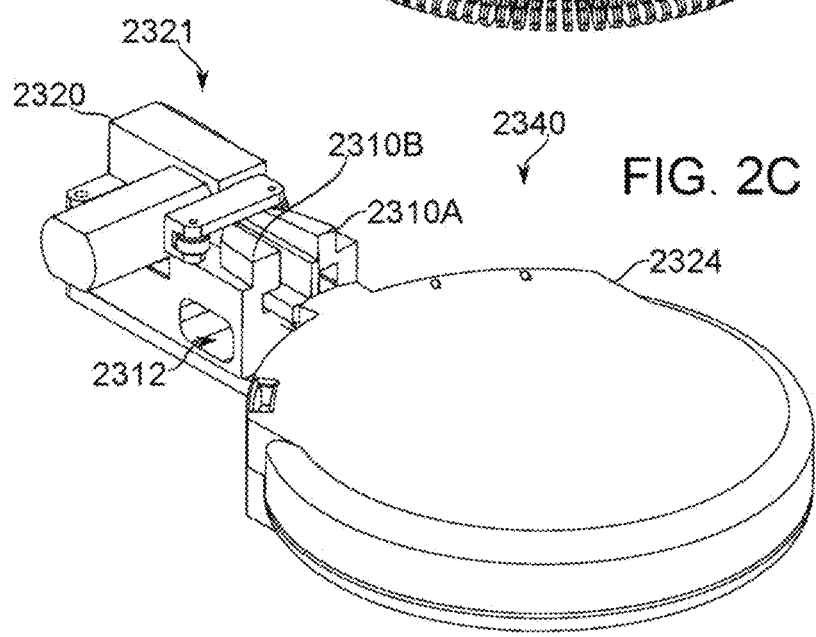
Figure 2D:
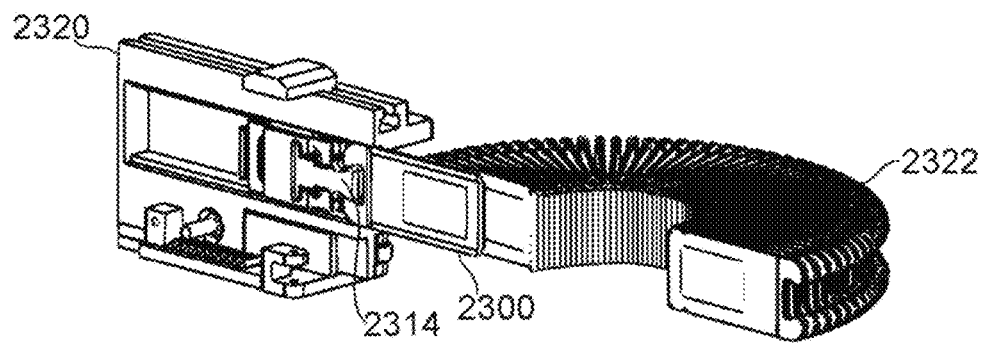
Figure 2E:
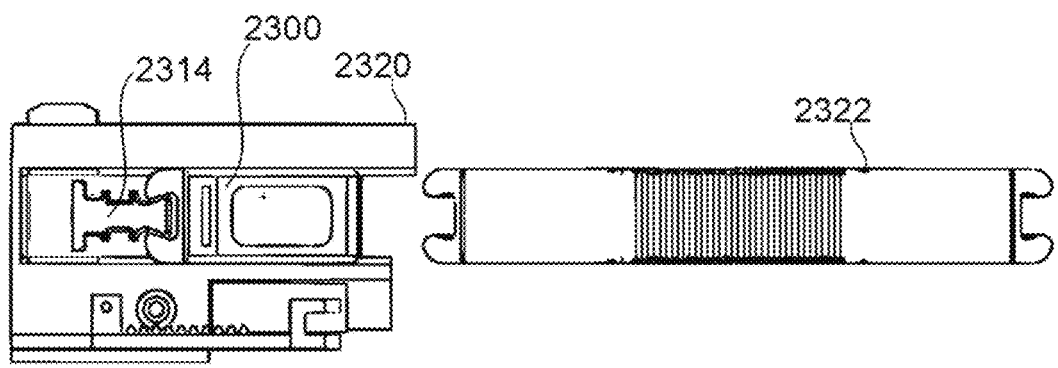

FIGS. 1G-H show another embodiment of a dose unit 2370 comprising an embedded heating element 2376 in a frame 2371. In some embodiments, heating element 2376 comprises a heating section 2378 arranged between a plurality of electrode pads 2377. In the assembled dose unit, heating section 2378 extends across or within chamber 2303 and across or through pallet 2304. For example, pallet 2304 is optionally formed by pressing loose material into place around the heating element 2376, embedding it. Optionally, frame 2371 comprises one or more recesses 2377A, which receive electrode pads 2377. In some embodiments, additional mechanical support for the pallet is provided by a permeable overlay 2375, extending over at least one side of the dose unit frame 2371. Overlay 2375 optionally comprises a polymer mesh or other structure allowing gas flow.

In some embodiments, the heating section 2378 of heating element 2376 is formed as a wire which crosses chamber 2303 one or more times in connecting to electrode pads 2377. In some embodiments, heating section 2378 comprises a mesh, ribbon, or other shape. In some embodiments, heating section 2378 is divided into a plurality of separate parts (branches, layers, or other divisions). In some embodiments, the heating section 2378 extends nearby (for example, within 1 mm, within 2 mm, or within another larger or smaller distance) substantially all parts of the pallet containing the drug substance to be released. This is a potential advantage for obtaining more rapid and/or uniform substance release upon heating.

It is to be understood that although electrode contacts 2377 are electrically separated from one another except as joined by the heating section 2378, they need not be placed physically distant from one another, depending, for example, on the course(s) run by the heating section 2378 itself. Optionally, the electrode contacts are placed on the same or on different sides of chamber 2303, for example.

In some embodiments, resistive heating element 2306 comprises an etched resistive foil (for example a foil etched into a continuous ribbon or other shape, and backed by a polymer such as polyimide and/or silicone rubber). Optionally a backed resistive foil is perforated through the backing to allow airflow during volatilization of the dosing substance. In some embodiments, a fuse is added to the resistive foil, for example as an added component, and/or as a region of ribbon manufactured deliberately thin, so as to provide a method of destroying the heating element after use (by sending an appropriately high current through the heating element for a sufficient period of time).

In some embodiments, resistive heating element 2306 is secured to cartridge housing 2301 by pressing the mesh onto the housing using a temperature high enough for the housing to melt and/or soften such that the mesh becomes embedded in the material of the housing. In some embodiments, the housing comprises an inert, thermally resistant, non-conducive material. In some embodiments, the housing material used comprises, for example, a liquid crystal polymer (LCP), polyether ether ketone (PEEK), Ultem, Teflon, Torlon, Amodel, Ryton, Forton, Xydear, Radel, Udel, Polypropylene, Propylux, Polysulfone, or another polymer material.

A potential advantage of LCP and/or PEEK is good resistance to temperature higher than a temperature needed to vaporize a substance held in the cartridge. In some embodiments, bonding of mesh and housing occurs at a temperature of about 280° C. (or another temperature high enough to melt and/or soften LCP or PEEK). LCP and PEEK provide the potential advantage of good thermal stability at lower temperatures, for example, at a vaporization temperature of about 230° C.

A potential advantage of providing a heating element, such as resistive heating element 2306, for each individual dose unit is to provide uniformity of performance between uses. Potentially, a portion of the bioactive agent with which a heating element comes into contact remains stuck to the heating element after cool down. This buildup has the potential to affect vaporization performance. Remote heating (by radiation and/or indirect conductance, for example) potentially produces a system having relatively high thermal inertia (needing greater heating power) compared to direct conductive heating by a contact electrode; the problem of contact electrode contamination is removed by designing it for single use. A lowered requirement for heating potentially increases safety and/or device longevity. Potentially, a lowered requirement for heating also lowers demands on power delivery, allowing embodiments with increased portability, greater charge life, and/or lowered expense (for example, for systems having battery-powered heating elements).

In some embodiments, dose unit 2300 comprises a locking member for use in dose unit transport. The locking member comprises, for example, a latch mandible 2302. The locking allows engagement by one or more matching members of a dose magazine transport mechanism, for securing and/or movement of the dose unit. Dose unit movement and/or securing against unwanted movement may occur during the dose unit life cycle, for example, when the dose unit is placed into a queue of dose units comprising a plurality of dose units arranged for use, when the dose unit is advanced in the queue, when a dose unit is selected for use, when a dose unit is moved into position for use, when a dose unit is actually used, and/or when a dose unit is discarded, or, alternatively, moved to a "used" position in the dose unit queue.

Carousel and Vaporizing Device:

Reference is now made to FIGS. 2A-E, which schematically illustrate a carousel-type dose delivery system 2340 for use as a part of an inhaler device or even an MDI device, according to some embodiments.

In some embodiments, dose delivery system 2340 comprises carousel 2322 holding a plurality of dose units 2300 encased by enclosure 2324, and vaporizing apparatus 2321 comprising dose puller 2314 and clamping chamber apparatus 2320. Carousel enclosure 2324 and vaporizing apparatus 2321 are attached to one another; carousel 2322 revolves to present dose units to vaporizing apparatus 2321 in the order of their loading, or in another order, as selected by operation of carousel 2322.

Optionally, carousel enclosure 2324 (and its contents) is exchangeable for a new enclosure assembly, for example when some or all dose units are spent, expired or need to be replaced to change the dose unit composition. The number of dose units carried by an enclosure is, for example, about 100. Optionally, the number of dose units is another number within the range of 10-200 (for example, 10, 40, 80, 120, 180, or 200), or another larger or smaller number. In some embodiments, carousel diameter is, for example, within the range of about 7-10 cm, or another larger or smaller diameter, according, for example, to the number and size of dose units to be accommodated. Optionally, carousel 2322 comprises identical dose units or a plurality of different dose units (for example, containing different amounts, concentrations, and/or isolated bioactive agent compositions). It is to be understood that a carousel is not the only form of cartridge storage device which is usable with dose units. For example, the dose units can be stored within a spring-loaded magazine-type storage system. A potential advantage of a carousel is free (rather than strictly serial) access during loading and/or unloading to dose unit positions; for example, to adjust a dosing regimen. Other potential advantages of using a carousel relate to secured storage, abuse control, safety and other regulatory compliance and requisites.

In an example of an operation cycle, dose puller 2314 is actuated to extend from the vaporizing apparatus into carousel enclosure 2324, where it attaches to a dose unit 2300, for example, by means of latch mandibles 2302. In some embodiments, the dose puller 2314 "snaps" into place within the latch mandibles 2302. In some embodiments, the dose puller 2314 comprises two parts which move laterally past opposite sides of, and then close together within the space defined by the mandibles 2302 (potentially applying a lower force to the mandibles 2302 and/or dose unit 2300 than a snap-inserting method). A further action draws the actuator back into the vaporizing apparatus, and the attached dose unit 2300 along with it. The dosing substance load 2304 of dose unit 2300 is drawn thereby into communication with an air intake 2312. It is to be understood that a dose puller potentially operates in a mode other than transport by an actuated arm: for example as a dose "pusher" (comprising, for example a spring loaded member in the carousel volume itself), and/or a magnet (in a pulling mode) or magnets (in a pushing or pulling mode).

In some embodiments, clamping members 2310A and 2310B close on the cartridge, bringing electrodes into place for heating the dosing substance for vaporization of the volatile substances within it.

Reference is now made to FIGS. 3A-B, which schematically illustrate clamping chamber apparatus 2320 for vaporizing and delivery of an isolated bioactive agent from dose unit 2300, according to some embodiments.

Dose unit 2300 is transported into the clamping chamber apparatus 2320, for example by movement of dose puller 2314 while engaged with latch mandible 2302.

In some embodiments, clamping chamber apparatus 2320 (also referred to as vaporizing apparatus) comprises two clamping members 2310A, 2310B, which engage dose unit 2300 during vaporization. In some embodiments, each clamp 2310A, 2310B carries a corresponding electrode 2330A, 2330B, which is positioned to come into pressing contact with resistive heating element 2306 or other heating element which form a part of dose unit 2300. Electrodes 2330A, 2330B are in turn in electrical contact with a power supply. Heating is effected, in some embodiments, by switching current through the electrodes 2330A, 2330B, via resistive heating element 2306. The electrodes 2330A, 2330B are positioned such that current follows pathways extending over substantially all of at least one side (two sides, in the illustrated example) of the dosing substance load, such that heat may be evenly distributed over and conducted to the surface of load 2304.

In some embodiments, air flow passes through intake 2312, through heated pallet 2304, and out of the output aperture 2312B. Optionally, the output aperture 2312B is in fluid communication with a tube which is routed for delivery of the vaporized substances to a user. Optionally, the clamping members 2310A, 2310B comprise portions of the intake 2312 and output 2312B. Potentially, this allows the clamp members 2310A, 2310B to alternately open to receive dose unit 2300, and close to seal an airway passage around dose unit 2300, so that vaporized isolated bioactive agent(s) are kept confined to a defined passageway.

After dose delivery, ejection of the dose unit comprises disengagement of dose puller 2314 from latch mandible 2302; for example, by displacing one of the two parts while restraining the other from following, and/or by deforming one of the two parts. For example, puller 2314 is further retracted, while dose unit 2300 is prevented from following by a restriction in the size of the slot through which it moves. In some embodiments, disengagement is followed by ejection: for example, the dose unit falls out of its slot, is pushed by a returning action of the dose puller 2314, and/or is otherwise transported out of the device altogether. In some embodiments, the dose unit is returned to carousel 2322 as a used dose (into the same, or another available slot different from the one it was retrieved from). Optionally, this is performed shortly or immediately at the end of use. Alternatively, the dose unit is ejected in the framework of a next use of the device, in which case the carousel also advances to present the next dose unit to be used.

In some embodiments, access to doses loaded in the carousel is sequentially in the order of their loading. In some embodiments, dosage order is pre-determined but variable; for example, dosages of different amounts for administration throughout a period of time are arranged in that order when the carousel is loaded. In some embodiments, carousel movement (advancing) is substantially according to a sequence of actions which are mechanically coupled to the dose pulling and/or dose returning actions. In some embodiments, carousel movement is under the control of a controller, for example, a microprocessor-controlled stepper motor or other advancing mechanism. Optionally, the controller tracks which dosage is in which cartridge slot, and/or its status. Optionally, the controller automatically and/or upon command selects an appropriate dose unit, and advances it into position by as many steps as needed to make it available for pulling. Optionally, this selection allows out-of-order access to dose units in the carousel. Optionally the carousel is advances as a result of a user actuating the device.

Detachable Vaporizing and Delivery Device:

Reference is now made to FIGS. 4A-B, which schematically illustrate an inhaler device for loading from a carousel and separable from the carousel for vaporizing and delivery of an isolate bioactive agent from a dose unit, according to some embodiments.

In some embodiments, functions performed by clamping chamber apparatus 2320 are performed by separable parts, such that a clamping/heating/administration subassembly is separable from portions of a dose storage pulling and transport subassembly, at least for dose administration to a user. In some embodiments, the clamping/heating/administration assembly 2400 comprises a substantially cylindrical body (for example, cigarette, cigarillo, cigar, and/or pen shaped), which inserts into a receptacle of the dose pulling and transport assembly. The assembly 2400 comprises a slider mechanism 2410 or other structure which is engaged by the transport assembly, and/or is activated by manual or other external operation.

Optionally, slider mechanism 2410 slides out of the intake end 2440 of the assembly 2400 to engage dose unit 2300 with engaging part 2415, as described, for example, in relation to dose puller 2314. Optionally, dose unit 2300 (formed, for example, with a long and narrow pallet 2404) is pulled into the clamping/heating assembly. The clamping/heating assembly optionally comprises electrodes 2430 which are loaded with spring members 2407, or another means, for pressing against resistive heating element 2306 to provide electrical contact thereto. Optionally, power for heating is supplied by a battery 2413 connected to electrodes 2430 via wires 2414.

Optionally, the battery 2413 is rechargeable, for example, the battery 2413 recharges from a supply provided by the main body assembled together with the carousel. Optionally, heating begins upon operation of a control (such as a button), and/or is subject to one or more automatic activation, modulation, and/or interlock controls, such as heating upon sensing of a change in pressure, and/or air shunt opening to control speed and/or amount of dose delivery. During delivery, air is drawn through the body 2420 (for example, orally by inhalation), by applying suction to end 2450. Air drawn into intake end 2440 is forced by baffles/conduits 2401, 2408 to pass through the heated pallet 2404, carrying vaporized bioactive gent to end 2450.

A potential advantage of the separable design is to reduce the effort required by a user to manage the dosing device at the time of dose administration. Another potential advantage is to separate the functions of dosage selection, management, and control from the dosing itself. There is a potential positive psychological effect due the separation of the dosing act, which approximates that of a normal e-cigarette, from the more clinical aspects of dosage control.

In some embodiments, a removable dose unit comprises a plurality of separately heatable regions; for example, material is loaded into different apertures, and/or an aperture which is crossed by a plurality of separately addressable heating elements. Optionally, the different loads comprise different isolated bioactive agents. For example, a cannabis load is optionally followed by one or more isolated cannabinoid loads such as isolate THC, and/or by loads of a different cannabinoid, such as isolated CBD.

In some embodiments, analog and/or digital circuit logic is used to control which heating element region receives current. For example, each heating element is optionally deliberately "burned" (by fuse breaking, for example) after use. A suitably arranged sensing circuit detects a first unused dosing region, and selects it for the next activation. A potential advantage of this is to allow a dosage to be spread over multiple inhalations. Another potential advantage is to allow a dosage for one purpose (for example, a medicinal purpose) to be combined with dosages for another purpose (for example, an alternative medicinal purpose, or to allow additional inhalations for recreational purposes). Another potential advantage is to allow the use of multiple dose types (for example, different isolated bioactive agents' compositions) for the sake of giving variety to the user's experience.

Reference is now made to FIG. 5, which schematically illustrates an interlock-protected dose dispensing apparatus 2500, together with a removable dose administration assembly 2400, according to some embodiments.

In some embodiments, dispensing apparatus 2500 comprises a plurality of receiving apertures 2501, 2502 for the administration assembly 2400. In some embodiments, aperture 2501 is an aperture from which an unused dose unit 2300C, 2300A is retrieved into administration assembly 2400. In some embodiments, after a dose unit 2300A is extracted from the dispensing apparatus 2500, the next dose unit 2300C does not advance into position until the conditions enforced by an interlock device are met. In some embodiments, operation of the interlock device comprises inserting administration assembly 2500 into aperture 2502. Optionally, insertion triggers (for example, by mechanical and/or controller-actuated operation) the movement of the carousel such that a dose unit 2300C is moved into position. In some embodiments, insertion (optionally insertion and removal) of the administration assembly 2400 extracts dose unit 2300A, which now occupies the former position of used dose unit 2400B. Potentially, this interlock mechanism helps to ensure that only one dose unit at a time is removed from the dispensing apparatus 2500. In some embodiment, advancing of the carousel does not occur unless dose unit 2300A is sensed within the administration assembly 2400 upon insertion into aperture 2502. In some embodiments, dose unit 2300A is inserted into administration assembly 2400 such that it cannot be removed without destruction of dose unit 2300A and/or the administration assembly 2400.

Inhaler Device:

The dose unit comprising a pallet of one or more isolated bioactive agents disposed over a carrier material and configured to effect vaporization thereof by a heating element according to some embodiments, can be used in an inhaler device configured to actuate electric current through the heating element and allow passage of air to pass through the heated pallet to carry the vaporized agent to a pulmonary organ of a patient or user. An inhaler device using the dose unit presented herein may be a metered dose inhaler (MDI) device.

In some embodiments, the device is configured for precise dosage suitable for medical purposes. Precise dosage may be effected by using a pre-measured amount of the bioactive agent(s) and/or controlling the heat profile (e.g. temperature and/or heating rate and/or duration) applied for vaporization and/or the flow profile (e.g. flow rate and or variation of flow rate and/or duration). In some embodiments, the device is configured for general vaporization of bioactive agent(s) while precision requirements be lax.

According to some embodiments, the inhaler device comprises at least one dose unit as described herein, and further comprises an activating unit configured to move the dose unit from a storage position into a use position and actuate passage of current through the heating element, as described hereinabove.

According to some embodiments, the inhaler device further comprises a dose unit dispensing apparatus that holds a plurality of dose units.

According to some embodiments, the inhaler device further comprises a clamping chamber apparatus (also referred to as vaporizing apparatus), as described hereinabove.

According to some embodiments, the inhaler device is an MDI device essentially as described in International Patent Application No. WO 2012/085919 and/or in any one of U.S. Provisional Patent Application Nos. 62/035,588, 62/085,772 and 62/086,208, including any one of the embodiments described therein, and any combination thereof.

According to one aspect of some embodiments, there is provided an MDI device configured for pulmonary delivery of a pre-determined vaporized amount of at least one bioactive agent (a pharmacologically active agent) to a patient, wherein the agent is an isolated bioactive agent, and:

the device is configured to deliver said pre-determined vaporized amount of the agent upon controllably heating a pallet comprising the agent;

the pre-determined vaporized amount is selected such that it affords a pre-selected pharmacokinetic profile and/or a pre-selected pharmacodynamic profile of the agent in the patient; and the pre-determined vaporized amount is derived by measuring at least one pharmacokinetic (PK) parameter and/or at least one pharmacodynamic (PD) parameter induced by the pulmonary delivering of the agent in the patient from the MDI device (PK/PD studies). Such PK/PD parameters are generally known in the art and discussed hereinbelow, and may be measured or estimated according to well established methodologies, referred to herein as PK/PD studies.

According to some embodiments, the MDI device is configured for communication with a patient interface circuitry and be integrated in a system designed to allow PK and/or PD (PK/PD) data acquisition and input, patient records' storage, automatic or manual calibration, adjustment, resetting and re-determination of the initial presetting of the device by the patient and/or by a practitioner, as will be described in details hereinbelow.

Inter-variability of PK/PD among the cohort of patients is notably low for some isolated bioactive agents, and may be afforded by use of an accurate and consistent MDI device, according to some embodiments of the present disclosure.

According to some embodiments, the methods and device presented herein are also characterized by a high accuracy, consistency, precision and reproducibility, which are expressed by a minimal deviation between the actual vaporized amount of the agent being inhaled by the patient, and the pre-determined vaporized amount of the agent.

According to some embodiments, the inhaler device for controlled vaporization of at least one active pharmaceutically active agent from at least one type of substance by application of heat comprises:

at least one dose unit (cartridge) containing a pallet that comprises at least one isolated bioactive (pharmaceutically active) agent;

a heating element adapted to apply heat to the pallet to vaporize the pharmaceutically active agent; and a mechanism adapted for moving the cartridge relative to a controller for powering the heating element.

According to some embodiments the inhaler device is configured for controlled vaporization of at least one active pharmaceutically active agent from at least one type of substance by application of heat and air flow and accordingly also comprises a mechanism adapted to control air flow through the pallet.

In some embodiments, the device further comprises a plurality of dose units arranged in a tape, a daisy (carousel) or a magazine. Optionally or additionally, the pallet is organized with a pre-determined amount of the pharmaceutically active agent per unit area of the pallet in each dose unit in the tape, the daisy or the magazine.

Optionally or additionally, a thickness of the dose unit ranges from about 0.1 mm to about 2.0 mm. Optionally or additionally, the tape, the daisy or the magazine comprises a total of about 5 grams to about 100 grams of loaded pallets. Optionally or additionally, the tape, the daisy or the magazine comprises a sufficient amount of the active pharmaceutically active agent for at least two treatments. Optionally or additionally, the cartridge comprises a first material layer coupled to the pallet, the first layer comprising apertures large enough to let gas escape but small enough to contain the heated pallet material. Optionally or additionally, a diameter of the apertures ranges from 25 μm-500 μm. Optionally or additionally, the cartridge comprises a second material layer coupled to the pallet, the second layer adapted to transmit heat to the pallet without substantially distributing the heat across the second layer. Optionally or additionally, the heating element and the pallet are held between the first and the second layers.

In some embodiments, the device further comprises an inhaler unit, the inhaler unit comprising a mouthpiece for inhalation of the pharmaceutically active agent, the mouthpiece forming fluid communication with a vapor chamber of the device, the vapor chamber comprising the vaporized active pharmaceutically active agent.

Optionally, the mouthpiece comprises a one way valve to control fluid flow away from the vapor chamber. Optionally or additionally, the device further comprising a sensor in fluid communication with the mouthpiece, the sensor adapted to estimate an air flow rate and send a signal to a controller, the controller adapted for vaporizing the pharmaceutically active agent according to the airflow rate.

In some embodiments, the device further comprises a controller configured to synchronize the application of heat with the movement of a cartridge and/or with airflow rate effected by inhalation.

In some embodiments, the device further comprises circuitry for controlling (controller) activation of the heating element.

In some embodiments, the device further comprises a communication interface for communicating to one or more external computers and/or systems and/or patient/physician interfaces.

In some embodiments, the device further comprises or is associated with a dose display meter for providing visual output of the vaporization of the pharmaceutically active agent.

In some embodiments, the device is portable and weighs less than about 300 grams.

In some embodiments, the device further comprises or is associated with a memory adapted to hold at least one of prescription data and usage data, the memory coupled to the controller, the controller adapted to control at least one of the heating element, air flow and the transport mechanism according to the dose and/or regimen data.

In some embodiments, the device further comprises a unique ID adapted for tracking the device use by an associated patient.

In some embodiments, the device further comprises a sensor adapted to detect a physical breach of the device.

There is provided in accordance with some embodiments, a method for controlled vaporization of an active pharmaceutically active agent from a pallet, the pallet is organized as a cartridge (dose unit), the method comprising:

applying heat to an area of the cartridge to vaporize a predetermined amount of the active pharmaceutically active agent and;

moving the cartridge relative to a heat source.

Alternatively, the heating element is comprised within the cartridge, and the cartridge is moved relative to electrical contacts for powering the heating element.

In some embodiments, the method further comprises adjusting at least one of timing and speed of the moving to vaporize the active pharmaceutically active agent according to a delivery profile.

In some embodiments, the vaporizing comprises vaporizing during pulmonary delivery.

In some embodiments, the applying heat comprises applying heat to reach a target temperature in less than 500 milliseconds after a start signal.

According to some embodiments, there is provided a method for controlled vaporization of at least one isolated active pharmaceutically active agent from at least one type of pallet by application of heat, the method comprising:

heating one or more areas of one or more pallets organized in one or more cartridges with one user trigger, to release the at least one active pharmaceutically active agent. Optionally, the areas comprise different isolated active pharmaceutically active agents.

According to some embodiments, there is provided a method of manufacturing a cartridge having pallet comprising an isolated active pharmaceutically active agent, the cartridge adapted for use with a device for automatically applying localized heat to vaporize the pharmaceutically active agent, the method comprising:

applying at least one, optionally premeasured, amount of an isolated pharmaceutically active agent in and/or on a pallet material;

optionally measuring the amount of pharmaceutically active agents present in and/or on a unit mass of loaded pallet material; and pressing the pallet into the cartridge.

Optionally, measuring the amount of a pharmaceutically active agent includes one or more of directly measuring the pharmaceutically active agent and weighing an amount of material comprising the pharmaceutically active agent.

In some embodiments, pressing particulate loaded pallet material is performed in a cartridge having apertures with a size smaller than the size of the particles.

In some embodiments, the method further comprises marking the cartridge with pre-determined amount of the active pharmaceutically active agent.

According to some embodiments, there is provided a cartridge for therapeutic drug delivery comprising a pallet loaded with an isolated active pharmaceutically active agent, said pallet is loaded with a predetermined amount of the pharmaceutically active agent per unit area of the cartridge, and a heating element comprised therein.

In some embodiments, a plurality of cartridges is organized as a roll of tape, a carousel (daisy) or a magazine.

Controllable Release and Delivery:

According to an aspect of some embodiments, there is provided a method for controllably releasing at least one isolated bioactive agent using an inhaler device as described herein.

According to some embodiments, the method is carried out using an MDI which is capable of delivering reproducibly and accurately, by pulmonary inhalation, an amount of at least one vaporizable agent by heating a pallet comprising the vaporizable agent according to some embodiments, vaporizing the agent effectively and efficiently, and having said vaporized agent inhaled by the user. Such requirements of an MDI are met by, for a non-limiting example, an MDI as disclosed in International Patent Application No. WO 2012/085919 and in any one of U.S. Provisional Patent Application Nos. 62/035,588, 62/085,772 and/or 62/086,208 which are incorporated herein by reference in their entirety as if fully set forth herein.

The controllability is afforded by one or more of controlling the amount of the isolated bioactive agent(s) in the dose unit, controlling the heating level applied to the dose unit by controlling the current passed through the heating element, and/or the duration thereof, and controlling the configuration and/.or air flow via air passages in the device which may at times ensure a complete inhalation of the entire volume which includes the vaporized amount of the bioactive agent.

Controllability of the vaporized amount of the bioactive agent in its isolated form provides for example means to use the bioactive agent as a pharmaceutical agent (a drug; a medicament) having known and substantially predictable and reproducible pharmacological parameters such as a pharmacokinetic (PK), a pharmacodynamic (PD) profile which allow the attainment of a desired regimen to fit a known and substantially predictable and reproducible therapeutic window. Thus, according to some embodiments, the method of controllably releasing by vaporization and pulmonary delivery by inhaling a pre-determined vaporized amount of at least one isolated bioactive agent as presented herein, is effected such that the pre-determined vaporized amount is selected so as to exhibit a pre-selected pharmacokinetic profile and/or a pre-selected pharmacodynamic profile of the agent in the patient.

As used herein, the terms "therapeutic window" and "pharmaceutical window" are interchangeable and refer to the range of pharmacodynamic effects induced by a range of doses of one or more pharmaceutically active agents, providing a balance between one or more desired (positive) effect(s) and one or more adverse (negative) effect(s). According to some embodiments, the pharmaceutical/therapeutic window is referred to as a pharmacodynamic profile. The window may relate to a given point in time or may span a period of time of any length, including for example minutes, hours, days or longer, shorter or to any intermediate period of time. The desirability and undesirability of an effect can be defined based on a variety of criteria, and include without limitation, medical practices, rules and regulations, cultural and demographic norms, genetic factors and personal preferences and tolerances. For example, the desirability and undesirability of an effect can be defined based on the purpose of treatment and based on generally acceptable values and optionally may take into account other parameters such as patient preference, capacity and activity. It is noted that a given effect may be regarded as desired in some cases, but be regarded as undesired in other cases, and vice versa.

It is noted herein that according to some embodiments, by exhibiting a pre-selected pharmacokinetic and/or pharmacodynamic profile, it is meant that the vaporized amount of the isolated bioactive agent has been pre-determined based on pharmacokinetic/pharmacodynamic (PK/PD) studies conducted according to well established practices and acceptable standards in at least one subject, by pulmonary delivering to the subject the agent using an MDI device which is configured to release a consistent and accurate vaporized amount of the agent upon heating a pallet comprising the same, as described herein. It is also noted herein that according to some embodiments, by exhibiting a pre-selected pharmacokinetic profile, it is meant that at least one desired pharmacokinetic profile has been identified and that at least one pre-determined vaporized amount of the isolated bioactive agent has been shown to effect that desired pharmacokinetic profile in a subject. It is also noted herein that according to some embodiments, by exhibiting a pre-selected pharmacodynamic profile, it is meant that at least one desired pharmacodynamic profile has been identified and that at least one pre-determined vaporized amount of the agent has been shown to effect that desired pharmacodynamic profile in a subject in a reproducible manner. It is also noted that for some isolated bioactive agents, ingestion and/or injection thereof by a random subject leads to unpredictable and/or inconsistent and/or inoperable pharmacokinetic parameters' values, for which the method presented herein may provide a highly advantageous solution.

In some embodiments, both the terms "pre-selected" and "pre-determined" refer to, or used interchangeably with the terms "intended", "target", "desired" or "desirable", or with the terms "effective", "needed" and "therapeutic".

It is also noted herein that the identification of a desired pharmacokinetic profile and/or a desired pharmacodynamic profile, is typically afforded by conducting PK/PD studies for a particular pharmaceutically active agent in a particular subject or a group thereof. It is also noted herein that the ability to conduct standard and widely accepted PK/PD studies in a particular subject or a group thereof for a pharmaceutically active agent, which is delivered by inhalation (pulmonary delivery) upon controllably and reproducibly releasing a vaporized amount of an isolated bioactive agent by heating a pallet comprising the same, is made possible (enabled) by, for example, an MDI device such as disclosed herein and/or in International Patent Application No. WO 2012/085919 and in any one of U.S. Provisional Patent Application Nos. 62/035,588, 62/085,772 and/or 62/086,208, all of which are incorporated herein by reference in their entirety.

In some embodiments, the term "pre-determined vaporized amount" is also used herein to describe the amount of the agent that is determined based on data indicative of a pharmacokinetic parameter and/or a pharmacodynamic parameter, namely a vaporized amount that has been determined by monitoring and/or recording and/or receiving and/or analyzing and/or determining at least one PK parameter and/or PD parameter that is/are induced by a given agent in one or more subjects/patients.

In some embodiments, configuring the MDI device to release a pre-determined amount means calibrating the device to elicit a pre-selected PK and/or a pre-selected PD profile. The controllable, accurate and reproducible release of an isolated bioactive agent from the dose unit presented herein may allow calibrating an MDI device as provided herein.

According to some embodiments, the method is carried out by determining at least one pharmacokinetic parameter (also referred to herein interchangeably as pharmacokinetic effect) and/or at least one pharmacokinetic variable and/or at least one pharmacodynamic parameter (also referred to herein interchangeably as pharmacodynamic effect), as these terms are known in the art, which are induced by pulmonary delivering a vaporized amount of the bioactive agent to a patient using the MDI device:

based on the pharmacokinetic parameter and/or the pharmacokinetic variable and/or the pharmacodynamic parameter, determining the pre-determined vaporized amount which exhibits the pre-selected pharmacokinetic profile and/or the pre-selected pharmacodynamic profile of the agent in the patient; and adjusting/readjusting/configuring the MDI device to deliver the pre-determined vaporized amount of the agent.

As used herein, the phrase "pharmacokinetic profile" refers to a bodily concentration of a pharmaceutically active agent, or a metabolite thereof (e.g., an active metabolite), namely, a concentration of the agent or a metabolite thereof in a physiological system of an organism (whole body, blood, plasma, lymph, tissue, organ and the likes) to which the compound has been administered, as a function of time. Typically, a pharmacokinetic (PK) profile is considered from a time point of administration of the compound to a time point at which the compound is no longer detectable in the organism or a portion of this period of time; hence, a PK profile may describe the bodily concentration in a specific physiological system of a specific compound between administration and dissipation, as affected by the mechanisms of liberation, absorption, distribution, metabolism and excretion/secretion of the compound. Since each organism, and each individual organism within a genus of an organism, reacts differently to the administration of the agent, a PK profile may be different, and in some cases highly variable from subject to subject, and may be different within an individual subject based on a current physiological state, medical condition, environmental conditions and even the time of day.

According to some embodiments, a pharmacokinetic profile is achieved by providing a subject with one or more of:

A dose—a single amount of a compound or an agent that is being administered thereto;

Dosing—a plurality of pre-determined doses which can be different in amounts or similar; and/or A regimen—a dosing given at various time intervals, which can be different or similar in terms of duration. In some embodiments, a regimen also encompasses a time of a delivery period (e.g., agent administration period, or treatment period).

Alternatively, a regimen is a plurality of predetermined plurality pre-determined vaporized amounts given at pre-determined time intervals.

It is noted that the PK profile can be determined according to a change of a PK parameter as a function of time, or of a combination of PK parameters a function of time. A PK profile is typically assessed on a concentration on a time scale, using directly and/or indirectly measured PK parameters. For example, a PK profile may be a plasma concentration of a given pharmaceutically active agent in a subject as a function of time.

The term "pre-selected pharmacokinetic profile", as used herein, refers to a PK profile which has been selected as desirable. A pre-selected PK profile may be selected since it has been found effective in accomplishing a desired pharmacodynamic effect in a subject, as described in any one of the respective embodiments (e.g., to maintain a subject within a therapeutic window, as described herein).

PK parameters typically include, without limitation:

$C_t$, which is the concentration of an agent, as determined, measured or assessed in a specific physiologic system (e.g., in the plasma), after its administration (delivery, e.g., pulmonary delivery) of a dose or a regimen to a subject;

$C_{max}$, which is the peak concentration of an agent, as determined, measured or assessed in a specific physiologic system (typically in the plasma), after its administration to the subject;

$T_{max}$, which is the time passed between administration and arriving at $C_{max}$;

Area under the curve ($AUC_{0\to\infty}$; zero to infinity), which is the integral of the concentration curve as a function of time, typically after a single dose or in steady state;

$C_{min}$, which is the lowest concentration of the agent in the organism before the next dose is administered;

$T_{min}$, which is the time passed until $C_{min}$ is detected, or until the next dose is administered;

$C_{last}$, which is the last observed quantifiable concentration;

$\lambda_z$, which is the terminal phase rate constant; Elimination half-life ($t_{1/2}$), which is the time required for the concentration of the agent to reach half of its original value; Elimination rate constant ($k_E$), which is the rate at which an agent is removed from the organism;

Administration rate ($k_{in}$), which is the rate of administration required to balance elimination;

Clearance, which is the volume of plasma cleared of the agent per unit time;

Bioavailability, which is the systemically available fraction of a agent; and

Fluctuation, which is the peak trough fluctuation within one dosing interval at steady state.

As a tool for assessing the PK profile in a member of a population of similar individual subjects (similar in the biological sense, as in a group of humans), PK variables, which have been found to be correlated to a PK profile in a sub-set of the population, may be used to generalize (extrapolate) the PK profile for each of the individuals comprising the entire population. Pharmacokinetic variables typically include, without limitation, body weight, body height, body mass index (BMI), waist-to-hip ratio, lean body mass (LBM), age, race, background illnesses, patient history, concurrent medication and gender. It is to be understood that PK variables depend on genetic and epigenetic composition of each individual subject, and therefore can be used to predict PK/PD profiles in an individual subject to a certain degree of accuracy; however, personalization/individualization of a treatment based on administration of a pharmaceutically active agent is typically based on personal PK/PD parameters (data) determined for an individual subject. In general, deviation of individual parameters from average parameters set for a wide population are notably small.

In the context of some embodiments, the term "treatment" refers to a single pulmonary administration of an isolated bioactive agent at a given dose, a fixed and limited series of pulmonary administrations of the agent (dosing) given at the same or different doses at the same or different dosing intervals (regimen), or a chronic treatment which is administered as the limited series, but without a pre-determined end (continuous treatment). Typically, a series of pre-determined doses given at pre-determined dosing intervals, is referred to herein as a treatment regimen, or a regimen.

According to some embodiments, the dose unit provided herein is a physical embodiment of a single dose that is used in a single inhalation session.

According to some embodiments of the method presented herein, pulmonary delivering the isolated bioactive agent comprises a single dose delivered as one pre-determined vaporized amount released by the MDI device in a single inhalation session, or the dose can be administered to a patient as several concomitant inhalations. Alternatively, a series of doses, each administered in one or more pre-determined vaporized amount, which is referred to herein as a dosing, and given at a pre-determined dosing intervals, is referred to herein as a regimen. A regimen is therefore defined by one or more doses, administered in one or more pre-determined vaporized amounts (dosing), at pre-determined dosing intervals, wherein each of the pre-determined vaporized amounts, the doses and the dosing intervals can be the same or different.

In the context of some embodiments, a PK profile of a given pharmaceutically active agent is a result of the dose, dosing and/or regimen by which an agent is administered to a patient, or, alternatively, according to some embodiments, the PK profile is a mean to afford a particular, a pre-selected or otherwise desired pharmacodynamic profile of the agent in the patient.

As used herein, the term "pharmacodynamic profile" refers to the effect of a pharmaceutically active agent in a subject as a function of time. Accordingly, the term "pharmacodynamic profile" refers to a sum of all biological expressions and responses of an organism as a function of time, upon administration of a pharmaceutically active agent. A pharmacodynamic profile is typically a direct or indirect result of pharmacokinetic effect(s) at any given time point, or a pharmacokinetic profile of the agent in the patient, over any given time period.

A pharmacodynamic profile represents a change/variation of directly and/or indirectly determined pharmacodynamic effects as a function of time.

Pharmacodynamic effects can typically be determined by, without limitation, a desired (therapeutic) effect (e.g., personally perceived therapeutic effect), an undesired (adverse) effect (e.g., a personally perceived adverse effect), and by means of determining a level of a biomarker (which is indicative of a desired and/or an undesired effect), as these terms are described hereinbelow. A pharmacodynamic profile which can be a pre-selected (desired) pharmacodynamic profile, according to some embodiments, is defined by the therapeutic window of a given agent in a given subject, as this term is defined herein.

A pharmacodynamic (PD) profile is typically a time-dependent assessment and/or measurement on a scale going from no response, through the onset of a desired therapeutic effect (below a therapeutic effect threshold), via the therapeutic window, through the onset of an adverse effect (above an adverse effect threshold), and up to a toxic effect. A potential advantage of the dose unit, device and methods presented herein is the enablement to practice administration by inhalation of particular isolated bioactive agents, which is conducive to a more accurate and reproducible assessment of PD parameters in any given subject, compared to the assessment of PD parameters when administering the same agent by ingestion and/or injection, due to low bioavailability associated with hydrophobicity, viscosity and other agent-specific properties as discussed hereinabove.

The results of such a PK/PD study, conducted using the dose unit, devices and methods provided herein in one or more subjects, can therefore be used to determine an initial pre-determined vaporized amount of at least one pharmacologically active agent that would, once administered by an MDI device configured for pulmonary delivery thereof, give rise to an initial pre-selected pharmacokinetic profile and/or an initial pre-selected pharmacodynamic profile of the agent in a particular patient, and can further be used to calibrate and preset similar MDI devices so as to deliver an initial pre-determined vaporized amount to achieve similar consistent initial results.

It is noted that according to some embodiments, while a patient/user may start the pulmonary delivering using an initial pre-determined vaporized amount which has not been determined based on the patient's personal/individual parameters and variables, the method provided herein includes an optional step at which the patient's personal parameters and variables are considered in the determination of the pre-determined vaporized amount. Thus, according to some embodiments, the method may include personalization of the pre-determined vaporized amount that affords the pre-selected PK/PD profile. The personalization step presented may replace a pre-calibration of the MDI device; or as a complementary step after calibration of the MDI device.

Method of Treatment:

The dose unit provided herein, used in an MDI device configured for reproducible and accurate delivery of a therapeutic amount of an isolated bioactive agent or a combination thereof, can be used to treat medical conditions which are treatable by the bioactive agent, which is advantageously administered by pulmonary delivery (inhalation). Such a method of treatment may be advantageous over other methods particularly when the treatment is carried out using an isolated bioactive agent that is difficult to administer by other modes administration, or that other modes administration thereof are ineffective or inefficient.

According to an aspect of some embodiments, there is provided a method of treating a patient suffering from a medical condition which is treatable by pulmonary delivery (inhalation) of at least one pre-determined vaporized amount of at least one isolated bioactive agent.

The method, according to some embodiments, is carried out by pulmonary delivering by voluntary inhalation vapors of the isolated bioactive agent to the patient from a metered dose inhaler device configured to controllably release at least one pre-determined vaporized amount of the agent upon controllably heating a pallet comprising the agent.

According to some embodiments, the pre-determined vaporized amount of the agent is selected so as to exhibit at least one pre-selected pharmacokinetic profile and/or at least one pre-selected pharmacodynamic profile of the agent in the patient.

In some embodiments, the isolated bioactive agent is an isolated cannabinoid such as, but not limited to $\Delta^9$-tetrahydrocannabinol (THC), dronabinol ((-)-trans-THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV), cannabitriol (CBT) and any combination thereof. Other isolated and vaporizable bioactive agents are contemplated in the context of some aspects and embodiments of the disclosure.

According to some embodiments, the isolated bioactive agent comprises a cannabinoid and a terpene and/or a flavinoid.

Non-limiting representative medical conditions, treatable by pulmonary delivering a vaporizable isolated bioactive active agent such as cannabinoids with optional terpenes and/or optional flavinoids, include without limitation, alcohol abuse, amyotrophic lateral sclerosis, anorexia nervosa, anxiety disorders, appetite variations, asthma, atherosclerosis, bipolar disorder, bladder dysfunction, chronic obstructive pulmonary disease (COPD), collagen-induced arthritis, colorectal cancer, Crohn's disease, delirium, digestive diseases, Dravet's Syndrome, drug addiction and craving, dystonia, epilepsy, fibromyalgia, generalized epilepsy with febrile seizures plus (GEFS+), glaucoma, gliomas, hepatitis C, HIV-associated sensory neuropathy depression, Huntington's disease, hyper tension, increased intra ocular pressure, inflammatory bowel disease (IBD), insomnia, irritable bowel syndrome (IBS), lack of appetite, leukemia, migraines, movement disorders, multiple sclerosis (MS), nausea, neurogenic pain, neuropathic pain, nociceptive pain, Parkinson's disease, phantom pain, posttraumatic stress disorder (PTSD), premenstrual syndrome, pruritus, psychiatric disorders, psychogenic pain (psychalgia or somatoform pain), seizures, septic and cardiogenic shock, sexual dysfunction, skin tumors, sleep apnea, spasticity, spinal cord injury, tics, Tourette symptoms, tremors, unintentional weight loss and vomiting.

According to some embodiments, the method is carried out by use of an MDI device which is configured to release a pre-determined vaporized amount such that a deviation of an actual vaporized amount of the isolated bioactive agent, from the pre-determined vaporized amount of the agent, is 20% or less, 15% or less, 10% or less, or 5% or less of the pre-determined vaporized amount.

According to some embodiments, the method is carried out such that a deviation of an actual pharmacokinetic profile from the pre-selected pharmacokinetic profile is 40% or less than of the pre-selected pharmacokinetic profile. Alternatively, the deviation is 35% or less, 30% or less, 25% or less, or 20% or less. It is noted that the deviation can be in the pharmacokinetic profile or in one or more pharmacokinetic parameters composting the profile, e.g., $C_t$ or $C_{max}$. Such deviations are expected to be low, even for isolated bioactive agents for which ingestion and/or injection thereof has been found disadvantageous, due to the low inter-variability of PK parameters obtained when using the dose unit provided herewith in an accurate, consistent and precise MDI device as presented herein.

According to some embodiments, the method is carried out such that a deviation between the perceived PD profile from the pre-selected PD profile at any given time point is 25% or less, 20% or less, 15% or less, 10% or less, or 5% or less. The deviation between the perceived PD profile from the pre-selected PD profile at any given time point can be assessed by determining a PD parameter, as discussed hereinabove. The deviation is expected to be low also due to the low inter-variability of PK parameters discussed hereinabove.

Since the device can be configured to deliver any accurate amount consistently so as to exhibit any pre-selected PD profile in the patient, the device and the method presented herein can effect a pre-selected PD profile which can be finely controlled so as to be:

within a level lower than a minimal level of a therapeutic effect (below the therapeutic window);

ranging within a minimal level of said therapeutic effect to a maximal level of said therapeutic effect in which an adverse effect is acceptable, namely substantially low or not exhibited or not perceived (within the therapeutic window); and within a level higher than a minimal level an adverse effect (above the therapeutic window).

As discussed hereinabove, according to some embodiments, the pre-selected PD profile corresponds to the therapeutic window of the agent in the patient, namely ranges within a minimal level of a desired effect and a level of an undesired effect.

In some embodiments, the pre-selected PD profile ranges between a minimal level of a desired effect to a minimal level of an undesired effect.

In some embodiments, the pre-selected PD profile ranges between a minimal level of a desired effect to a level higher than a minimal level of a undesired effect.

In some embodiments, the pre-selected PD profile ranges between a minimal level of the therapeutic effect to a maximal level of the therapeutic effect in which an adverse effect is acceptable.

At any pre-selected PD profile, the method and device provide high accuracy and reproducibility; hence, according to some embodiments, the deviation of the perceived pharmacodynamic profile from the pre-selected pharmacodynamic profile at any given time point is 25% or less, 20% or less, 10% or less or 5% or less below the pre-selected PD profile, and/or 25% or less, 20% or less, 10% or less or 5% or less above said pre-selected PD profile.

A non-limiting example of a medical condition treatable by pulmonary delivering a vaporizable pharmaceutically active agent, is pain, which is treatable by pulmonary delivery of dronabinol vaporized from a dose unit as presented herein.

Interface and System:

The dose unit (cartridge), inhaler device and methods presented herein are highly suitable for personalization, self-titration, mechanization and automatization of an otherwise complex and challenging mode of administration and treatment of a variety of medical conditions which are treatable by inhalation of one or more bioactive agents; while any personalized treatment protocol according to pharmaceutical guidelines and requirements presents challenges, a reproducible and controllable treatment based on pulmonary delivery of active agents vaporized by heat is a non-trivial task by any standards.

Once the problem of accuracy, consistency and reproducibility have been solved, as done, for example, with the MDI device disclosed herein and in WO/2012/085919; and once the need for calibrating and presetting the device to stay within a desired therapeutic window, based on widely accepted PK/PD experimental parameters has been served, the present inventors have conceived an integrated system that can control the device for pulmonary delivery of isolated bioactive agents using input collected from a variety of sources so as to provide a highly personalized and effective treatment for any given patient, also in real time.

FIG. 6 is a schematic diagram of a system comprising an MDI device, a physician interface and/or a patient interface, according to some embodiments.

In some embodiments, MDI device 901 is configured to communicate with a physician interface 903 and/or with a patient interface 905. In some embodiments, MDI device 901 is configured to receive input from one or both of the interfaces 903 and/or 905. Additionally or alternatively, MDI device 901 is configured to send output to one or both of the interfaces 903 and/or 907.

In some embodiments, communication between the system components is performed via one or more data transfer means such as a USB connection, a cable connection, a wireless connection, and/or any suitable wired and/or wireless communication protocol.

In some embodiments, communication between the system components is performed through one or more communication modules, such as communication module 907 of MDI device 901, communication module 909 of physician interface 903, and/or communication module 911 of patient interface 905.

In some embodiments, MDI device 901 comprises a controller 913, configured, for example, to activate heating of the pallet to thereby vaporize the active agent, control the heating profile and/or activation of heat, control a cartridge feed mechanism of the MDI device, read data from a memory 919 of MDI device 901, control power usage, and/or other functions. In some embodiments, controller 913 communicates with a memory 919. Optionally, memory 919 is configured to store prescription data, personal usage data, patient details, personal PD parameters obtained from the patient, dose, dosing and/or regimen modifications, parameters obtained from the patient in response to a change in a dose and/or regimen, and/or other values or information. In some embodiments, controller 913 activates pulmonary delivery of the active agent according to dose, dosing and/or regimen data stored in memory 919.

In some embodiments, memory 919 is configured to store usage data and/or feedback data from the patient with respect to a specific dose and/or regimen and/or with respect to a pre-selected (desired) PD profile of the active agent in the patient.

In some embodiments, physician interface 903, comprising, for example, one or more of a controller 915, a memory 921 and/or a communication module 909, is configured on a personal computer (tablet computer, laptop computer, desktop computer, or others), a mobile device such as a smartphone, a handheld device, a wearable device, a wrist device or an integrated eyewear device, a clinic or hospital monitor and/or any other suitable device. Optionally, the physician is provided with remote access to MDI device 901. Additionally or alternatively, physician activates MDI device 901 directly. In some embodiments, the physician pre-programs (pre-calibrates or presets) MDI device 901 with a pre-determined vaporized amount (dose, dosing and/or regimen) suitable for an individual patient. In some embodiments, data is sent from physician interface 903 to patient interface 905, for example for instructing the patient or for effecting preset adjustments.

In some embodiments, patient interface 905, comprising, for example, one or more of a controller 917, a memory 923 and/or a communication module 911, is configured on a personal computer (tablet computer, laptop computer, desktop computer, or others), a mobile device such as a smartphone, and/or on MDI device 901 itself.

In some embodiments, patient interface 905 receives an input 929. The input may be received from one or more of the patient, the physician interface, the database server, the MDI device. Examples of various types of inputs may include a dose and/or regimen defined by the physician and received on the physician interface, a current personal PD parameter of the patient, inserted by the patient and/or obtained from the patient, personal usage statistics recorded for example on the database server and/or on the memory of the MDI device, an indication of inhalation duration and/or inhalation volume sensed by the MDI device, and/or other types of input.

In some embodiments, patient interface 905 comprises a display 927.

Optionally, the display is an interactive display, for example a touch screen of a smartphone, a handheld device, a wearable device, a wrist device or an integrated eyewear device.

In some cases, certain functions such as transferring data to the physician, accessing the database to acquire information such as user/patient instructions, and/or other functions are enabled by patient interface 905, while other function such as modifying the pre-determined vaporized amount (dose), dosing and/or regimen, viewing protocols of other patients, and/or other functions are not permitted by patient interface 905. Optionally, the physician sets the patient interface access definitions per an individual patient.

In some embodiments, patient interface 905 and/or MDI device 901 are configured to notify the patient every time a pulmonary delivery (an inhalation) is due. Optionally, the notice is provided automatically based on a scheduled dosing (regimen) stored in the memory. Additionally or alternatively, the notice is set by the patient. Additionally or alternatively, the notice is issued by the physician.

In some embodiments, one or more of the system components communicates with a database server 925, by receiving input from the database and/or sending out information to the database. In some embodiments, the database comprises individual data of the patient, for example including medical history of the patient, data transmitted by MDI device 901, input data from the physician, input data from the patient, and/or other information. Optionally, the database server is configured to perform calculations on the data. In some embodiments, database server 925 comprises collective data, including, for example, one or more of clinical experiment results, results of other patients, research data, and/or other data. Optionally, database server 925 communicates with a plurality of treatment systems being used by various patients. Data from various interactions between patients and the MDI device is collected in the central database, continuously learning individual usage patterns of patients and recommending dose, dosing and/or regimen accordingly. Utilizing the collective user database may improve generating of accurate predictive dose, dosing and/or regimen for current and new patients, improving the overall therapeutic success rate of the treatment.

In some embodiments, according to personal feedback data obtained from the patient using MDI device 901 and/or by patient interface 905, the pre-determined vaporized amount (dose, dosing and/or regimen) is automatically modified by controller 917 of the patient interface and/or by controller 913 of the MDI device to compensate for inadequate settings or misuse of the MDI device, for example in a situation in which the patient does not use the MDI device when instructed to, and/or use the MDI device is carried out at a timing different than the preset regimen. One or more actions may be taken in response, for example postponing the next dose, increasing or decreasing the next dose (and/or following doses), and/or otherwise altering the regimen.

In some embodiments, a patient using MDI device 901 may wish to schedule their dose, dosing and/or regimen in a way in which possible adverse effects least interfere with the patient's daily activities. While certain adverse effects are tolerable in a home setting or at certain time of day, and are an acceptable tradeoff for symptom relief, these adverse effects may be undesirable when the patient is engaged in activities such as driving, attending a meeting, and/or other activities. Optionally, using patient interface 905 and/or by directly activating MDI device 901, the patient schedules a dose, dosing and/or regimen in a manner that least interferes with their planned activities.

Additionally or alternatively, MDI device 901 and/or patient interface 905 are configured to actively impose a certain dose and/or regimen, for example based on input from the patient. In an example, the patient inserts their planned daily activities and timing of those activities, and the dose, dosing and/or regimen is automatically modified accordingly. Optionally, the dose, dosing and/or regimen is automatically modified to ensure that the patient is in a suitable condition to perform the planned activity, for example ensuring that during driving the level of an adverse effect is relatively low or not perceived.

In some embodiments, the patient may voluntarily modify the dose, dosing and/or regimen, for example using patient interface 905. Optionally, the extent of modifications is limited, to prevent a condition in which the patient is at risk, for example preventing overdosing.

In some embodiments, the patient may simply use MDI device 901, even when not specifically instructed to. In such a case, the next dose and/or regimen may be automatically modified in response to the usage. Optionally, the patient is notified about modifications in the dose and/or regimen through patient interface 905.

Additionally or alternatively, the physician is notified about such changes, for example through physician interface 903.

FIG. 7 is a flowchart of a method for prescribing a regimen to a patient using an MDI device for delivery of at least one active agent, according to some embodiments.

In some embodiments, a physician may decide to treat a patient by effecting a pulmonary delivery of one or more active agents by an MDI device (1001).

In some embodiments, patient data such as one or more of, for example, PK variables (e.g., age, gender, BMI etc.), pathophysiological status, pharmocogenetic and/or pharmacogenomic variables and/or other parameters are inserted to the system (1003), for example by the physician and/or other clinical personnel. Optionally, the patient's parameters and personal variables are inserted using the physician interface.

In some embodiments, a suggested dose, dosing and/or regimen is generated (1005). Optionally, the dose, dosing and/or regimen is generated automatically, for example by software of the physician interface. Additionally or alternatively, the dose, dosing and/or regimen is planned by the physician. In some embodiments, the dose, dosing and/or regimen is generated by matching the inserted patient data to a predefined dose and/or regimen using data from a database, or according to personal feedback data, or for example according to a look up table.

In some embodiments, a simulation of an expected PK/PD profile of the patient for the selected dose, dosing and/or regimen is produced (1007). In some embodiments, an expected PK/PD profile, including for example therapeutic effects and/or adverse effects is simulated. In some embodiments, by correlating between the pharmacodynamic profile and/or pharmacokinetic profile and the patient's personal data, a therapeutic window is selected. Optionally, the PK/PD profile simulations and/or the pre-selected therapeutic window are graphically displayed to the physician, for example on a display of the physician's interface. When considering the simulations, a physician may decide to modify the dose, dosing and/or regimen to better suit (personalized) it to the patient (1009). In some cases, the physician may decide to change proposed dose and/or regimen parameters such as one or more of dose, dosing, regimen or total treatment duration, and/or other treatment parameters.

In some cases, treating includes administering two or more bioactive agents from one, two or more pallets, simultaneously or sequentially, to obtain a desired therapeutic effect in the patient. The system, according to some embodiments, provides the ability to use the MDI for delivering more than one pharmaceutically active agents (from one or more pallets) at any ratio or pre-determined vaporized amounts so as to exhibit a pre-selected PD profile (e.g., maintaining an individual patient within the therapeutic window calculated per the patient). In some embodiments, different doses are selectively administered according to a regimen so as to prevent adverse effects while still alleviating symptoms.

In some embodiments, the selected (and optionally refined) dose, dosing and/or regimen is prescribed to the patient (1011).

In some embodiments, as a follow up and over a time period in which the patient is treated (e.g., over several hours, over a day, over a week, over a month, and/or intermediate, longer or shorter periods), the physician receives one or more indications such as indications relating to the patient's general usage of the device, indications relating to dose, dosing and/or regimen administered to the patient, dose units used by the patient, one or more personal PD parameters of the patient, for example relating to the presence of adverse effects, such as the psychoactive level and/or indications relating to the symptom intensity such as the pain level, and/or a level of one or more biomarkers and/or other indications (1013). Optionally, one or more indications are provided in real time. Additionally or alternatively, the indications are provided at the end of a pulmonary delivery of the agent. Additionally or alternatively, the indications are provided on demand of the physician.

Additionally or alternatively, the patient decides when to send indications to the physician.

In some embodiments, the indications are transmitted to the physician by the MDI device and/or by the patient interface, automatically and/or in response to an instruction from the physician and/or the patient. Optionally, one or more indications are stored in the database for future reference.

In some embodiments, based on the provided indications, the dose, dosing and/or regimen is adjusted or otherwise modified (1015). Optionally, modification is performed in real time. In some embodiments, a specific dose, dosing and/or regimen is modified, optionally in real time. In some embodiments, the dose and/or regimen is modified while taking into account upper and lower PD parameter limits defined individually per the patient. An upper limit may allow dose, dosing and/or regimen above which substantial adverse effects are present. A lower limit may allow dose and/or regimen below which a symptom, which was intended to be treated by delivery of the active agent, is not sufficiently alleviated.

FIGS. 8A-D are a schematic diagram (FIG. 8A) and print screens (FIGS. 8B-D) of a physician interface for selecting and prescribing a dose, dosing and/or regimen to a patient, according to some embodiments.

Figure 8A:
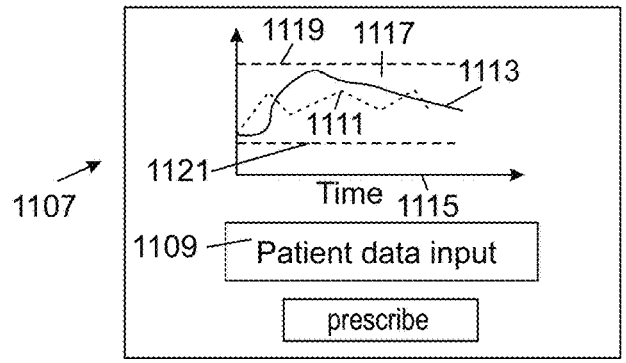

FIG. 8A illustrates a general display 1107 of a physician interface. In some embodiments, patient data is inserted by the physician through input 1109.

In some embodiments, a graphical display of an expected and/or pre-selected pharmacokinetic profile 1111 and/or an expected and/or pre-selected pharmacodynamic profile 1113 is presented to the physician. Optionally, one or more of the profiles are shown, separately or together, with respect to a time series 1115, including, for example, a duration (e.g., an hourly scale) over which a patient is treated. In some embodiments, a therapeutic window 1117 is defined, setting an upper limit 1119 and a lower limit 1121. In some embodiments, the dose, dosing and/or regimen is selected so as to have the expected and/or pre-selected PK/PD profiles fit within a range of the therapeutic window 1117.

In some embodiments, a limit is defined as a constant value, presented as a straight line, for example as shown in FIG. 8A. Alternatively, a limit may comprise a varying set of values, and be presented as a curved line. For example, lower limit 1121 represents a desirable therapeutic effect, upper limit 1119 represents an acceptable adverse effect, and a higher $C_{max}$ threshold of the pharmacokinetic profile may be set for an initial part of the treatment, for example to accelerate symptom relief, and the $C_{max}$ threshold may decrease as the treatment continues as desired. In some embodiments, a dose and/or regimen is selected and/or adjusted to achieve an initial buildup of the active agent in the patient, for example at an initial part of the treatment, and then to provide on-going dosing for maintaining the patient in a steady state (maintenance dosing). In general, an initial buildup of the agent is based on a relatively large amount of the agent compared to the amounts given at the maintenance dosing.

In some embodiments, for example when refining a pre-determining vaporized amount of the agent (dose, dosing and/or regimen) for an individual patient, a physician may perform one or more of raising and/or lowering of limit 1119 and/or limit 1121, raising and/or lowering the peaks of profile 1113 and/or of profile 1111, extending and/or shortening a treatment duration along the time axis, and/or other modifications.

It is noted that the graphic representation is shown herein as an example, and that various graphic representations such as a bar graph may be used. In some embodiments, the profile 1111 and/or profile 1113 may be presented in a non-continuous manner, for example as a set of points.

Figure 8B:
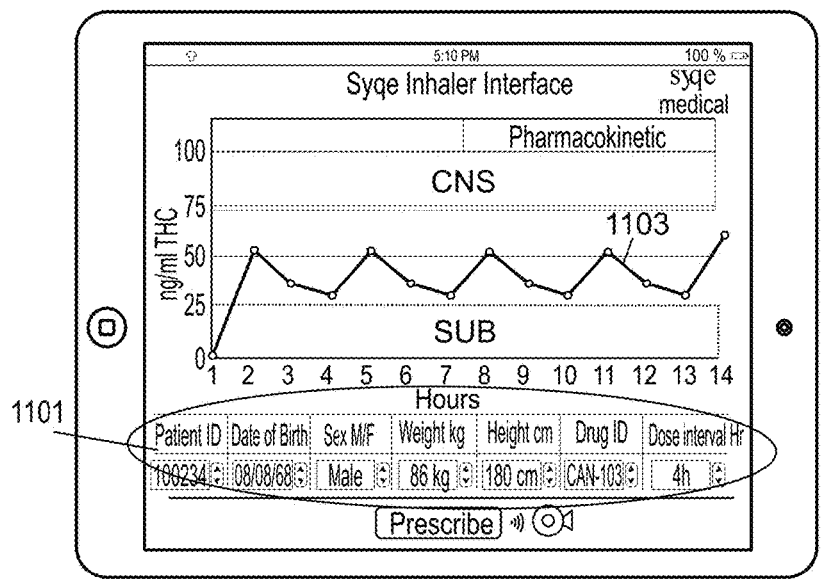

FIG. 8B illustrates a simulation of an expected pharmacokinetic profile of a patient using a pre-determined vaporized amount delivered according to a pre-determined regimen, according to some embodiments. In this example of a physician interface screen, a physician may fill in patient data 1101 (such as gender, weight, height, administered drug, patient ID and/or other data), and obtain a pharmacokinetic profile extrapolation of the individual patient, as shown for example by graph 1103, simulating the plasma concentration of an active agent in the patient over time.

Figure 8C:
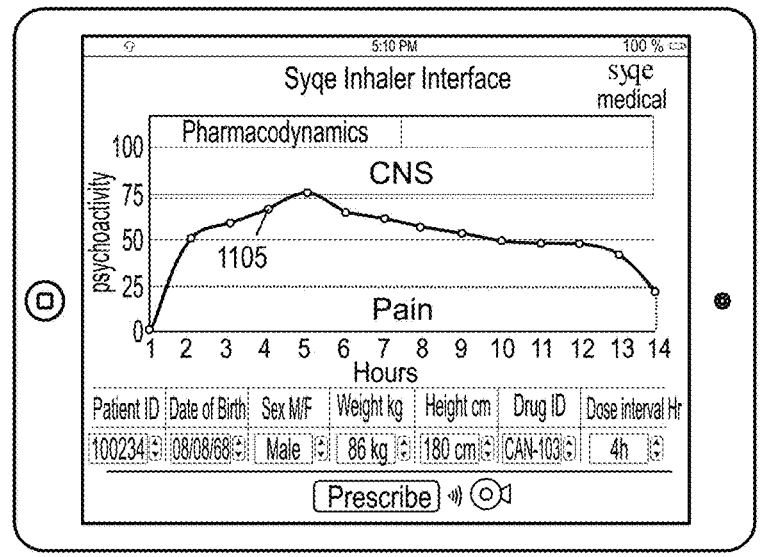

Similarly, FIG. 8C illustrates an expected pharmacodynamic profile extrapolation 1105 of the individual patient, showing an adverse effect level in the patient over time.

Figure 8D:
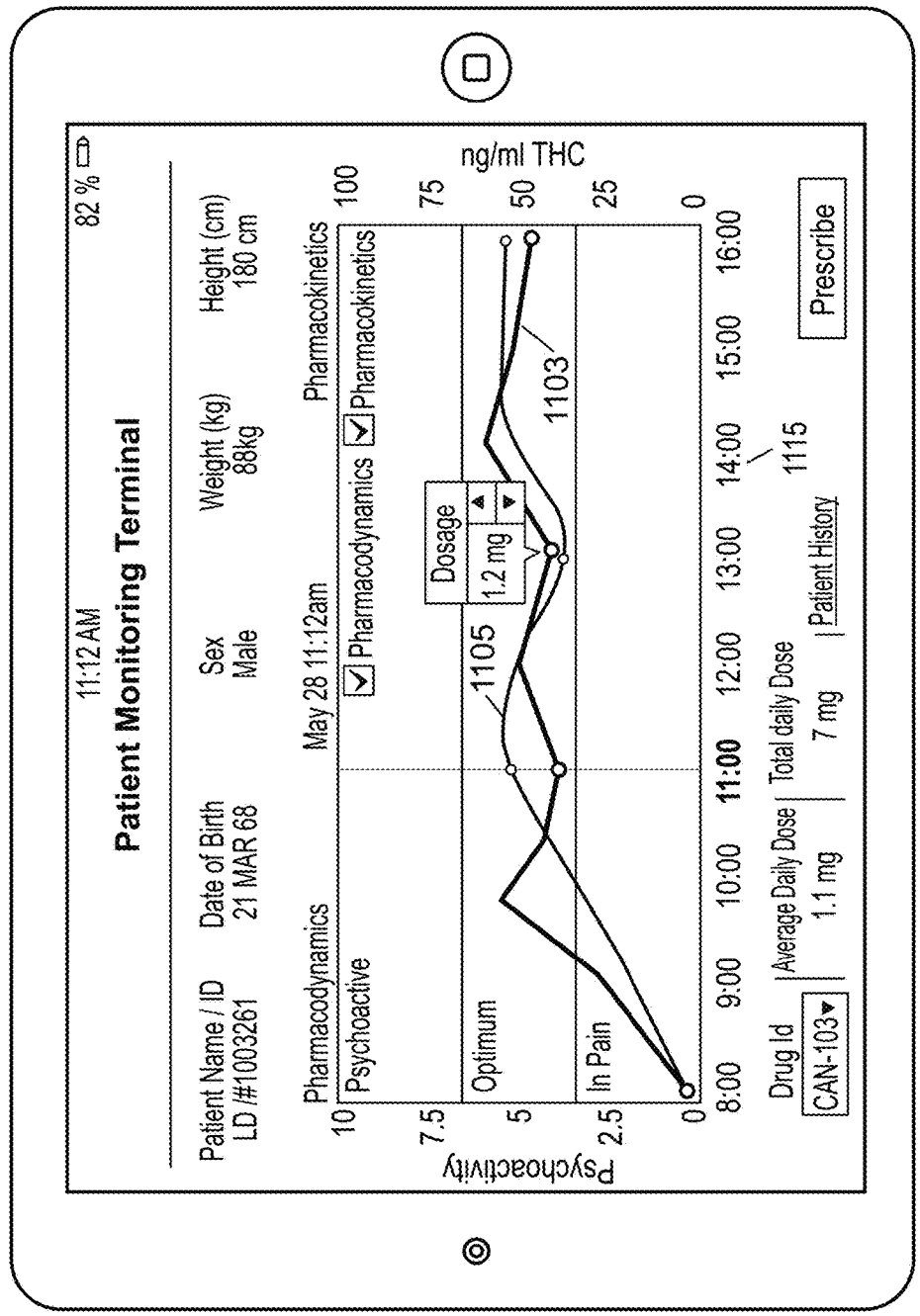

FIG. 8D shows a physician interface print screen, according to some embodiments. A simulated pharmacokinetic profile is represented by graph 1103 and a simulated pharmacodynamic profile is represented by graph 1105, which are displayed on a time series axis 1115, in this example representing an 8-hour period. A pharmacodynamic parameter scale of the patient is visually divided into sections indicating, for example, an "in pain" state (below a therapeutic effect level), indicating "optimum" state (within the therapeutic window) and indicating, for example, "psychoactive" state (above an adverse effect level) as defined per the individual patient, and the simulated PK/PD profiles as graphs are shown with respect to these sections. In this simulation, a first dose is provided at 8:00, resulting in a change of both the pharmacodynamic and pharmacokinetic parameters, going up from the "in pain" section into the "optimum" section. A second dose, provided at 11:00, is shown to maintain the patient within "optimum" (the therapeutic window).

FIG. 9 is a flowchart of a method for obtaining feedback data from a patient and modifying/adjusting a dose and/or regimen accordingly, according to some embodiments.

In some embodiments, a personal PD parameter of the patient is obtained (1201). In some embodiments, the PD parameter relates to an adverse effect such as a psychoactive level, a therapeutic effect such as a pain level, and/or a change in any of those levels thereof. The PD parameter may include an absolute quantification of the level, and/or a relative quantification of the level, assessed, for example, with respect to a level measured before a delivery of single dose and/or before a delivery of dosing and/or regimen. The PD parameter may be obtained before, during and/or after a delivery of single dose and/or before, during and/or after a delivery of dosing and/or regimen and/or before, during and/or after a general time period over which treatment is provided to the patient.

In some embodiments, the PD parameter is provided directly by the patient, for example using the patient interface. In some embodiments, the patient can manually adjust a visual representation of the PD parameter, based on a personal determination of the level of the PD parameter. In an example, the patient may raise or lower a bar on a graph indicating a pain level, for example on a touch screen of a cellular phone and/or any other personal device on which the patient interface is configured.

In some embodiments, patients who are unable to articulate levels of the PD parameter may utilize an interactive set of tools to assist them in determining their current level of the PD parameter, for example as further described herein.

Additionally or alternatively to a conscious, personally perceived PD parameter indicated by the patient, a personal PD parameter such as a biomarker is obtained by the patient interface and/or by the system, for example using a sensor. In some embodiments, one or more standard components of a cellular phone and/or personal computer on which the patient interface is configured as acts as a sensor for obtaining the parameter. Some components which may be used as sensors for obtaining PD parameters from the patient may include: a touch screen, may be used for example to assess dexterity, eye-hand coordination, and/or a memory and cognition state; a gyroscope, accelerometer, proximity sensor and/or gesture sensor such as IR sensor may be used, for example, to assess motor skills; a camera and/or light source may be used, for example, to detect visual tracking, saccade variance, eye vascular expansion, pupil dilation and/or pulsation; an RGB illumination may be used, for example, to assess environmental perception; a magnetometer and/or GPS may be used, for example, to assess orientation; a speaker and/or microphone may be used, for example, to assess auditory and/or vocal skills; a temperature and/or humidity sensor may be used, for example, to assess a body temperature.

In some embodiments, the MDI device is configured to obtain personal feedback data. In an example, the MDI device comprises a flow sensor and/or a pressure sensor. Optionally, a breathing related indication of the patient is obtained using the flow and/or pressure sensor. In some embodiments, the sensor is adapted to detect a volume of inhalation. Since a correlation may exist between inhalation volume and a PD parameter, such as a pain level, in some embodiments, a flow and/or pressure measurement is initiated to determine a PD parameter in the patient.

Once one or more personal PD parameters are obtained, the dose and/or regimen may be modified accordingly (1203). In some embodiments, the dose and/or regimen is modified, on one hand, to improve or otherwise change a condition of the patient based on the provided indication, and, on the other hand, to achieve a pre-selected pharmacodynamic profile, such as maintaining the patient within the therapeutic window—between a lower limit of a therapeutic effect that provides symptom relief, and a higher limit of an adverse effect in which the adverse effect level is still tolerable. In some embodiments, the MDI device can be configured such that when below a minimal therapeutic effect, input by the patient may increase the dose and/or adjust the regimen in frequency and/or in quantity. Optionally, the dose and/or regimen is modified to obtain a level above a minimal therapeutic effect.

Additionally or alternatively, the dose and/or regimen is modified as much as the maximal level of an adverse effect permits.

FIGS. 10A-E are print screens of a patient interface (FIG. 10A, FIG. 10C, FIG. 10E), and graphic representations of an expected pharmacodynamic and pharmacokinetic profiles of the patient before and after input of personal PD parameter of the patient is obtained (13B and 13D respectively), according to some embodiments.

FIG. 10B presents a calculated 3-hours regimen for a certain patient (Patient X, 35 years old and has a BMI of 22). According to an example for a calculated regimen, to maintain Patient X within the therapeutic window for 3 hours effected a PK profile presented by the red curve in FIG. 10B, Patient X is required to be subjected to pulmonary delivery of an active agent using an MDI device according to some embodiments, at the following times and doses: 00 minutes-1.2 mg; 10 minutes-1.0 mg; 60 minutes-0.5 mg. The blue curve represents an example for a calculated PD profile at the indicated doses. As seen, the calculated regimen maintains Patient X within limit levels, namely below the adverse effect level and above the therapeutic effect level, namely at a therapeutic window 1303 ranging between 2.5 to 7.5 on the exemplified adverse psychoactivity effect scale.

In FIG. 10C, during and/or after treatment, Patient X indicates a wish to alter the adverse effect limit, for example by raising a psychoactivity level bar 1301 on the patient interface screen. By raising the bar, the patient may indicate he is willing to increase the tolerable level of an adverse psychoactive effect. The therapeutic window, as shown in FIG. 10D, is then redefined based on the patient's input—for example, the window is narrowed to a range of 2.5 to 5 on the psychoactivity scale.

The currently administered dose and/or regimen may then be modified accordingly. For example, a pre-determined vaporized amount that is planned for pulmonary delivering at, for example, 60 minutes from the initial pulmonary delivering is reduced from 0.5 mg to 0.3 mg, in attempt to lower the level of an adverse effect (psychoactive effect) the patient is experiencing.

In some embodiments, the dose and/or regimen is automatically modified, based on the patient's input. Additionally or alternatively, the patient input and/or the simulated profiles are transferred, automatically and/or on demand of the patient, to the physician, and the physician modifies the regimen.

It is noted that the sensitivity of a patient to the therapeutic and/or an adverse effect may vary throughout the day for a patient, e.g., demonstrating higher pain sensitivity in the evening, diminished cognitive abilities in the morning, thus less susceptive to a therapeutic effect in the evening, or more susceptive to an adverse effect in the morning.

Additionally or alternatively to an adverse effect level, a patient may indicate their therapeutic effect level and/or other conditions, and the dose and/or regimen will be modified accordingly.

Figure 10E:
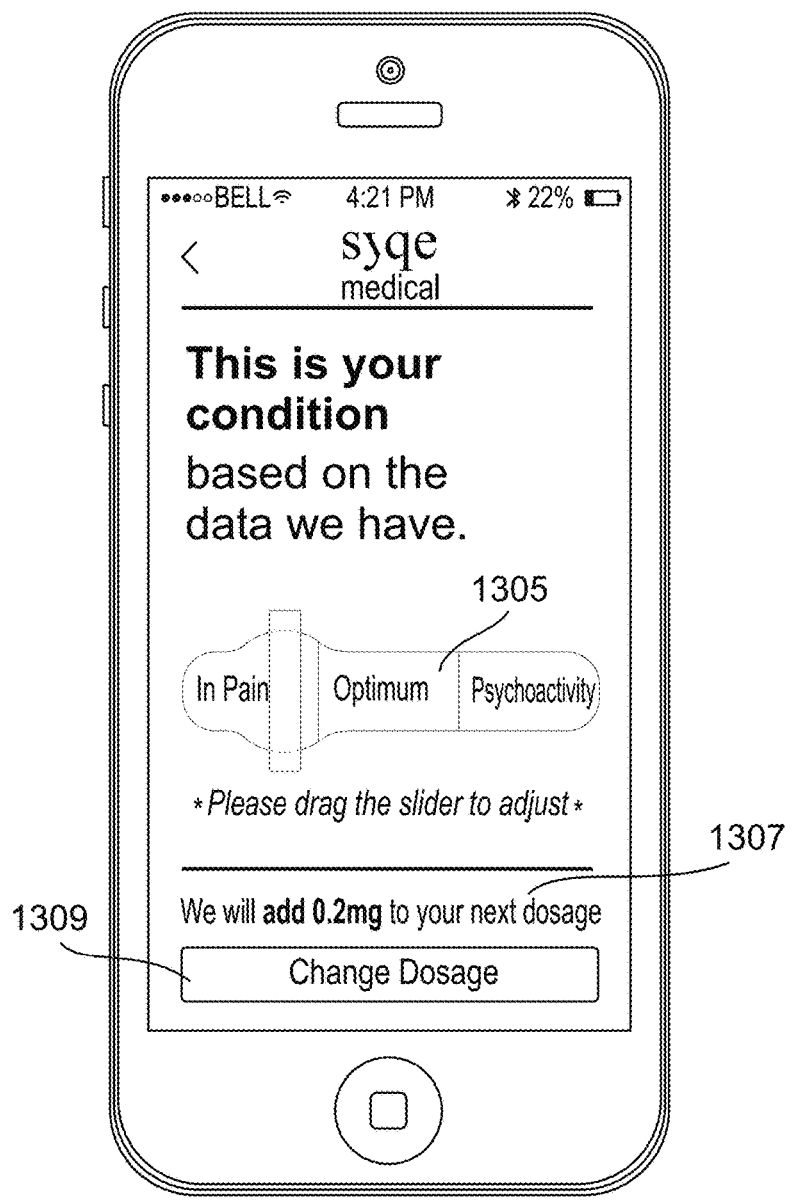

FIG. 10E shows an example for a patient interface application including an adjustable slider 1305, moveable by the patient. In some embodiments, the application presents to the patient an estimation of a current condition, calculated based on one or more of following: the pre-determined dose, dosing and/or regimen, previous input obtained from the patient, for example including biomarkers and/or other direct and/or indirect personal PD parameters, treatment and effect history for the individual patient, usage record of the patient, a medical condition of the patient, information from a collective database, and/or other information.

During treatment and/or following treatment, the patient may drag the slider to reflect their perceived PD profile. For example, if the patient experiences a complete therapeutic effect (e.g., patient is no longer in pain), the patient may move the slider to an "optimal" state (e.g., to a "psychoactive" state).

Using input obtained from the patient, the patient interface may automatically modify the next dose and/or regimen. In some embodiments, an indication of the modification 1307 is displayed to the patient, for example notifying the patient that the next dose is increased in amount. Optionally, the application is configured to request confirmation 1309 from the patient to change the dose, dosing and/or regimen.

In some embodiments, the input from the patient and/or the modified settings are automatically transferred to the physician interface. In some cases, the physician may decide to manually change the newly defined dose and/or regimen settings.

FIG. 11 is a flowchart of a method for measuring one or more biomarkers using a personal portable device and/or using the MDI device, and modifying the dose and/or regimen accordingly, according to some embodiments.

In some embodiments, one or more biomarkers are measured (1401). In some embodiments, the biomarkers indicate the existence and/or extent of adverse effects in a treated patient. Optionally, the biomarker measures are used for determining a therapeutic window for an individual patient, and/or for controlling the dose and/or regimen to maintain the patient within the therapeutic window.

Adverse effects, such as cognitive impairment and other psychoactive effects, may differ between patients given various genetic and biological traits. Therefore, in some embodiments, individual biomarkers, such as CNS biomarkers, are obtained from the patient, using, for example, one or more sensors in the system, and/or one or one more sensors configured in the patient interface device, such as cellular phone sensors for example as described hereinabove.

Some non-invasive biomarker assessment methods may include one or more of saccadic eye movement assessment (such as saccadic movement), memory testing, adaptive tracking, finger tapping assessment, body sway assessment, visual analog scale match, and/or other assessment methods.

In some embodiments, various known in the art non-invasive biomarker tests such as cognitive tasks may be performed, including, for example, reaction time, attention, visuospatial span, name recall, narrative recall, face recall, name—face association, construction, verbal fluency, object naming, implicit memory, logical reasoning and/or other cognitive tasks.

In some embodiments, the biomarker measures are communicated to the physician (1403). Optionally, the PD parameter measures are stored in a memory of the MDI device and/or a memory of the patient interface. Additionally or alternatively, the PD parameter measures are uploaded to a database. Optionally, the PD parameter measures are compared to PD parameter measures stored in the database, including, for example, previous PD parameter measures of the individual patient, PD parameter measures of other patients, PD parameter measures from literature, etc.

In some embodiments, the dose and/or regimen is modified according to the PD parameter measures (1405).

FIGS. 12A-C are print screens of a patient interface comprising various applications for obtaining PD parameter data and/or for assisting a patient in determining a vaporized amount of the agent (dose and/or regimen), according to some embodiments.

In the application shown herein by way of example, which may be installed on a personal portable device such as a cellular phone and/or a tablet computer, a patient interactively performs one or more tasks, which may be incorporated as a part of a game or the like, based on a personal PD parameter which can be assessed based on the task. In some embodiments, an adverse effect level, such as a psychoactive level of the patient, is automatically deduced by the application. Additionally or alternatively, the application assists the patient in articulating their perceived therapeutic and/or adverse effect, which can then be provided as an input to the system.

The tasks shown herein for example include tracking a target with a finger (FIG. 12A), visually tracking a target (FIG. 12B), aligning a target (FIG. 12C).

Other applications may include for example various personal PD parameter measurements using activities and methods known in the art, such as simulated driving, card sorting, arithmetic skill testing, time estimation, symbol copying, adaptive tracking, reaction time, picture and/or wording skills, and/or other applications, for example as described hereinabove.

FIG. 13 is a schematic diagram of an inhaler device configured to provide automated controlled pulmonary delivery of one or more active agents, according to some embodiments.

In some embodiments, device 1601 comprises dose unit dispenser 1603, e.g., a dispenser for the pallet that contains the pharmaceutically active agent and allows the pharmaceutically active agent to be vaporized therefrom. In some embodiments, the dose unit dispenser comprises, or is in communication with, a source of at least one pallet from which the active agent originates, and a mechanism for processing the dose unit to obtain a deliverable active agent, for example as described hereinabove.

The pallet may comprise various forms, such as, for example, a solid bulk, solid particles or a powder. Optionally, the pallet is contained within a cartridge, a capsule, and/or other containers. In some embodiments, the processing mechanism includes one or more of, for example, heating (e.g., for vaporizing), turning to aerosol, causing a chemical reaction, for example by mixing with other materials, releasing a bioactive agent from a container such as by breaking open a capsule, pressure propellant, mobilizing and/or other types of processing. Alternatively, the active agent is already in a ready to use form and does not require any processing before delivering to the user by heating the pallet.

In some embodiments, inhaler device 1601 is an MDI device which comprises an input 1605. Optionally, input 1605 is configured to receive data pertaining to a dose and/or a regimen according to which the active agent will be delivered to the patient. Additionally or alternatively, input 1605 is configured to receive one or more indications from a sensor (not shown in FIG. 13), comprised within device 1601 and/or configured externally to device 1601.

In some embodiments, inhaler device 1601 comprises a controller 1607, configured to initiate and/or modify and/or cease the pulmonary delivery of the pharmaceutically active agent. In some embodiments, controller 1607 operates dose unit dispenser 1603, for example activating heating of the pallet by a heating element, such as a resistive heating element. In some embodiments, controller 1607 activates delivery of a pre-determined vaporized amount of the agent, such as the dose and/or regimen received as input. In some embodiments, controller 1607 controls the flow of the active agent, for example by activating one or more valves. In some embodiments, the controller is adapted to release the agent based on a current flow rate.

In some embodiments, inhaler device 1601 comprises an output 1609.

Optionally, output 1609 is configured as a mouthpiece engageable by the patient. Alternatively to a mouthpiece, output 1609 may be configured as a breathing mask, a pacifier-like attachment for infants, and/or other structures suitable for delivering the flow of vapors to the patient.

In some embodiments, components of device 1601 such as the dose unit dispenser and/or the controller and/or other components are contained within a housing 1611. Optionally, the housing is shaped and sized to be used as a handheld device.

In some embodiments, MDI device 1601 comprises a flow control mechanism.

Optionally, the flow of vapors is controlled using one or more valves. In some embodiments, the flow is selected and/or modified per the individual patient, for example by timing the delivery and allowing flow of the active agent to the patient only during inhalation of the patient, indicated for example by a sensor incorporated in the device. In some embodiments, the device is configured to modify the flow to allow the patient to instinctively identify when to cease inhalation, inhale deeper, and/or otherwise change the breathing rhythm and/or intensity. In an example, a pulse of increased flow volume is delivered by the device to indicate to the patient to cease inhalation.

In some embodiments, the flow is selected and/or modified to reduce an amount of active agent that remains trapped within the outflow tract of the device, and is not delivered to the patient. In some cases, the amount of trapped active agent is reduced to a known, predefined amount by controlling the flow.

In some embodiments, the flow is controlled by controller 1607. Optionally, the flow is controlled according to data received on input 1605, data acquired by a sensor, and/or other indications.

A potential advantage of a device comprising a flow control mechanism which is operable per an individual patient may include improved accuracy of delivery to the patient, with respect to timing and/or pre-determined vaporized amounts of active agent delivered by the device, improving the performance of the system/MDI device.

FIG. 14A is a schematic diagram of a configuration of an inhaler device 1701, which may be an MDI device, according to some embodiments.

In this configuration, dose unit dispenser 1703 comprises dose unit (cartridge) 1705, a heating element 1707, and a feeder 1709 which moves the dose unit relative to the heating element 1707, for example to be in contact with or in proximity to the heating element.

In some embodiments, the heating element is configured to provide localized heating, for example by conduction, convection and/or radiation. In some embodiments, a pallet is heated sufficiently quickly to a temperature suitable for forming vapors of a vaporizable pharmaceutically active agent contained therein. In some embodiments, the pallet is organized as a moving element which can be selectively and/or locally activated. Optionally, the pallet is organized into compacted shapes. Optionally, each shape represents a pre-determined vaporized amount.

In some embodiments, the vapors released from the pallet collect within a vapor chamber 1711, from which they travel to the patient through an outflow tract.

Optionally, a valve 1713 is positioned along the tract to control the rate of flow.

In some embodiments, device 1701 comprises a mouthpiece 1715 from which the vapors are delivered to the patient in response to inhalation. Alternatively, mouthpiece 1715 can be attached to other elements, for example, to a mask and/or nasal cannula, optionally with supplemental oxygen, for example, to deliver therapy to debilitated patients. Optionally, mouthpiece is in fluid communication with valve 1713.

In some embodiments, device 1701 comprises a power source 1717, for example a battery, a manually wound spring, and/or a wall socket plug.

In some embodiments, device 1701 comprises a controller 1719, for example as described hereinabove, configured to control one or more of valve 1713, power source 1717, and/or the dose unit dispenser 1703 as a whole and/or separately control the components of the dose unit dispenser. In some embodiments, controller 1719 verifies that a dose unit is authorized for use.

In some embodiments, controller 1719 is in communication with memory 1721, which can be read by the controller and/or be written in.

FIG. 14B shows a dose unit 1723, comprising a plurality of discrete pallets 1725. Each pallet 1725 contains one or more sections or areas 1727 intended for vaporization one or more isolated bioactive agents, enclosed within a heating element 1729 which functions as the housing of the pallet. In some embodiments, heating element 1729 is shaped as cage-like a net of wires which encases the pallet. In some embodiments, to vaporize the active agent, electrical current is passed through heating element 1729, heating the loaded pallet contained within the specific individual dose unit. The produced vapors are optionally collected in a vapor chamber and delivered to the patient.

A potential advantage of individually heated dose units may include more accurate control over the pre-determined vaporized amounts of bioactive agent being delivered to the patient, for example in comparison to a moving strip of dose units heated by a stationary heating element. Individual loading and heating of a specific dose unit at certain timing may improve the accuracy of the MDI device.

FIG. 15 a flowchart of a method of treating an individual patient using a system according to FIG. 6, while maintaining the patient within a therapeutic window, according to some embodiments.

In some embodiments, the MDI device is programmed with a pre-determined vaporized amount (dose and/or regimen) (1801). Optionally, the dose and/or regimen is set in the inhaler device by the physician, manually (such as by activating buttons on the device itself) and/or using the physician interface. Additionally or alternatively, the dose and/or regimen is set in the MDI device according to instructions sent from the patient interface.

In some embodiments, the device is activated to deliver the active agent to the patient (1803). In some embodiments, direct and/or indirect feedback data from the patient is obtained in real time (1805). Optionally, feedback data is obtained over a pulmonary delivering (an inhalation session). A treatment may typically start with a pulmonary delivery, and end between 5-20 minutes thereafter, for example when the pre-selected pharmacodynamic profile has fully manifested for the active agent and/or at a later time. Additionally or alternatively, feedback data is obtained over a series of pulmonary deliveries, for example over a time period of 1 hour, 3 hours, 5 hours, 9 hours, 12 hours or intermediate, longer or shorter time periods. A protocol may include for example 5-10 pulmonary deliveries per day, in time intervals ranging between 15-180 minutes between successive pulmonary deliveries.

In some embodiments, the feedback data which is obtained from the patient includes personal PD parameters such as therapeutic effects, for example symptom intensity, and/or adverse effects, for example a psychoactive state of the patient.

In some embodiments, the patient interface interacts with the patient to obtain the feedback data. In some embodiments, questions to the patient relating their current state are displayed on a screen, and the patient answers the questions. Such a question may be presented, for example, in the form of a bar indicating a pain level, for example, which the patient raises and/or lowers. Additionally or alternatively, feedback data is obtained by one or more applications, such as games, which the patient interacts with. Optionally, non-invasive biomarkers levels are estimated by analyzing the patient's input when interacting with the user interface. Additionally or alternatively, feedback data from the patient is obtained by measuring various biomarkers using one or more sensors, for example by utilizing components of a smartphone, a handheld device, a wearable device, a wrist device or an integrated eyewear device, to act as non-invasive biomarker sensors.

In some embodiments, the personal PD parameters are obtained periodically, for example semi-daily, daily, weekly, monthly, per demand such as before a dose and/or a series of doses, before and/or after alterations in dosing and/or regimen, or others.

In some embodiments, in response to the PD parameters, a dose and/or regimen is modified (1809). Optionally, the dose and/or regimen is modified to achieve a desired effect, for example reduce pain level of the patient, while maintaining the patient within a therapeutic window. In some embodiments, the dose and/or regimen is iteratively modified by the patient interface. Modifications may take place a plurality of times, for example during, between or after one or more pulmonary deliveries, and/or over a total treatment time period (days, weeks, months, years) over which the patient is treated. The modification is limited by safety cutoffs, such as doses which may put the patient at risk.

In some embodiments, the patient interface and/or the inhaler (or MDI) device remind the patient to perform one or more pulmonary deliveries (1811). Such a reminder may be provided as a visual signal (for example light indication), a sound, a vibration, a notification on a portable/handheld device, e.g. smartphone, a handheld device, a wearable device, a wrist device or an integrated eyewear device, or a combination thereof.

In some embodiments, usage data of the patient is recorded and stored in the MDI device memory and/or in the patient interface memory. Optionally, the delivery of the active agent is modified, potentially in real time, according to usage data. For example, in a case in which the patient missed one or more pulmonary deliveries, the dose and/or regimen may be automatically modified to set a delivery of, for example, an increased amount of active agent in the following one or more pulmonary deliveries.

In some embodiments, any one or more of the actions described in 1801-1811 may be repeated. Advantageously, obtaining personal PD parameters and/or usage data from the patient repetitively may provide for ongoing adjustment of the dose and/or regimen, providing a flexible, precise and accurate personalized treatment to the patient based on an actual effect of the treatment on the individual patient.

It is expected that during the life of a patent maturing from this application many relevant dose units for vaporizing and delivering by inhalation isolated bioactive agents will be developed and the scope of the term dose unit is intended to include all such new technologies a priori.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 µm" is intended to mean "about 10 µm".

As used herein, numerical ranges preceded by the term "about" should not be considered to be limited to the recited range. Rather, numerical ranges preceded by the term "about" should be understood to include a range accepted by those skilled in the art for any given element in microcapsules or formulations according to the present disclosure.

The term "about" as used herein means within an acceptable error range for a particular value as determined by one of ordinary skill in the art, which will depend in part on how the value is measured or determined, i.e., the limitations of the measurement system. For example, "about" can mean a range of up to 10%, more preferably up to 5%, and still more preferably up to 1% of a given value. Where particular values are described in the application and claims, unless otherwise stated, the meaning of the term "about" is within an acceptable error range for the particular value.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment may include a plurality of "optional" features except insofar as such features conflict.

Throughout this application, various embodiments may be presented in a range format. It should be understood that the description in range format is merely for convenience and brevity and should not be construed as an inflexible limitation on the scope of an invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

All values of measurable parameters are assumed measured under standard temperature and pressure conditions or the like unless noted otherwise.

It is appreciated that certain features of an invention, which are, for clarity, described in the context of separate embodiments, may also be provided in combination in a single embodiment. Conversely, various features of an invention, which are, for brevity, described in the context of a single embodiment, may also be provided separately or in any suitable subcombination or as suitable in any other described embodiment. Certain features described in the context of various embodiments are not to be considered essential features of those embodiments, unless the embodiment is inoperative without those elements.

Various embodiments and aspects of the present disclosure as delineated hereinabove and as claimed in the claims section below find experimental support in the following examples.

EXAMPLES

Reference is now made to the following examples, which together with the above descriptions illustrate some embodiments of in a non-limiting fashion.

Example 1

A piece of fritted glass of porosity 30 (laboratory standard), having pallet dimensions suited to fit into the pallet frame or housing, was used as a unified air-permeable matrix.

A solution of 50 mg of isolated and purified CBD in 50 microlites ethanol was prepared. The solution was poured over the air-permeable matrix such that the solution remained encompassed and soaked in the matrix without leach.

The loaded air-permeable matrix, namely the pallet, was placed in a dryer to evaporate the ethanol at a temperature lower than the boiling point of CBD, such as 100° C.

Once ethanol was evaporated, as was assessed by arriving at a constant weight of the pallet, the pallet was ready to continue with mounting of the dose unit. Once the pallet is positioned in the frame of the dose unit, the mesh is fused to the dose unit frame by means of heat press (melting the frame and overlapping the mesh), ultrasonic welding or optionally any biocompatible glue.

CBD has a boiling point of 180° C. A short time was provided to vaporize and to inhale the drug (about 3 seconds total), so that most if not all of the drug may be vaporized and inhaled in a single inhalation by most contemplated users. The pallet was quickly heated to above 180° C. but below the combustion temperature of the air-permeable matrix material, the frame material and CBD.

Example 2

A piece of ceramic of porosity 30 (laboratory standard), having pallet dimensions suited to fit into the pallet frame or housing, is used as a unified air-permeable matrix.

A solution of 20 mg of pure dronabinol in 50 microlites ethanol is prepared.

The solution is poured over the air-permeable matrix such that the solution remains encompassed and soaked in the matrix without leach.

The loaded air-permeable matrix, namely the pallet, is placed in a dryer to evaporate the ethanol at a temperature lower than the boiling point of dronabinol, such as 100° C.

Once ethanol is evaporated, as can be assessed for example by arriving at a constant weight of the pallet, the pallet is ready to continue with mounting of the dose unit. Once the pallet is positioned in the frame of the dose unit, the mesh is fused to the dose unit frame by means of heat press (melting the frame and overlapping the mesh), ultrasonic welding or optionally any biocompatible glue.

Dronabinol has a boiling point of 250° C. A short time is provided to vaporize and to inhale the drug (about 3 seconds total). The pallet is heated to above 250° C. but below the combustion temperature of the air-permeable matrix material, the frame material and dronabinol.

Example 3

A measured amount (e.g. 30 m$^3$) of acid washed/silanized glass beads having an average size of 75 µm (such as, e.g., SUPELCO 59201) are placed in the dose frame. Optionally, the beads are distributed in the dose frame while placing it horizontally flat against a support surface and shaking the dose frame with the beads inside vertically (for example, by vibrating it and/or the surface on which it rests), until a leveled plain of beads is formed within the frame. Optionally, the dose frame is secured before vibration, to prevent beads from escaping the frame from underneath.

A solution of 5 mg Δ9-tetrahydrocannabinol (Dronabinol THC-10015S) and 1 mg of limonene (Sigma-Aldrich 62118-1 ml) in 50 µl ethanol is prepared.

The solution is gently poured over the glass beads and the dose is placed in a dryer in order to evaporate the ethanol. Optionally, instead, the beads are dipped in the solution and then removed to dry, before being placed into the frame as described above.

Once the ethanol is evaporated, as can be assessed for example by arriving at a constant weight of the beads or the pallet (if already formed), the amount of THC and limonene may be measured or estimated for example by comparing the weight of dried coated beads to the washed beads before being exposed to the THC limonene solution.

Although the embodiments have been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

What is claimed is:

1. A method of delivering to a user an active agent from a dose unit comprised in a dose unit dispenser having a plurality of individual dose units, comprising:
    dispensing an individual dose unit from said dose unit dispenser into a use position of an inhaler, said dose unit having an individually embedded electrically resistive heating element shaped and sized to retain a solid, air-permeable pallet having a low electric conductance so as to avoid current passing therethrough instead of through said electrically resistive heating element, from which said active agent is vaporized;
    said dispensing comprising engaging a geometry of said individual dose unit to transport it to said use position;
    applying a current to said electrically resistive heating element of said dose unit, thereby heating said dose unit and causing at least a portion of said active agent to vaporize; and
    directing airflow through said dose unit out to an output aperture, thereby delivering said vaporized active agent from said dose unit to said user.

2. The method of claim 1, comprising delivering a single dose of said vaporized active agent from said dose unit to said user in a single vaporization event, followed by moving said individual dose unit from said use position.

3. The method of claim 2, comprising delivering said single dose in a single inhalation session.

4. The method of claim 1, comprising delivering said vaporized active agent from said dose unit to said user in a plurality of vaporization events, prior to moving said individual dose unit from said use position.

5. The method of claim 1, comprising controlling said heating to reproducibly deliver a pre-determined amount of said active agent.

6. The method of claim 1, comprising controlling said passing airflow to reproducibly deliver a pre-determined amount of said active agent.

7. The method of claim 1, comprising clamping said individual dose unit prior to said applying.

8. The method of claim 7, wherein said clamping comprises positioning electrodes for contacting said embedded electrically resistive heating element.

9. The method of claim 8, wherein said contacting comprises press contact.

10. The method of claim 7, wherein said clamping comprises sealing an airway passage around at least a portion of said individual dose unit.

11. The method of claim 10, comprising opening said clamping to receive said individual dose unit and closing said clamping to seal an airway passage around at least a portion of said individual dose unit.

12. The method of claim 1, comprising passing current through a pathway extending over all of at least one side of said individual dose unit.

13. The method of claim 1, comprising passing current through a pathway extending over all of two sides of said individual dose unit.

14. The method of claim 13, wherein said passing current comprises evenly distributing heat over a surface of said individual dose unit.

15. The method of claim 1, wherein said dispensing comprises locking said individual dose unit by at least one locking member.

16. The method of claim 15, wherein said dispensing comprises moving said individual dose unit while being locked with said at least one locking member.

17. The method of claim 1, comprising dispensing a new individual dose unit into said use position.

18. The method of claim 1, comprising ejecting said individual dose unit from the use position after said delivering of the vaporized active agent from said dose unit to the user.

19. The method of claim 18, wherein said ejecting comprises moving said individual dose unit out of said use position and into said dose unit dispenser.

20. The method of claim 18, wherein said ejecting comprises disengaging said individual dose unit from a locking member.

21. The method of claim 1, wherein said dispensing comprises engaging and pulling on latch mandibles of said dose unit.

22. The method of claim 1, wherein said dispensing comprises engaging said dose unit using a transport arm of a dose puller.

23. The method of claim 1, comprising controlling the applying of a current and the directing of airflow to reproducibly deliver a predetermined amount of said vaporized active agent.

24. The method of claim 1, wherein when said dose unit is in said use position dispensing of a new dose unit is prevented until said dose unit is returned to said dispenser.

25. The method of claim 1, wherein when said dose unit is in said use position dispensing of a new dose unit is prevented until said dose unit is removed from said use position.

26. The method of claim 1, wherein said pallet comprises a carrier material; said carrier material is formed from substances selected from the group consisting of glass, quartz, ceramic composite, silicon carbide, mullite, alumina, carbon species, silicone and polytetrafluoroethylene.

27. The method of claim 1, wherein said pallet comprises a carrier material, said carrier material is formed from substances consisting of plant material.

28. A method of delivering to a user an active agent from a dose unit comprised in a dose unit dispenser having a plurality of individual dose units, comprising:

dispensing an individual dose unit from said dose unit dispenser into a use position of an inhaler, said dose unit having an individually embedded electrically resistive heating element shaped as two layers and sized to retain therebetween a solid, air-permeable pallet from which said active agent is vaporized;

said dispensing comprising engaging a geometry of said individual dose unit to transport it to said use position;

applying current to said electrically resistive heating element of said dose unit, thereby heating said dose unit and causing at least a portion of said active agent to vaporize; and directing airflow through said dose unit out to an output aperture, thereby delivering said vaporized active agent from said dose unit to said user.

* * * * *